(12) United States Patent
Faridani et al.

(10) Patent No.: US 11,441,169 B2
(45) Date of Patent: Sep. 13, 2022

(54) METHODS OF SMALL-RNA TRANSCRIPTOME SEQUENCING AND APPLICATIONS THEREOF

(71) Applicant: Ludwig Institute for Cancer Research Ltd, Zurich (CH)

(72) Inventors: Omid R. Faridani, Stockholm (SE); Rickard Sandberg, Stockholm (SE)

(73) Assignee: Ludwig Institute for Cancer Research Ltd, Zurich (CH)

( * ) Notice: Subject to any disclaimer, the term of this patent is extended or adjusted under 35 U.S.C. 154(b) by 538 days.

(21) Appl. No.: 16/308,912

(22) PCT Filed: Jun. 15, 2017

(86) PCT No.: PCT/US2017/037620
§ 371 (c)(1),
(2) Date: Dec. 11, 2018

(87) PCT Pub. No.: WO2017/218737
PCT Pub. Date: Dec. 21, 2017

(65) Prior Publication Data
US 2020/0291450 A1 Sep. 17, 2020

Related U.S. Application Data

(60) Provisional application No. 62/351,765, filed on Jun. 17, 2016.

(51) Int. Cl.
*C12Q 1/6806* (2018.01)
*C12Q 1/686* (2018.01)

(52) U.S. Cl.
CPC .......... *C12Q 1/6806* (2013.01); *C12Q 1/686* (2013.01); *C12Q 2525/191* (2013.01);
(Continued)

(58) Field of Classification Search
CPC ........ C12Q 2525/191; C12Q 2525/207; C12Q 2535/122
See application file for complete search history.

(56) References Cited

U.S. PATENT DOCUMENTS

2011/0104785 A1* 5/2011 Vaidyanathan .... C12N 15/1096
435/196
2011/0281736 A1 11/2011 Drmanac et al.
(Continued)

FOREIGN PATENT DOCUMENTS

WO 2015/089333 A1 6/2015

OTHER PUBLICATIONS

Xu et al., An improved protocol for small RNA library construction using High Definition adapters. Meth Next-Gen Seq. 2015, vol. 2, p. 1-10.
(Continued)

*Primary Examiner* — Teresa E Strzelecka
(74) *Attorney, Agent, or Firm* — Fox Rothschild LLP

(57) ABSTRACT

Methods and kits for sequencing and quantification of small RNA molecules from small quantities of starting materials, including single cells, are disclosed. The invention can be applied to, among others, preparing small RNA libraries, synthesizing cDNA from small RNAs, characterizing small RNAs from various cell types, studying cellular heterogeneity in pathological conditions, and diagnosing diseases.

16 Claims, 15 Drawing Sheets

Specification includes a Sequence Listing.

(52) U.S. Cl.
  CPC .  *C12Q 2525/207* (2013.01); *C12Q 2535/122* (2013.01); *C12Q 2537/159* (2013.01); *C12Q 2537/163* (2013.01)

(56) References Cited

U.S. PATENT DOCUMENTS

| | | |
|---|---|---|
| 2012/0108440 A1 | 5/2012 | Lau et al. |
| 2014/0329700 A1 | 11/2014 | Tian et al. |
| 2015/0045237 A1 | 2/2015 | Landthaler et al. |

OTHER PUBLICATIONS

Wickersheim et al., Terminator oligo blocking efficiently eliminates rRNA from *Drosophila* small RNA sequencing libraries. Biotechniques. 2013, vol. 55(5), p. 269-72.

GenBank_AI879918, ar99d 12.x1 Barstead colon HPLRB7 *Homo sapiens* cDNA clone Image:2173751 3—similar to gb|J01866|HUMRRB Human 5.8S ribosomal (rRNA);, mRNA sequence. GenBank Accession No. AI879918. Last Updated: Aug. 23, 1999. [online]. [Retrieved on Sep. 4, 2017]. Retrieved from the Internet: <URL:https://www.ncbi.nlm.nih.gov/nucest/AI879918> Title; and Sequence, the region between nucleotides 1-76.

\* cited by examiner

SEQUENCE LISTING

<160> NUMBER OF SEQ ID NOS: 83

<210> SEQ ID NO 1
<211> LENGTH: 76
<212> TYPE: DNA
<213> ORGANISM: artificial
<220> FEATURE:
<223> OTHER INFORMATION: synthetic

<400> SEQUENCE: 1
atcggcaagc gacgctcaga caggcgtagc cccgggagga acccggggcc gcaagtgcgt    60
tcgaagtgtc gatgat                                                    76

<210> SEQ ID NO 2
<211> LENGTH: 29
<212> TYPE: DNA
<213> ORGANISM: artificial
<220> FEATURE:
<223> OTHER INFORMATION: synthetic

<400> SEQUENCE: 2
ggcgaagccc aaccgacgct cagacaggc                                      29

<210> SEQ ID NO 3
<211> LENGTH: 48
<212> TYPE: DNA
<213> ORGANISM: artificial
<220> FEATURE:
<223> OTHER INFORMATION: synthetic

<400> SEQUENCE: 3
ggcgaagcca agcgacgctc agacaggcgt agccccggga ggaacccg                 48

<210> SEQ ID NO 4
<211> LENGTH: 33
<212> TYPE: DNA
<213> ORGANISM: artificial
<220> FEATURE:
<223> OTHER INFORMATION: synthetic

<400> SEQUENCE: 4
ggcgaagcca agcgacgctc agacaggcgt agc                                 33

<210> SEQ ID NO 5
<211> LENGTH: 21
<212> TYPE: DNA
<213> ORGANISM: artificial
<220> FEATURE:
<223> OTHER INFORMATION: synthetic

<400> SEQUENCE: 5
aaaagcgacg ctcagacagg c                                              21

<210> SEQ ID NO 6
<211> LENGTH: 94
<212> TYPE: DNA
<213> ORGANISM: artificial
<220> FEATURE:
<223> OTHER INFORMATION: synthetic

<400> SEQUENCE: 6
ggcgaagcca agcgacgctc agacaggcgt agccccggga ggaacccggg gccgcaagtg    60
cgttcgaagt gtcgatgatc aatgtggcga agcc                                94

-continued

<210> SEQ ID NO 7
<211> LENGTH: 98
<212> TYPE: DNA
<213> ORGANISM: artificial
<220> FEATURE:
<223> OTHER INFORMATION: synthetic

<400> SEQUENCE: 7
ggcgaagccg tcctgcaatt cacattaatt ctcgcagcta gctgcgttct tcatcgacgc    60
acgagccgag tgatccaccg ctaagagtcg gcgaagcc                            98

<210> SEQ ID NO 8
<211> LENGTH: 76
<212> TYPE: DNA
<213> ORGANISM: artificial
<220> FEATURE:
<223> OTHER INFORMATION: synthetic

<400> SEQUENCE: 8
gcatcggcaa gcgacgctca gacaggcgta gccccgggag gaacccgggg ccgcaagtgc    60
gttcgaagtg tcgatg                                                    76

<210> SEQ ID NO 9
<211> LENGTH: 170
<212> TYPE: DNA
<213> ORGANISM: artificial
<220> FEATURE:
<223> OTHER INFORMATION: synthetic

<400> SEQUENCE: 9
atcggcaagc gacgctcaga caggcgtagc cccggggagga acccggggcc gcaagtgcgt    60
tcgaagtgtc gatgatcaat gtgtcctgca attcacatta attctcgcag ctagctgcgt   120
tcttcatcga cgcacgagcc gagtgatcca ccgctaagag tcgtacgagg              170

<210> SEQ ID NO 10
<211> LENGTH: 31
<212> TYPE: DNA
<213> ORGANISM: artificial
<220> FEATURE:
<223> OTHER INFORMATION: synthetic

<400> SEQUENCE: 10
atcggcaagc gacgctcaga caggcgtagc c                                   31

<210> SEQ ID NO 11
<211> LENGTH: 31
<212> TYPE: DNA
<213> ORGANISM: artificial
<220> FEATURE:
<223> OTHER INFORMATION: synthetic

<400> SEQUENCE: 11
cgagtgatcc accgctaaga gtcgtacgag g                                   31

<210> SEQ ID NO 12
<211> LENGTH: 21
<212> TYPE: DNA
<213> ORGANISM: artificial
<220> FEATURE:
<223> OTHER INFORMATION: synthetic
<220> FEATURE:
<221> NAME/KEY: misc_feature
<222> LOCATION: (21)..(21)
<223> OTHER INFORMATION: n is ribonucleotide adenine

<400> SEQUENCE: 12
ccttggcacc cgagaattcc n                                              21

<210> SEQ ID NO 13
<211> LENGTH: 31
<212> TYPE: DNA
<213> ORGANISM: artificial
<220> FEATURE:
<223> OTHER INFORMATION: synthetic

<400> SEQUENCE: 13
acccgagaat tccaattgat ggtgcctaca g                                   31

<210> SEQ ID NO 14
<211> LENGTH: 20
<212> TYPE: DNA
<213> ORGANISM: artificial
<220> FEATURE:
<223> OTHER INFORMATION: synthetic

<400> SEQUENCE: 14
ccttggcacc cgagaattcc                                                20

<210> SEQ ID NO 15
<211> LENGTH: 20
<212> TYPE: DNA
<213> ORGANISM: artificial
<220> FEATURE:
<223> OTHER INFORMATION: synthetic

<400> SEQUENCE: 15
ccttggcacc cgagaattcc                                                20

<210> SEQ ID NO 16
<211> LENGTH: 22
<212> TYPE: DNA
<213> ORGANISM: artificial
<220> FEATURE:
<223> OTHER INFORMATION: synthetic

<400> SEQUENCE: 16
gccttggcac ccgagaattc ca                                             22

<210> SEQ ID NO 17
<211> LENGTH: 72
<212> TYPE: RNA
<213> ORGANISM: artificial
<220> FEATURE:
<223> OTHER INFORMATION: synthetic

<400> SEQUENCE: 17
rgrururcra rgrargruru rcrurarcra rgrurcrcrg rarcrgraru rcrhrhrhrh    60
rhrhrhrhrc ra                                                       72

<210> SEQ ID NO 18
<211> LENGTH: 34
<212> TYPE: RNA
<213> ORGANISM: artificial
<220> FEATURE:
<223> OTHER INFORMATION: synthetic
<220> FEATURE:
<221> NAME/KEY: misc_feature
<222> LOCATION: (27)..(32)
<223> OTHER INFORMATION: n is a, c, g, or u

<400> SEQUENCE: 18
guucagaguu cuacaguccg acgaucnnnn nnca                        34

<210> SEQ ID NO 19
<211> LENGTH: 36
<212> TYPE: RNA
<213> ORGANISM: artificial
<220> FEATURE:
<223> OTHER INFORMATION: synthetic

<400> SEQUENCE: 19
guucagaguu cuacaguccg acgaucvvvv vvvvca                      36

<210> SEQ ID NO 20
<211> LENGTH: 38
<212> TYPE: RNA
<213> ORGANISM: artificial
<220> FEATURE:
<223> OTHER INFORMATION: synthetic

<400> SEQUENCE: 20
guucagaguu cuacaguccg acgauchhhh hhhhhhca                    38

<210> SEQ ID NO 21
<211> LENGTH: 39
<212> TYPE: DNA
<213> ORGANISM: artificial
<220> FEATURE:
<223> OTHER INFORMATION: synthetic

<400> SEQUENCE: 21
gttcagagtt ctacagtccg acgatchhhr hrhrhrcra                   39

<210> SEQ ID NO 22
<211> LENGTH: 41
<212> TYPE: DNA
<213> ORGANISM: artificial
<220> FEATURE:
<223> OTHER INFORMATION: synthetic

<400> SEQUENCE: 22
gttcagagtt ctacagtccg acgatchhhh hrhrhrhrcr a                41

<210> SEQ ID NO 23
<211> LENGTH: 37
<212> TYPE: RNA
<213> ORGANISM: artificial
<220> FEATURE:
<223> OTHER INFORMATION: synthetic

<400> SEQUENCE: 23
guucagaguu cuacaguccg acgaucrddd dddgaga                     37

<210> SEQ ID NO 24
<211> LENGTH: 36
<212> TYPE: RNA
<213> ORGANISM: artificial
<220> FEATURE:
<223> OTHER INFORMATION: synthetic

<400> SEQUENCE: 24
guucagaguu cuacaguccg acgaucvvvv vvvvca                      36

<210> SEQ ID NO 25
<211> LENGTH: 34
<212> TYPE: RNA

```
<213> ORGANISM: artificial
<220> FEATURE:
<223> OTHER INFORMATION: synthetic

<400> SEQUENCE: 25
guucagaguu cuacaguccg acgaucvvvv vvvv                                    34

<210> SEQ ID NO 26
<211> LENGTH: 33
<212> TYPE: RNA
<213> ORGANISM: artificial
<220> FEATURE:
<223> OTHER INFORMATION: synthetic

<400> SEQUENCE: 26
ccuuggcacc cgaguucuac aguccgacga uch                                     33

<210> SEQ ID NO 27
<211> LENGTH: 44
<212> TYPE: RNA
<213> ORGANISM: artificial
<220> FEATURE:
<223> OTHER INFORMATION: synthetic

<400> SEQUENCE: 27
ccuuggcacc cgaguucuac aguccgacga uchhhhhhhh hhca                         44

<210> SEQ ID NO 28
<211> LENGTH: 35
<212> TYPE: RNA
<213> ORGANISM: artificial
<220> FEATURE:
<223> OTHER INFORMATION: synthetic

<400> SEQUENCE: 28
guucagaguu cuacaguccg acgauchhha hhhca                                   35

<210> SEQ ID NO 29
<211> LENGTH: 35
<212> TYPE: RNA
<213> ORGANISM: artificial
<220> FEATURE:
<223> OTHER INFORMATION: synthetic

<400> SEQUENCE: 29
guucagaguu cuacaguccg acgauchhhu hhhca                                   35

<210> SEQ ID NO 30
<211> LENGTH: 34
<212> TYPE: RNA
<213> ORGANISM: artificial
<220> FEATURE:
<223> OTHER INFORMATION: synthetic

<400> SEQUENCE: 30
guucagaguu cuacaguccg acgauchhhh hhca                                    34

<210> SEQ ID NO 31
<211> LENGTH: 35
<212> TYPE: RNA
<213> ORGANISM: artificial
<220> FEATURE:
<223> OTHER INFORMATION: synthetic

<400> SEQUENCE: 31
guucagaguu cuacaguccg acgaucvvva vvvca                                   35
```

```
<210> SEQ ID NO 32
<211> LENGTH: 35
<212> TYPE: RNA
<213> ORGANISM: artificial
<220> FEATURE:
<223> OTHER INFORMATION: synthetic

<400> SEQUENCE: 32
guucagaguu cuacaguccg acgaucvvvc vvvca                                35

<210> SEQ ID NO 33
<211> LENGTH: 34
<212> TYPE: RNA
<213> ORGANISM: artificial
<220> FEATURE:
<223> OTHER INFORMATION: synthetic

<400> SEQUENCE: 33
guucagaguu cuacaguccg acgaucvvvv vvca                                 34

<210> SEQ ID NO 34
<211> LENGTH: 63
<212> TYPE: DNA
<213> ORGANISM: artificial
<220> FEATURE:
<223> OTHER INFORMATION: synthetic

<400> SEQUENCE: 34
caagcagaag acggcatacg agatcgtgat gtgactggag ttccttggca cccgagaatt     60
cca                                                                   63

<210> SEQ ID NO 35
<211> LENGTH: 63
<212> TYPE: DNA
<213> ORGANISM: artificial
<220> FEATURE:
<223> OTHER INFORMATION: synthetic

<400> SEQUENCE: 35
caagcagaag acggcatacg agatacatcg gtgactggag ttccttggca cccgagaatt     60
cca                                                                   63

<210> SEQ ID NO 36
<211> LENGTH: 63
<212> TYPE: DNA
<213> ORGANISM: artificial
<220> FEATURE:
<223> OTHER INFORMATION: synthetic

<400> SEQUENCE: 36
caagcagaag acggcatacg agatgcctaa gtgactggag ttccttggca cccgagaatt     60
cca                                                                   63

<210> SEQ ID NO 37
<211> LENGTH: 63
<212> TYPE: DNA
<213> ORGANISM: artificial
<220> FEATURE:
<223> OTHER INFORMATION: synthetic

<400> SEQUENCE: 37
caagcagaag acggcatacg agattggtca gtgactggag ttccttggca cccgagaatt     60
```

<210> SEQ ID NO 38
<211> LENGTH: 63
<212> TYPE: DNA
<213> ORGANISM: artificial
<220> FEATURE:
<223> OTHER INFORMATION: synthetic

<400> SEQUENCE: 38
caagcagaag acggcatacg agatcactgt gtgactggag ttccttggca cccgagaatt    60
cca    63

<210> SEQ ID NO 39
<211> LENGTH: 63
<212> TYPE: DNA
<213> ORGANISM: artificial
<220> FEATURE:
<223> OTHER INFORMATION: synthetic

<400> SEQUENCE: 39
caagcagaag acggcatacg agatattggc gtgactggag ttccttggca cccgagaatt    60
cca    63

<210> SEQ ID NO 40
<211> LENGTH: 63
<212> TYPE: DNA
<213> ORGANISM: artificial
<220> FEATURE:
<223> OTHER INFORMATION: synthetic

<400> SEQUENCE: 40
caagcagaag acggcatacg agatgatctg gtgactggag ttccttggca cccgagaatt    60
cca    63

<210> SEQ ID NO 41
<211> LENGTH: 63
<212> TYPE: DNA
<213> ORGANISM: artificial
<220> FEATURE:
<223> OTHER INFORMATION: synthetic

<400> SEQUENCE: 41
caagcagaag acggcatacg agattcaagt gtgactggag ttccttggca cccgagaatt    60
cca    63

<210> SEQ ID NO 42
<211> LENGTH: 63
<212> TYPE: DNA
<213> ORGANISM: artificial
<220> FEATURE:
<223> OTHER INFORMATION: synthetic

<400> SEQUENCE: 42
caagcagaag acggcatacg agatctgatc gtgactggag ttccttggca cccgagaatt    60
cca    63

<210> SEQ ID NO 43
<211> LENGTH: 63
<212> TYPE: DNA
<213> ORGANISM: artificial
<220> FEATURE:
<223> OTHER INFORMATION: synthetic

<400> SEQUENCE: 43
caagcagaag acggcatacg agataagcta gtgactggag ttccttggca cccgagaatt      60
cca                                                                    63

<210> SEQ ID NO 44
<211> LENGTH: 63
<212> TYPE: DNA
<213> ORGANISM: artificial
<220> FEATURE:
<223> OTHER INFORMATION: synthetic

<400> SEQUENCE: 44
caagcagaag acggcatacg agatgtagcc gtgactggag ttccttggca cccgagaatt      60
cca                                                                    63

<210> SEQ ID NO 45
<211> LENGTH: 63
<212> TYPE: DNA
<213> ORGANISM: artificial
<220> FEATURE:
<223> OTHER INFORMATION: synthetic

<400> SEQUENCE: 45
caagcagaag acggcatacg agattacaag gtgactggag ttccttggca cccgagaatt      60
cca                                                                    63

<210> SEQ ID NO 46
<211> LENGTH: 63
<212> TYPE: DNA
<213> ORGANISM: artificial
<220> FEATURE:
<223> OTHER INFORMATION: synthetic

<400> SEQUENCE: 46
caagcagaag acggcatacg agatttgact gtgactggag ttccttggca cccgagaatt      60
cca                                                                    63

<210> SEQ ID NO 47
<211> LENGTH: 63
<212> TYPE: DNA
<213> ORGANISM: artificial
<220> FEATURE:
<223> OTHER INFORMATION: synthetic

<400> SEQUENCE: 47
caagcagaag acggcatacg agatggaact gtgactggag ttccttggca cccgagaatt      60
cca                                                                    63

<210> SEQ ID NO 48
<211> LENGTH: 63
<212> TYPE: DNA
<213> ORGANISM: artificial
<220> FEATURE:
<223> OTHER INFORMATION: synthetic

<400> SEQUENCE: 48
caagcagaag acggcatacg agattgacat gtgactggag ttccttggca cccgagaatt      60
cca                                                                    63

<210> SEQ ID NO 49

```
<211> LENGTH: 63
<212> TYPE: DNA
<213> ORGANISM: artificial
<220> FEATURE:
<223> OTHER INFORMATION: synthetic

<400> SEQUENCE: 49
caagcagaag acggcatacg agatggacgg gtgactggag ttccttggca cccgagaatt       60
cca                                                                    63

<210> SEQ ID NO 50
<211> LENGTH: 63
<212> TYPE: DNA
<213> ORGANISM: artificial
<220> FEATURE:
<223> OTHER INFORMATION: synthetic

<400> SEQUENCE: 50
caagcagaag acggcatacg agatctctac gtgactggag ttccttggca cccgagaatt       60
cca                                                                    63

<210> SEQ ID NO 51
<211> LENGTH: 63
<212> TYPE: DNA
<213> ORGANISM: artificial
<220> FEATURE:
<223> OTHER INFORMATION: synthetic

<400> SEQUENCE: 51
caagcagaag acggcatacg agatgcggac gtgactggag ttccttggca cccgagaatt       60
cca                                                                    63

<210> SEQ ID NO 52
<211> LENGTH: 63
<212> TYPE: DNA
<213> ORGANISM: artificial
<220> FEATURE:
<223> OTHER INFORMATION: synthetic

<400> SEQUENCE: 52
caagcagaag acggcatacg agattttcac gtgactggag ttccttggca cccgagaatt       60
cca                                                                    63

<210> SEQ ID NO 53
<211> LENGTH: 63
<212> TYPE: DNA
<213> ORGANISM: artificial
<220> FEATURE:
<223> OTHER INFORMATION: synthetic

<400> SEQUENCE: 53
caagcagaag acggcatacg agatggccac gtgactggag ttccttggca cccgagaatt       60
cca                                                                    63

<210> SEQ ID NO 54
<211> LENGTH: 63
<212> TYPE: DNA
<213> ORGANISM: artificial
<220> FEATURE:
<223> OTHER INFORMATION: synthetic

<400> SEQUENCE: 54
caagcagaag acggcatacg agatcgaaac gtgactggag ttccttggca cccgagaatt       60
```

```
cca                                                              63

<210> SEQ ID NO 55
<211> LENGTH: 63
<212> TYPE: DNA
<213> ORGANISM: artificial
<220> FEATURE:
<223> OTHER INFORMATION: synthetic

<400> SEQUENCE: 55
caagcagaag acggcatacg agatcgtacg gtgactggag ttccttggca cccgagaatt    60
cca                                                              63

<210> SEQ ID NO 56
<211> LENGTH: 63
<212> TYPE: DNA
<213> ORGANISM: artificial
<220> FEATURE:
<223> OTHER INFORMATION: synthetic

<400> SEQUENCE: 56
caagcagaag acggcatacg agatccactc gtgactggag ttccttggca cccgagaatt    60
cca                                                              63

<210> SEQ ID NO 57
<211> LENGTH: 63
<212> TYPE: DNA
<213> ORGANISM: artificial
<220> FEATURE:
<223> OTHER INFORMATION: synthetic

<400> SEQUENCE: 57
caagcagaag acggcatacg agatgctacc gtgactggag ttccttggca cccgagaatt    60
cca                                                              63

<210> SEQ ID NO 58
<211> LENGTH: 63
<212> TYPE: DNA
<213> ORGANISM: artificial
<220> FEATURE:
<223> OTHER INFORMATION: synthetic

<400> SEQUENCE: 58
caagcagaag acggcatacg agatatcagt gtgactggag ttccttggca cccgagaatt    60
cca                                                              63

<210> SEQ ID NO 59
<211> LENGTH: 63
<212> TYPE: DNA
<213> ORGANISM: artificial
<220> FEATURE:
<223> OTHER INFORMATION: synthetic

<400> SEQUENCE: 59
caagcagaag acggcatacg agatgctcat gtgactggag ttccttggca cccgagaatt    60
cca                                                              63

<210> SEQ ID NO 60
<211> LENGTH: 63
<212> TYPE: DNA
<213> ORGANISM: artificial
<220> FEATURE:
```

<223> OTHER INFORMATION: synthetic

<400> SEQUENCE: 60
caagcagaag acggcatacg agataggaat gtgactggag ttccttggca cccgagaatt     60
cca                                                                   63

<210> SEQ ID NO 61
<211> LENGTH: 63
<212> TYPE: DNA
<213> ORGANISM: artificial
<220> FEATURE:
<223> OTHER INFORMATION: synthetic

<400> SEQUENCE: 61
caagcagaag acggcatacg agatcttttg gtgactggag ttccttggca cccgagaatt     60
cca                                                                   63

<210> SEQ ID NO 62
<211> LENGTH: 63
<212> TYPE: DNA
<213> ORGANISM: artificial
<220> FEATURE:
<223> OTHER INFORMATION: synthetic

<400> SEQUENCE: 62
caagcagaag acggcatacg agattagttg gtgactggag ttccttggca cccgagaatt     60
cca                                                                   63

<210> SEQ ID NO 63
<211> LENGTH: 63
<212> TYPE: DNA
<213> ORGANISM: artificial
<220> FEATURE:
<223> OTHER INFORMATION: synthetic

<400> SEQUENCE: 63
caagcagaag acggcatacg agatccggtg gtgactggag ttccttggca cccgagaatt     60
cca                                                                   63

<210> SEQ ID NO 64
<211> LENGTH: 63
<212> TYPE: DNA
<213> ORGANISM: artificial
<220> FEATURE:
<223> OTHER INFORMATION: synthetic

<400> SEQUENCE: 64
caagcagaag acggcatacg agatatcgtg gtgactggag ttccttggca cccgagaatt     60
cca                                                                   63

<210> SEQ ID NO 65
<211> LENGTH: 63
<212> TYPE: DNA
<213> ORGANISM: artificial
<220> FEATURE:
<223> OTHER INFORMATION: synthetic

<400> SEQUENCE: 65
caagcagaag acggcatacg agattgagtg gtgactggag ttccttggca cccgagaatt     60
cca                                                                   63

```
<210> SEQ ID NO 66
<211> LENGTH: 63
<212> TYPE: DNA
<213> ORGANISM: artificial
<220> FEATURE:
<223> OTHER INFORMATION: synthetic

<400> SEQUENCE: 66
caagcagaag acggcatacg agatcgcctg gtgactggag ttccttggca cccgagaatt      60
cca                                                                  63

<210> SEQ ID NO 67
<211> LENGTH: 63
<212> TYPE: DNA
<213> ORGANISM: artificial
<220> FEATURE:
<223> OTHER INFORMATION: synthetic

<400> SEQUENCE: 67
caagcagaag acggcatacg agatgccatg gtgactggag ttccttggca cccgagaatt      60
cca                                                                  63

<210> SEQ ID NO 68
<211> LENGTH: 63
<212> TYPE: DNA
<213> ORGANISM: artificial
<220> FEATURE:
<223> OTHER INFORMATION: synthetic

<400> SEQUENCE: 68
caagcagaag acggcatacg agataaaatg gtgactggag ttccttggca cccgagaatt      60
cca                                                                  63

<210> SEQ ID NO 69
<211> LENGTH: 47
<212> TYPE: DNA
<213> ORGANISM: artificial
<220> FEATURE:
<223> OTHER INFORMATION: synthetic

<400> SEQUENCE: 69
caagcagaag acggcatacg agattgttgg gtgactggag ttccttg                   47

<210> SEQ ID NO 70
<211> LENGTH: 63
<212> TYPE: DNA
<213> ORGANISM: artificial
<220> FEATURE:
<223> OTHER INFORMATION: synthetic

<400> SEQUENCE: 70
caagcagaag acggcatacg agatattccg gtgactggag ttccttggca cccgagaatt      60
cca                                                                  63

<210> SEQ ID NO 71
<211> LENGTH: 63
<212> TYPE: DNA
<213> ORGANISM: artificial
<220> FEATURE:
<223> OTHER INFORMATION: synthetic

<400> SEQUENCE: 71
caagcagaag acggcatacg agatagctag gtgactggag ttccttggca cccgagaatt      60
``` cca                                                             63

<210> SEQ ID NO 72
<211> LENGTH: 63
<212> TYPE: DNA
<213> ORGANISM: artificial
<220> FEATURE:
<223> OTHER INFORMATION: synthetic

<400> SEQUENCE: 72
caagcagaag acggcatacg agatgtatag gtgactggag ttccttggca cccgagaatt    60
cca                                                             63

<210> SEQ ID NO 73
<211> LENGTH: 63
<212> TYPE: DNA
<213> ORGANISM: artificial
<220> FEATURE:
<223> OTHER INFORMATION: synthetic

<400> SEQUENCE: 73
caagcagaag acggcatacg agattctgag gtgactggag ttccttggca cccgagaatt    60
cca                                                             63

<210> SEQ ID NO 74
<211> LENGTH: 63
<212> TYPE: DNA
<213> ORGANISM: artificial
<220> FEATURE:
<223> OTHER INFORMATION: synthetic

<400> SEQUENCE: 74
caagcagaag acggcatacg agatgtcgtc gtgactggag ttccttggca cccgagaatt    60
cca                                                             63

<210> SEQ ID NO 75
<211> LENGTH: 63
<212> TYPE: DNA
<213> ORGANISM: artificial
<220> FEATURE:
<223> OTHER INFORMATION: synthetic

<400> SEQUENCE: 75
caagcagaag acggcatacg agatcgatta gtgactggag ttccttggca cccgagaatt    60
cca                                                             63

<210> SEQ ID NO 76
<211> LENGTH: 63
<212> TYPE: DNA
<213> ORGANISM: artificial
<220> FEATURE:
<223> OTHER INFORMATION: synthetic

<400> SEQUENCE: 76
caagcagaag acggcatacg agatgctgta gtgactggag ttccttggca cccgagaatt    60
cca                                                             63

<210> SEQ ID NO 77
<211> LENGTH: 63
<212> TYPE: DNA
<213> ORGANISM: artificial
<220> FEATURE:
<223> OTHER INFORMATION: synthetic

```
<400> SEQUENCE: 77
caagcagaag acggcatacg agatattata gtgactggag ttccttggca cccgagaatt      60
cca                                                                   63

<210> SEQ ID NO 78
<211> LENGTH: 63
<212> TYPE: DNA
<213> ORGANISM: artificial
<220> FEATURE:
<223> OTHER INFORMATION: synthetic

<400> SEQUENCE: 78
caagcagaag acggcatacg agatgaatga gtgactggag ttccttggca cccgagaatt      60
cca                                                                   63

<210> SEQ ID NO 79
<211> LENGTH: 63
<212> TYPE: DNA
<213> ORGANISM: artificial
<220> FEATURE:
<223> OTHER INFORMATION: synthetic

<400> SEQUENCE: 79
caagcagaag acggcatacg agattcggga gtgactggag ttccttggca cccgagaatt      60
cca                                                                   63

<210> SEQ ID NO 80
<211> LENGTH: 63
<212> TYPE: DNA
<213> ORGANISM: artificial
<220> FEATURE:
<223> OTHER INFORMATION: synthetic

<400> SEQUENCE: 80
caagcagaag acggcatacg agatcttcga gtgactggag ttccttggca cccgagaatt      60
cca                                                                   63

<210> SEQ ID NO 81
<211> LENGTH: 63
<212> TYPE: DNA
<213> ORGANISM: artificial
<220> FEATURE:
<223> OTHER INFORMATION: synthetic

<400> SEQUENCE: 81
caagcagaag acggcatacg agattgccga gtgactggag ttccttggca cccgagaatt      60
cca                                                                   63

<210> SEQ ID NO 82
<211> LENGTH: 21
<212> TYPE: DNA
<213> ORGANISM: artificial
<220> FEATURE:
<223> OTHER INFORMATION: synthetic

<400> SEQUENCE: 82
tggaattctc gggtgccaag g                                               21

<210> SEQ ID NO 83
<211> LENGTH: 50
<212> TYPE: DNA
```

```
<213> ORGANISM: artificial
<220> FEATURE:
<223> OTHER INFORMATION: synthetic

<400> SEQUENCE: 83
aatgatacgg cgaccaccga gatctacacg ttcagagttc tacagtccga            50
```

METHODS OF SMALL-RNA TRANSCRIPTOME SEQUENCING AND APPLICATIONS THEREOF

CROSS REFERENCE TO RELATED APPLICATIONS

This application claims priority under 35 U.S.C. § 119(e) to U.S. Provisional Application No. 62/351,765, filed on Jun. 17, 2016, which is incorporated herein by reference in its entirety.

FIELD OF THE INVENTION

The present invention relates generally to the field of molecular biology. More particularly, it concerns methods and compositions for sequencing of short RNAs starting with small quantities of RNA, including from a single cell.

BACKGROUND OF THE INVENTION

While most of the DNA in higher eukaryotes is transcribed into RNA, the vast majority of the genome does not encode proteins, but is transcribed into non-coding RNAs (Wong et al., Genome Research 11, 1975-1977 (2001)). These non-coding ribonucleic acids play essential roles in the post-transcriptional modulation of gene expression and protein production and are thus critical regulators in development, physiology, and disease. Originally discovered in nematodes and plants, RNA-dependent regulation of gene expression is widely found in eukaryotic organisms, and comparable small RNA guided regulatory pathways have been found in prokaryotes as well. Accordingly, data related to the abundance and identity of non-coding RNA molecules present in a specific cell, tissue, or organism hold a tremendous amount of information about, for example, biological pathways that are engaged in various physiological conditions, tissue-specific expression patterns, rare cellular phenotypes, disease associations, and potential targets for therapeutic intervention (Hirose et al., EMBO Rep 15(5), 489-507 (2014), Zhang, Curr Opin Mol Ther. 11(6), 641-51 (2009)).

Small RNAs (sRNAs) constitute a family of short, non-protein encoding ribonucleic acids that are involved in cell differentiation, growth, proliferation, migration, apoptosis, metabolism, and defense (e.g., against viruses). Several classes of sRNAs exist in mammalian cells, including micro RNAs (miRNA), small interfering RNAs (siRNAs), P element-induced wimpy testis (Piwi) interacting RNAs (piRNAs), small nucleolar RNAs (snoRNAs), small cajal body-specific RNAs (scaRNAs), repeat-associated siRNAs (rasiRNAs), trans-acting siRNAs (ta-siRNAs), and heterochromatic siRNA (hc-siRNA), as well as smaller fragments derived from snoRNAs (sdRNAs) or transfer RNAs (tsRNAs). Typically around 18-30 nucleotides in length, these short RNA molecules can exert their regulatory functions in the cytoplasm and the nucleus through transcriptional silencing, cleavage and accelerated degradation of mRNAs, inhibition of RNA translation, sequestration of transcripts, RNA activation, and/or epigenetic modifications targeted to specific regions of the genome. Each tissue, cell type, and cellular state is characterized by a unique sRNA profile. Further, sRNAs can play a role in disease, and aberrant expression of sRNAs has been reported in the context of cancer, cardiovascular diseases, neurodegenerative diseases, liver and kidney diseases, diabetes, and viral infections. Finally, due to their ability to bind materials such as exosomes, sRNAs are also relatively stable in the blood, allowing the use of sRNAs as diagnostic markers for various pathological conditions (Zhang, Curr. Opin. Mol. Ther., 11(6), 641-51 (2009)).

Established techniques aimed at analyzing cellular sRNA profiles include gel-based assays (such as Northern blotting, primer extension, or RNAse protection assays), microarrays, and real-time PCR. However, each of these technologies suffers from one or more of the following shortcomings, including (1) difficulty of target amplification due to the short size of the sRNAs, (2) detection of RNA sequences that is limited to known RNA sequences, (3) low throughput, (4) requirement for high concentration of input target for efficient hybridization and signal generation, (5) poor sensitivity for rare targets, (6) necessity for post-assay validation with more sensitive assays, and (7) difficulty of implementation. While more recently developed next generation sequencing (NGS)-based technologies have overcome some of the problems associated with the more traditional sRNA profiling methods, high-throughput RNA sequencing (RNA-Seq) of sRNAs is technically still very difficult for various reasons:

1. In comparison to sequencing of longer RNA fragments (>200 nucleotides), sequencing of very short RNA molecules requires much larger amounts of starting material. This is especially problematic when the amount of starting material is limited, as it is in the case of extracellular RNA, relatively small numbers of cells, clinical samples, RNA isolated from cellular compartments such as mitochondria or nuclei, or RNA purified after immunoprecipitation. Due to small number of RNA molecules per cell, many RNA-Seq protocols rely on the analysis of bulk RNA obtained from tissue samples, which typically contain millions of cells. While informative in some cases, this approach only provides average RNA expression profiles. Such profiles are of limited value for the study of discrete cell types in complex tissues such as tumors or the brain, differences in anatomical and temporal expression, or dynamic processes such as cell cycle progression. These situations require resolution of RNA expression on the single cell level, rather than population averages.

2. RNA samples that are used for RNA-Seq are oftentimes highly contaminated with ribosomal RNA (rRNA), which can make up to 85% of the total RNA amount in biological samples. This means that significant resources are dedicated to the generation of sequencing reads that are uninformative and that prevent a more sensitive detection of the sRNA sequences of interest.

3. Many RNA-Seq protocols require a size selection step to enrich for RNAs of a desired length, a tedious and time-consuming process that prevents high-throughput processing of samples and can lead to loss of sample.

4. While existing methods based on NGS have shown some success for the differential expression analysis of sRNAs, the number of sequencing reads obtained for each sRNA type with these approaches does not necessarily reflect the actual abundance of the particular sRNA species in the sample. This is due to biases that are introduced during sample preparation and target amplification in many RNA-Seq protocols.

In summary, there remains a considerable need for robust and reproducible methods that allow the sensitive and reliable quantification of sRNAs with known and unknown sequences in complex mixtures. Ideally, these methods should work with very small amounts of starting material, including single cells, and should be suitable for rapid adoption by researchers accustomed to standard RNA-Seq protocols and platforms.

SUMMARY OF THE INVENTION

The present invention relates to methods and kits that enable sequencing and quantification of RNA molecules from very small amount of starting material with high sensitivity, reproducibility, and quantitative accuracy. Specifically, the invention relates to the detection and quantification of short RNA sequences, including sRNA. Protocols contemplated by the invention do not require any RNA size selection step, which makes the methods presented herein suitable for automation. Methods and kits contemplated by the invention are further suitable for single cell analysis and can be readily adopted by researchers accustomed to standard RNA-Seq protocols and platforms.

In one aspect, the present invention provides a method for treating, detecting, or preparing an RNA sample, comprising:
  (a) providing a sample containing RNA molecules;
  (b) masking ribosomal RNA molecules by providing one or more oligonucleotide(s) complementary to the RNA to be masked;
  (c) ligating a 3' oligonucleotide adaptor to the 3' end of small RNA molecules;
  (d) hybridizing one or more reverse transcription (RT) primer oligonucleotide(s) to both the free and the ligated form of said 3' oligonucleotide adaptor;
  (e) removing the free 3' oligonucleotide adaptor/RT primer-dimer by enzymatic digest;
  (f) ligating a 5' oligonucleotide adaptor to the 5' end of said small RNA molecules;
  (g) performing reverse transcription of the RNA; and
  (h) performing one PCR reaction with RT primer and RP1 primer and a second PCR with RP1 and indexed primers.

In another aspect, the present invention provides a kit for performing a method of treating, detecting, or preparing an RNA sample, the kit comprising:
  one or more RNA masking oligonucleotide(s),
  one or more 3' oligonucleotide adaptor(s),
  one or more 5' oligonucleotide adaptor(s),
  one or more RT primer(s),
  one or more RP1 primer(s), and
  indexed primer(s).

In another aspect, the methods and kit of the present invention can be used for, but not limited to, synthesis of cDNA from small RNAs, preparation of small RNA libraries, and diagnosis of diseases or disorders that are associated with small RNAs.

Also provided are specific oligonucleotides, RNA masks, adaptors, primers, and enzymes that are particularly useful for performing the methods contemplated by the invention.

These and other features, aspects and advantages of the present invention will become better understood with regard to the following description, appended claims, and accompanying drawings.

DETAILED DESCRIPTION OF THE INVENTION

Figure 1:
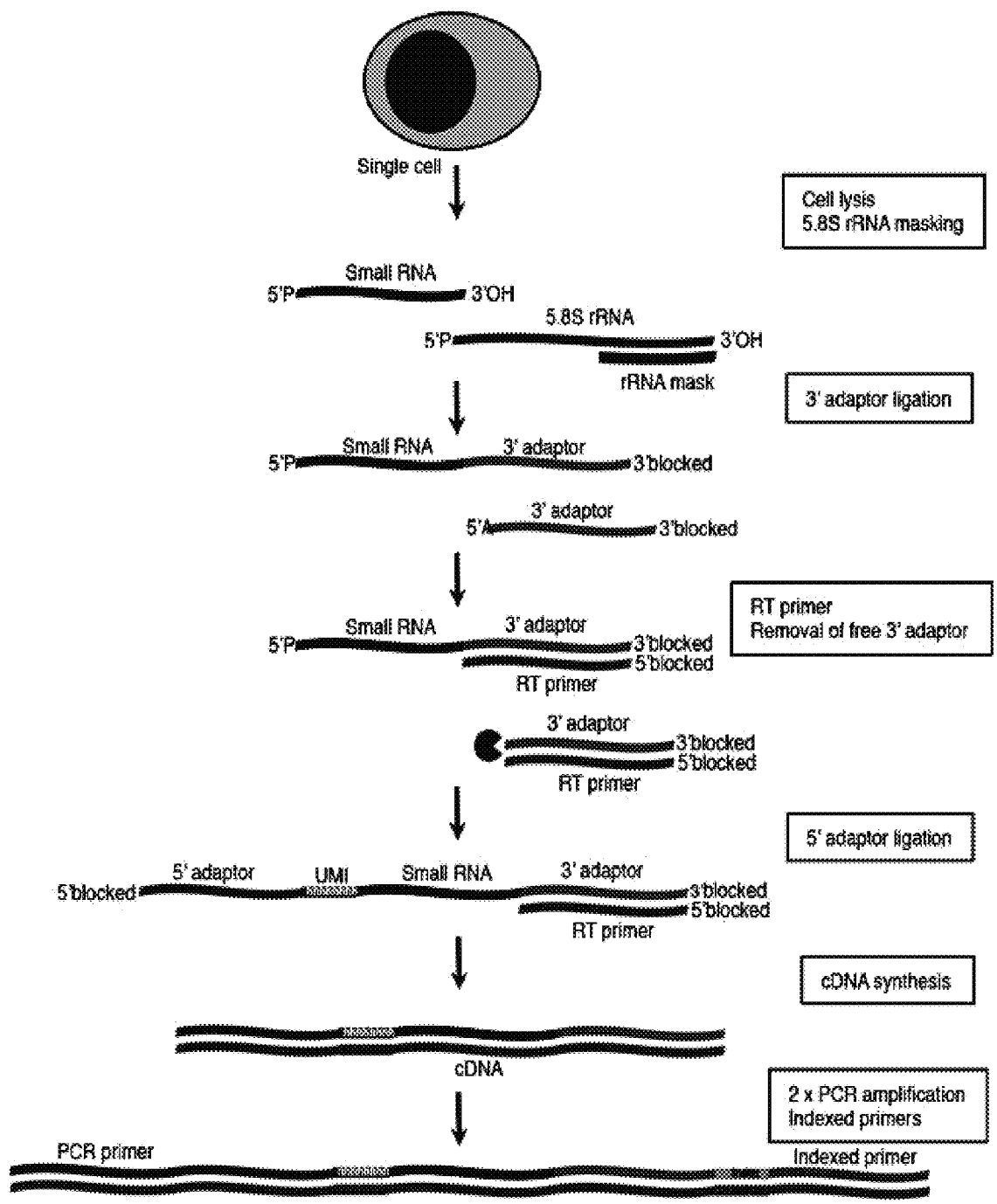
FIG. 1 illustrates a schematic outline of the single-cell sRNA library preparation. Single cells were lysed directly in the preparation tube and 5.8S rRNA was masked for adaptor ligation immediately with a complementary oligo. Then, the 3' adaptor was ligated to the sRNAs and the free adaptor was removed enzymatically prior to 5' adaptor ligation. The 5' adaptor contained a unique molecular identifier (UMI) to allow the later removal of PCR replicates. Sequences required for Illumina® cluster generation and sample indexing were added in two rounds of PCR amplifications.

Unless defined otherwise, all technical and scientific terms used herein have the same meanings as commonly understood by one of ordinary skill in the art to which this invention belongs. All patents, published patent applications, and other publications referred to herein are incorporated by reference in their entirety and are not admitted to be prior art with respect to the present invention by their mention. If a definition set forth in this section is contrary to or otherwise inconsistent with a definition set forth in the patents, published patent applications, and other publications that are herein incorporated by reference, the definition set forth in this section prevails over the definition that is incorporated herein by reference.

Unless indicated otherwise, the terms below have the following meaning:

As used herein, the singular forms "a," "an," and "the" include plural reference unless the context clearly dictates otherwise. Thus, for example, reference to "an" oligonucleotide is a reference to one or more oligonucleotides and equivalents thereof known to those skilled in the art, and so forth.

As used herein, the terms "amplification" or "nucleic acid amplification" refer to the production of multiple copies of a target nucleic acid that contains at least a portion of the intended specific target nucleic acid sequence. The multiple copies may be referred to as "amplicons" or "amplification products." Typically, the amplified portion contains a detectable target sequence that may be detected using any of a variety of well-known methods. One of the most common nucleic acid amplification techniques, polymerase chain reaction (PCR), requires thermocycling to alternately denature double-stranded nucleic acids and hybridize primers; however, other well-known methods of nucleic acid amplification are isothermal. PCR (Mullis et al., U.S. Pat. No. 4,683,195; Mullis, U.S. Pat. No. 4,683,202; and Mullis et al., U.S. Pat. No. 4,800,159) uses multiple cycles of denaturation, annealing of primer pairs to opposite strands, and primer extension to exponentially increase copy numbers of the target sequence. Many other nucleic acid amplification techniques have also been described in the art and can be applied in the context of the present invention.

As used herein, the terms "complementary" or "complementarity," when used in reference to nucleic acids (i.e., a sequence of nucleotides such as an oligonucleotide or a target nucleic acid), refer to sequences that are related by base-pairing rules. For natural bases, the base pairing rules are those developed by Watson and Crick. For non-natural bases, as described herein, the base-pairing rules include the formation of hydrogen bonds in a manner similar to the Watson-Crick base pairing rules or by hydrophobic, entropic, or van der Waals forces. As an example, for the sequence "T-G-A", the complementary sequence is "A-C-T." Complementarity can be "partial," in which only some of the bases of the nucleic acids are matched according to the base pairing rules. Alternatively, there can be "complete" or "total" complementarity between the nucleic acids. The degree of complementarity between the nucleic acid strands has effects on the efficiency and strength of hybridization between the nucleic acid strands.

As used herein, the terms "hybridizing", "hybridization," or "annealing" refer to a process of interaction between two or more polynucleotides forming a complementary complex through base pairing which is most commonly a duplex or double-stranded complex as originally described in Marmur and Lane, *Proc. Natl. Acad. Sci. USA*, 46, 453-461 (1960) and Doty et al., *Proc. Natl. Acad. Sci. USA*, 46, 461-476 (1960).

As used herein, the term "kit" refers to one or more suitably aliquoted compositions or reagents for use in the methods of the present disclosure. The components of the kits may be packaged either in aqueous or lyophilized form. The container means of the kits may include at least one vial, test tube, flask, bottle, syringe, or other container means, into which a component may be placed, and preferably, suitably aliquoted. Where there is more than one component in the kit, the kit also will generally contain a second, third, or other additional container into which the additional components may be separately placed. However, various combinations of components may be contained in a vial. The kits of the present disclosure also will typically include a means for containing the reagent containers in close confinement for commercial sale. Such containers may include injection or blow molded plastic containers into which the desired vials are retained, for example.

As used herein, the term "label" refers to any atom or molecule that can be used to provide a detectable signal and that can be attached to a nucleic acid or oligonucleotide. Labels include, but are not limited, to isotopes, radiolabels such as $^{32}P$; binding moieties such as biotin; haptens such as dioxygenin; luminogenic, mass tags; phosphorescent or fluorescent moieties, fluorescent dyes alone or in combination with other dyes or moieties that can suppress or shift emission spectra by FRET effect. Labels may provide signals detectable by fluorescence, radioactivity, colorimetry, gravimetry, X-ray diffraction or absorption, magnetism, enzymatic activity, mass spectrometry, binding affinity and the like. A label may be a charged moiety or alternatively, may be charge neutral. Labels can include or consist of nucleic acid or protein sequence, so long as the sequence comprising the label is detectable.

As used herein, the term "ligase" refers to an enzyme that is capable of joining a hydroxyl terminus of one nucleic acid molecule to a phosphate terminus of either the same or a second nucleic acid molecule to form either a circular nucleic acid or a single linear molecule. Such enzymes may use RNA and/or DNA as a substrate. Such enzymes may join a 3' hydroxyl terminus and a 5' phosphate terminus. Alternatively, such enzymes may join a 5' hydroxyl terminus and a 3' phosphate terminus.

As used herein, the term "ligation" refers to the covalent coupling of two adjacent nucleotide sequences, e.g. the tagging oligonucleotide probe sequences of the invention, to form a single nucleotide sequence. The reaction is catalyzed by the enzyme ligase, which forms a phosphodiester bond between the 5'-end of one nucleotide sequence and the 3'-end of the adjacent nucleotide sequence, e.g. between the two adjacent tagging probes of invention, annealed to their complementary, target nucleic acid sequence.

As used herein, the term "next generation sequencing" (NGS) refers to any nucleic acid sequencing device that utilizes massively parallel technology. For example, NGS platforms may include, but are not limited to, Illumina®, Roche 454, Pacific Bioscience, Ion Torrents, Harvard Polonator, ABI Solid or other similar instruments in the field. Classic sequencing approaches, such as Sanger sequencing can be used; however, the true power in the technology is its ability to sequence a larger number of sequences from single cells simultaneously.

As used herein, the term "nucleotide" refers to a base-sugar-phosphate combination. Nucleotides are the monomeric units of nucleic acid polymers, i.e., of DNA and RNA. The term includes ribonucleotide triphosphates, such as rATP, rCTP, rGTP, or rUTP, and deoxyribonucleotide triphosphates, such as dATP, dCTP, dUTP, dGTP, or dTTP.

The term "polynucleotide" and "oligonucleotide" are used interchangeably herein, and each means a linear polymer of nucleotide monomers. Polynucleotides typically range in size from a few monomeric units, e.g. 5-40, when they are usually referred to as "oligonucleotides", to several thousand monomeric units. The exact size will depend on many factors, which in turn depends on the ultimate function or use of the oligonucleotide. The oligonucleotide may be generated in any manner, including chemical synthesis, DNA replication, reverse transcription, or a combination thereof. Whenever a polynucleotide or oligonucleotide is represented by a sequence of letters, for example, "CCGTATG", it is understood herein, unless otherwise specified in the text, that the nucleotides are in 5'-3' order from left to right and that "A" denotes deoxyadenosine, "C" denotes deoxycytidine, "G" denotes deoxyguanosine, and "T" denotes deoxythymidine, unless otherwise indicated or obvious from context. Usually DNA polynucleotides comprise these four deoxyribonucleosides linked by phosphodiester linkage whereas RNA comprises their four ribose counterparts with uridine ("U") in place of "T".

As used herein, the term "primer" refers to a single-stranded oligonucleotide or a single-stranded polynucleotide that is extended by covalent addition of nucleotide monomers during amplification. Often, nucleic acid amplification is based on nucleic acid synthesis by a nucleic acid polymerase. Many such polymerases require the presence of a primer that can be extended to initiate nucleic acid synthesis.

As used herein the phrase "reverse transcription" refers to a process whereby an RNA-dependent DNA polymerase having reverse transcriptase activity extends an oligonucleotide primer hybridized to an RNA template, in the presence of deoxynucleoside 5'-triphosphates (dNTPs), whether natural or modified, resulting in synthesis of complementary DNA (cDNA).

As used herein, the term "RT-primer" refers to a primer, comprising a recognition sequence, complementary to a sequence in the target deoxyribonucleic and/or ribonucleic acid sequence. Said RT-primer is used as an anchored primer in a reverse transcription reaction to generate a primer extension product, complementary to the target RNA sequence using a reverse transcriptase enzyme.

As used herein, the term "sample" refers to a sample of cells, tissue, or fluid isolated from an organism or organisms. Non-limiting examples for samples are blood, serum, plasma, reticulocytes, lymphocytes, any product prepared from blood or lymph, bone marrow tissue, cerebrospinal fluid, sweat, tear, saliva, sputum, amniotic fluid, seminal fluid, vaginal excretion, serous fluid, synovial fluid, pericardial fluid, peritoneal fluid, pleural fluid, transudates, exudates, cystic fluid, bile, urine, gastric fluid, intestinal fluid, or fecal samples), any type of tissue biopsy (e.g. a tumor biopsy, a muscle biopsy, a liver biopsy, a kidney biopsy, a bladder biopsy, a bone biopsy, a cartilage biopsy, a skin biopsy, a pancreas biopsy, a biopsy of the intestinal tract, a thymus biopsy, a uterus biopsy, a testicular biopsy, an eye biopsy or a brain biopsy), or any other biological material that may harbor RNA molecules. Suitable samples further comprise clinical samples (which are samples provided by a patient), biological swabs and biological washes.

As used herein, a "small quantity" of RNA refers to a quantity of RNA less than 100 ng, 50 ng, 10 ng, 1 ng, 500 pg, 250 pg, 100 pg, 50 pg, or 10 pg, or any number derivable therein. A small quantity of RNA may be contained in a range of volumes of a suitable liquid (e.g., $dH_2O$, a buffer, ethanol, etc.), such as, for example 1-10 µl, 1-100 µl, 1-1000 al, 10-200 µl, 10-100 µl, or 100-1000 µl, or any range derivable therein. A small quantity of RNA may be in lyophilized form. Non-limiting examples of sources of small quantities of RNA include RNA isolated from immunoprecipitation, such as cross-linking immunoprecipitation (CLIP) RNA, RNA extracted from a single cell, extracellular RNA, or RNA isolated from intracellular organelles, such as mitochondria and nuclei.

As used herein, the term "small" RNA as used herein refers to an RNA less than 200 nucleotides in length. Such an RNA may consist of less than 200 nt, 150 nt, 100 nt, 90 nt, 80 nt, 70 nt, 60 nt, 50 nt, 40 nt, 30 nt, 20 nt, or 10 nt, or any number derivable therein. In a sample comprising a population of short RNAs, the sample may contain RNAs of various lengths, such as between 10 nt and 200 nt, 10 nt and 100 nt, 20 nt and 150 nt, 20 nt and 100 nt, 20 nt and 50 nt, or any range derivable therein. In certain embodiments, sRNAs refer to short non-coding RNA sequences that include micro RNAs (miRNA), small interfering RNAs (siRNAs), P element-induced wimpy testis (Piwi) interacting RNAs (piRNAs), small nucleolar RNAs (snoRNAs), small cajal body-specific RNAs (scaRNAs), repeat-associated siRNAs (rasiRNAs), trans-acting siRNAs (ta-siRNAs), and heterochromatic siRNA (hc-siRNA), as well as smaller fragments derived from snoRNAs (sdRNAs) or transfer RNAs (tsRNAs). SRNAs can function for example in the control of mRNA stability or translation and/or can target epigenetic modifications to specific regions of the genome.

As used herein, the term "unique molecular identifier" (UMI) refers to a unique nucleic acid sequence that is attached to each of a plurality of nucleic acid molecules. When incorporated into a nucleic acid molecule, a UMI can be used to correct for subsequent amplification bias by directly counting unique UMIs that are sequenced after amplification. The design, incorporation, and application of UMIs can take place as known in the art, as exemplified by, for example, the disclosures of WO 2012/142213, Islam et al., Nat. Methods 11, 163-166 (2014), and Kivioja et al., Nat. Methods 9, 72-74 (2012).

Before the present compositions and methods are described, it is to be understood that this invention is not limited to the particular molecules, compositions, methodologies, or protocols described, as these may vary. Any methods and materials similar or equivalent to those described herein can be used in the practice or testing of embodiments of the present invention. It is also to be understood that the terminology used in the description is for the purpose of describing the particular versions or embodiments only, and is not intended to limit the scope of the present invention, which will be limited only by the appended claims. It is further to be understood that the disclosure of the invention in this specification includes all possible combinations of such particular features. For example, where a particular feature is disclosed in the context of a particular aspect or embodiment of the invention, or a particular claim, that feature can also be used, to the extent possible, in combination with and/or in the context of other particular aspects and embodiments of the invention, and in the invention generally.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The present invention provides methods and kits for detection, sequence determination, and/or quantification of RNAs. Specifically, the disclosed methods are suitable for the detection and quantification of small RNA, and more specifically for RNA molecules of about 6 to 36 nucleotides in length.

In a preferred embodiment, the present invention provides a method for detecting, treating, or preparing an RNA sample, the method comprising:
  (a) obtaining a sample containing RNA molecules;
  (b) masking ribosomal RNA molecules by providing one or more oligonucleotide(s) complementary to the RNA to be masked;
  (c) ligating a 3' oligonucleotide adaptor to the 3' end of small RNA molecules;
  (d) hybridizing one or more reverse transcription (RT) primer oligonucleotide(s) to both the free and the ligated form of said 3' oligonucleotide adaptor;
  (e) removing the free 3' oligonucleotide adaptor/RT primer-dimer by enzymatic digest;
  (f) ligating a 5' oligonucleotide adaptor to the 5' end of said small RNA molecules;
  (g) performing reverse transcription of the RNA; and
  (h) performing one PCR reaction with RT primer and RP1 primer and a second PCR with RP1 and indexed primers.

I. Methods of Analyzing RNA

In some embodiments, the oligonucleotides, RNA masks, adaptors, and primers contemplated by this invention may contain structural modifications such as atoms, moieties, residues, polymers, or labels. Specifically, said oligonucleotides, RNA masks, adaptors, and primers may incorporate a detectable label, isotopes, radiolabels such as $^{32}$P, binding moieties such as biotin, haptens such as dioxygenin, luminogenic, mass tags, phosphorescent or fluorescent moieties, fluorescent dyes, and the like.

In other embodiments of the invention, oligonucleotides, RNA masks, adaptors, and primers may incorporate nucleoside or nucleotide analogs that are rarely present in natural nucleic acids, including, but not limited to, inverted nucleotides, dideoxy nucleotides, abasic sugar phosphates, inosine (hypoxanthine), 5-bromouracil, 5-methylcytosine, 5-iodouracil, 2-aminoadenosine, 6-methyladenosine, preudouridine, deoxyinosine, 2,6-diamino-4-hydroxy-5-formamidopyrimidine (foramidopyrimidine-guanine, (fapy)-guanine), 8-oxoadenine, 1,N6-ethenoadenine, 3-methyladenine, 4,6-diamino-5-formamidopyrimidine, 5,6-dihydrothymine, 5,6-dihydroxyuracil, 5-formyluracil, 5-hydroxy-5-methylhydanton, 5-hydroxycytosine, 5-hydroxymethylcysto sine, 5-hydroxymethyluracil, 5-hydroxyuracil, 6-hydroxy-5,6-dihydrothymine, 6-methyladenine, 7,8-dihydro-8-oxoguanine (8-oxoguanine), 7-methylguanine, aflatoxin Bl-fapy-guanine, fapy-adenine, hypoxanthine, methyl-fapy-guanine, methyltartonylurea, thymine glycol, and the like.

In certain embodiments, oligonucleotides, RNA masks, adaptors, and primers contemplated by the invention may also include a 5' modification, such as an inverted base (e.g. 5'-5' linkage) or one or more phosphorothioate bonds to prevent 5'-3' exonuclease-degradation or unwanted ligation products.

In certain embodiments, the sequence of the RNA mask is selected from the list of sequences provided in Table 1. In a preferred embodiment, the RNA mask has the sequence set forth in SEQ ID NO: 1. In certain embodiments, one or both of the ends of the RNA mask is blocked with a chemical group, including, but not limited to, biotin, amino group, inverted nucleotides, dideoxy nucleotides, spacers, dyes, digoxigenin, cholesterol, and phosphate.

In certain embodiments, the ligase used to join two nucleic acid molecules is selected from the group consisting of T4 ligase, T4 ligase 2 truncated KQ, T7 ligase, and Taq ligase.

In certain embodiments, the sequence of the 3' oligonucleotide adaptor is rAppTGGAATTCTCGGGTGCCAAGG-ddC (SEQ ID NO: 82). "rApp" stands for 5' adenylation and "ddC" is a dideoxycytidine at the 3' end.

In certain embodiments, the sequence of the RT primer is selected from the list of sequences provided in Table 2. In a preferred embodiment, the RT primer has the sequence set forth in SEQ ID NO: 12. In certain embodiments, the 5' end of the RT primer is blocked with a chemical group, including, but not limited to, biotin, amino group, inverted nucleotides, dideoxy nucleotides, spacers, dyes, digoxigenin, cholesterol, and phosphate.

In certain embodiments, the enzyme(s) for the digestion of the 3' oligonucleotide adaptor/RT primer-dimer are selected from the list provided in Table 3. In a preferred embodiment, the enzymes used are 5' deadenylase and Lambda exonuclease.

In certain embodiments, the sequence of the 5' oligonucleotide adaptor is selected from the list of sequences provided in Table 4. In a preferred embodiment, the 5' oligonucleotide adaptor has the sequence set forth in SEQ ID NO: 17. In certain embodiments, the 5' adaptor contains UMIs (Kivioja et al. *Nat. Methods* 9, 72-74 (2012)) to counter PCR stochasticity (Kebschull and Zador. *Nucleic Acids Res.* 43, e143-e143 (2015)) and to allow counting of RNA molecules. The unique identifying sequences can also be used within a quality assurance protocol, including use as a means for tracking samples through multiple reactions, personnel or processing locations.

In a certain embodiment, the first PCR after the reverse transcription is carried out using two primers, wherein one primer is said RT primer and the other primer is primer RP1, which has the sequence:

(SEQ ID NO: 83)
AATGATACGGCGACCACCGAGATCTACACGTTCAGAGTTCTACAGTCCGA.

In certain embodiments, the indexed primers for the second PCR are selected from the list of sequences provided in Table 5.

TABLE 1

RNA masks. "biotin" and "TEG-biotin" refer to an attached biotin group that can have a tetra-ethyleneglycol (TEG) spacer. "Inverted" refers to inverted nucleotides. "6-Aminolink" refers to a terminal amino group ($NH_2$) bound to a linker with six carbons.

| SEQ ID NO: | Sequence |
|---|---|
| 1 | ATCGGCAAGCGACGCTCAGACAGGCGTAGCCCCGGGAGGAACCCGGGGCCGCAAGTGCGTTCGAAGTGTCGATGAT-TEG-biotin |
| 2 | GGC GAA GCC C + AACCGACGCTCAGACAGGC-$NH_2$ |
| 3 | GGC GAA GCC AAGCGACGCTCAGACAGGCGTAGCCCCGGGAGGAACCCG-$NH_2$ |
| 4 | GGC GAA GCC AAGCGACGCTCAGACAGGCGTAGC-biotin-TEG |
| 5 | AAA AGC GAC GCT CAG ACA GGC-inverted |
| 6 | $NH_2$-GGCGAAGCCAAGCGACGCTCAGACAGGCGTAGCCCCGGGAGGAACCCGGGGCCGCAAGTGCGTTCGAAGTGTCGATGATCAATGTGGC GAAGCC |
| 7 | $NH_2$-GGCGAAGCCGTCCTGCAATTCACATTAATTCTCGCAGCTAGCTGCGTTCTTCATCGACGCACGAGCCGAGTGATCCACCGCTAAGAGTCGGC GAAGCC |
| 8 | GCATCGGCAAGCGACGCTCAGACAGGCGTAGCCCCGGGAGGAACCCGGGGCCGCAAGTGCGTTCGAAGTGTCGATG |
| 9 | ATCGGCAAGCGACGCTCAGACAGGCGTAGCCCCGGGAGGAACCCGGGGCCGCAAGTGCGTTCGAAGTGTCGATGATCAATGTGTCCTGCAATTCACATTAATTCTCGCAGCTAGCTGCGTTCTTCATCGACGCACGAGCCGAGTGATCCACCGCTAAGAGTCGTACGAGG |
| 10 | 6-Aminolink-ATCGGCAAGCGACGCTCAGACAGGCGTAGCC-TEG-biotin |
| 11 | 6-Aminolink-CGAGTGATCCACCGCTAAGAGTCGTACGAGG-TEG-biotin |

TABLE 2

RT primers. "biotin" and "TEG-biotin" refers to an attached biotin group that can have a TEG spacer.

| SEQ ID NO: | Sequence |
|---|---|
| 12 | biotin-CCTTGGCACCCGAGAATTCCrA |
| 13 | ACCCGAGAATTCCAATTGATGGTGCCTACAG |
| 14 | CCTTGGCACCCGAGAATTCC |
| 15 | biotin-CCTTGGCACCCGAGAATTCC |
| 16 | biotin-GCCTTGGCACCCGAGAATTCCA |

TABLE 3

Enzymes for the digest of 3' oligonucleotide adaptor/RT primer - dimers.

Enzyme

5' deadenylase
Lambda exonuclease
Exonuclease I
RecJf nuclease

TABLE 4

5' adaptor sequences. "$NH_2$" refers to an amino linker and "rN" refers to ribo-nucleotides. "rH" refers to the combination of three ribo-nucleotides of rA, rU and rC. Eight rH ribo-nucleotides were designed to provide UMIs (Unique Molecular Identifier). The sequence "rCrA" was used as spacer between UMI and small RNA sequences.

| SEQ ID NO: | Sequence |
|---|---|
| 17 | $NH_2$-rGrUrUrCrArGrArGrUrUrCrUrArCrArGrUrCrCrGrArCrGrArUrCrHrHrHrHrHrHrHrHrCrA |
| 18 | $NH_2$-GUUCAGAGUUCUACAGUCCGACGAUCNNNNNNNCA |
| 19 | $NH_2$-GUUCAGAGUUCUACAGUCCGACGAUCVVVVVVVVCA |
| 20 | $NH_2$-GUUCAGAGUUCUACAGUCCGACGAUCHHHHHHHHHHCA |
| 21 | $NH_2$-GTTCAGAGTTCTACAGTCCGACGATCHHHrHrHrHrHrCrA |
| 22 | $NH_2$-GTTCAGAGTTCTACAGTCCGACGATCHHHHHrHrHrHrCrA |
| 23 | $NH_2$-GUU CAG AGU UCU ACA GUC CGA CGA UCR DDD DDD GAG A |
| 24 | $NH_2$-GUUCAGAGUUCUACAGUCCGACGAUCVVVVVVVVCA |
| 25 | $NH_2$-GUUCAGAGUUCUACAGUCCGACGAUCVVVVVVVV |
| 26 | $NH_2$-CCUUGGCACCCGAGUUCUACAGUCCGACGAUC H |
| 27 | $NH_2$-CCUUGGCACCCGAGUUCUACAGUCCGACGAUC H HHH HHH HHH CA |
| 28 | $NH_2$-GUUCAGAGUUCUACAGUCCGACGAUCHHHAHHHCA |
| 29 | $NH_2$-GUUCAGAGUUCUACAGUCCGACGAUCHHHUHHHCA |
| 30 | $NH_2$-GUUCAGAGUUCUACAGUCCGACGAUCHHHHHHCA |
| 31 | $NH_2$-GUUCAGAGUUCUACAGUCCGACGAUCVVVAVVVCA |
| 32 | $NH_2$-GUUCAGAGUUCUACAGUCCGACGAUCVVVCVVVCA |
| 33 | $NH_2$-GUUCAGAGUUCUACAGUCCGACGAUCVVVVVVCA |

TABLE 5

Index primers.

| SEQ ID NO: | Sequence |
|---|---|
| 34 | CAAGCAGAAGACGGCATACGAGATCGTGATGTGACTGGAGTTCCTTGGCACCCGAGAATTCCA |
| 35 | CAAGCAGAAGACGGCATACGAGATACATCGGTGACTGGAGTTCCTTGGCACCCGAGAATTCCA |
| 36 | CAAGCAGAAGACGGCATACGAGATGCCTAAGTGACTGGAGTTCCTTGGCACCCGAGAATTCCA |
| 37 | CAAGCAGAAGACGGCATACGAGATTGGTCAGTGACTGGAGTTCCTTGGCACCCGAGAATTCCA |
| 38 | CAAGCAGAAGACGGCATACGAGATCACTGTGTGACTGGAGTTCCTTGGCACCCGAGAATTCCA |
| 39 | CAAGCAGAAGACGGCATACGAGATATTGGCGTGACTGGAGTTCCTTGGCACCCGAGAATTCCA |
| 40 | CAAGCAGAAGACGGCATACGAGATGATCTGGTGACTGGAGTTCCTTGGCACCCGAGAATTCCA |
| 41 | CAAGCAGAAGACGGCATACGAGATTCAAGTGTGACTGGAGTTCCTTGGCACCCGAGAATTCCA |
| 42 | CAAGCAGAAGACGGCATACGAGATCTGATCGTGACTGGAGTTCCTTGGCACCCGAGAATTCCA |
| 43 | CAAGCAGAAGACGGCATACGAGATAAGCTAGTGACTGGAGTTCCTTGGCACCCGAGAATTCCA |
| 44 | CAAGCAGAAGACGGCATACGAGATGTAGCCGTGACTGGAGTTCCTTGGCACCCGAGAATTCCA |
| 45 | CAAGCAGAAGACGGCATACGAGATTACAAGGTGACTGGAGTTCCTTGGCACCCGAGAATTCCA |
| 46 | CAAGCAGAAGACGGCATACGAGATTTGACTGTGACTGGAGTTCCTTGGCACCCGAGAATTCCA |
| 47 | CAAGCAGAAGACGGCATACGAGATGGAACTGTGACTGGAGTTCCTTGGCACCCGAGAATTCCA |
| 48 | CAAGCAGAAGACGGCATACGAGATTGACATGTGACTGGAGTTCCTTGGCACCCGAGAATTCCA |
| 49 | CAAGCAGAAGACGGCATACGAGATGGACGGGTGACTGGAGTTCCTTGGCACCCGAGAATTCCA |
| 50 | CAAGCAGAAGACGGCATACGAGATCTCTACGTGACTGGAGTTCCTTGGCACCCGAGAATTCCA |
| 51 | CAAGCAGAAGACGGCATACGAGATGCGGACGTGACTGGAGTTCCTTGGCACCCGAGAATTCCA |
| 52 | CAAGCAGAAGACGGCATACGAGATTTTCACGTGACTGGAGTTCCTTGGCACCCGAGAATTCCA |
| 53 | CAAGCAGAAGACGGCATACGAGATGGCCACGTGACTGGAGTTCCTTGGCACCCGAGAATTCCA |
| 54 | CAAGCAGAAGACGGCATACGAGATCGAAACGTGACTGGAGTTCCTTGGCACCCGAGAATTCCA |
| 55 | CAAGCAGAAGACGGCATACGAGATCGTACGGTGACTGGAGTTCCTTGGCACCCGAGAATTCCA |
| 56 | CAAGCAGAAGACGGCATACGAGATCCACTCGTGACTGGAGTTCCTTGGCACCCGAGAATTCCA |
| 57 | CAAGCAGAAGACGGCATACGAGATGCTACCGTGACTGGAGTTCCTTGGCACCCGAGAATTCCA |
| 58 | CAAGCAGAAGACGGCATACGAGATATCAGTGTGACTGGAGTTCCTTGGCACCCGAGAATTCCA |
| 59 | CAAGCAGAAGACGGCATACGAGATGCTCATGTGACTGGAGTTCCTTGGCACCCGAGAATTCCA |
| 60 | CAAGCAGAAGACGGCATACGAGATAGGAATGTGACTGGAGTTCCTTGGCACCCGAGAATTCCA |
| 61 | CAAGCAGAAGACGGCATACGAGATCTTTTGGTGACTGGAGTTCCTTGGCACCCGAGAATTCCA |
| 62 | CAAGCAGAAGACGGCATACGAGATTAGTTGGTGACTGGAGTTCCTTGGCACCCGAGAATTCCA |
| 63 | CAAGCAGAAGACGGCATACGAGATCCGGTGGTGACTGGAGTTCCTTGGCACCCGAGAATTCCA |
| 64 | CAAGCAGAAGACGGCATACGAGATATCGTGGTGACTGGAGTTCCTTGGCACCCGAGAATTCCA |
| 65 | CAAGCAGAAGACGGCATACGAGATTGAGTGGTGACTGGAGTTCCTTGGCACCCGAGAATTCCA |
| 66 | CAAGCAGAAGACGGCATACGAGATCGCCTGGTGACTGGAGTTCCTTGGCACCCGAGAATTCCA |
| 67 | CAAGCAGAAGACGGCATACGAGATGCCATGGTGACTGGAGTTCCTTGGCACCCGAGAATTCCA |
| 68 | CAAGCAGAAGACGGCATACGAGATAAAATGGTGACTGGAGTTCCTTGGCACCCGAGAATTCCA |
| 69 | CAAGCAGAAGACGGCATACGAGATTGTTGGGTGACTGGAGTTCCTTG |
| 70 | CAAGCAGAAGACGGCATACGAGATATTCCGGTGACTGGAGTTCCTTGGCACCCGAGAATTCCA |

TABLE 5-continued

Index primers.

| SEQ ID NO: | Sequence |
|---|---|
| 71 | CAAGCAGAAGACGGCATACGAGATAGCTAGGTGACTGGAGTTCCTTGGCACCCGAGAATTCCA |
| 72 | CAAGCAGAAGACGGCATACGAGATGTATAGGTGACTGGAGTTCCTTGGCACCCGAGAATTCCA |
| 73 | CAAGCAGAAGACGGCATACGAGATTCTGAGGTGACTGGAGTTCCTTGGCACCCGAGAATTCCA |
| 74 | CAAGCAGAAGACGGCATACGAGATGTCGTCGTGACTGGAGTTCCTTGGCACCCGAGAATTCCA |
| 75 | CAAGCAGAAGACGGCATACGAGATCGATTAGTGACTGGAGTTCCTTGGCACCCGAGAATTCCA |
| 76 | CAAGCAGAAGACGGCATACGAGATGCTGTAGTGACTGGAGTTCCTTGGCACCCGAGAATTCCA |
| 77 | CAAGCAGAAGACGGCATACGAGATATTATAGTGACTGGAGTTCCTTGGCACCCGAGAATTCCA |
| 78 | CAAGCAGAAGACGGCATACGAGATGAATGAGTGACTGGAGTTCCTTGGCACCCGAGAATTCCA |
| 79 | CAAGCAGAAGACGGCATACGAGATTCGGAGTGACTGGAGTTCCTTGGCACCCGAGAATTCCA |
| 80 | CAAGCAGAAGACGGCATACGAGATCTTCGAGTGACTGGAGTTCCTTGGCACCCGAGAATTCCA |
| 81 | CAAGCAGAAGACGGCATACGAGATTGCCGAGTGACTGGAGTTCCTTGGCACCCGAGAATTCCA |

II. Methods of Sequencing RNA

The methods of the invention are not limited to any particular sequencing method. Sequencing of individual molecules or clonal populations can be carried out using known methods such as Sanger sequencing or next generation sequencing. Non-limiting examples for sequencing methods contemplated by the invention include, but are not limited to, fluorescent in situ sequencing, massively parallel signature sequencing, pyrosequencing, ion semiconductor sequencing, polony sequencing, sequencing by ligation, DNA nanoball sequencing, sequencing by ligation, or single molecule sequencing.

III. Sample Preparation

Suitable samples that provide target RNA molecules may comprise a wide range of eukaryotic and prokaryotic cells, including animal cells, tissue culture animal cells, plant cells, cells sensitive to osmotic shock, cells of bacteria, yeasts, viruses, mycoplasmas, protozoa, rickettsia, fungi and other small microbial cells and the like, as well as protoplasts. Samples contemplated by the invention include liquids containing single or multiple cells, liquids containing organelles, fluidized tissues, fluidized organisms, and liquids containing multi-celled organisms. The methods contemplated by the invention are applicable to any type of biological sample (including blood, serum, plasma, reticulocytes, lymphocytes, any product prepared from blood or lymph, bone marrow tissue, cerebrospinal fluid, sweat, tear, saliva, sputum, amniotic fluid, seminal fluid, vaginal excretion, serous fluid, synovial fluid, pericardial fluid, peritoneal fluid, pleural fluid, transudates, exudates, cystic fluid, bile, urine, gastric fluid, intestinal fluid, or fecal samples), any type of tissue biopsy (e.g. a tumor biopsy, a muscle biopsy, a liver biopsy, a kidney biopsy, a bladder biopsy, a bone biopsy, a cartilage biopsy, a skin biopsy, a pancreas biopsy, a biopsy of the intestinal tract, a thymus biopsy, a uterus biopsy, a testicular biopsy, an eye biopsy or a brain biopsy), or any other biological material that may harbor RNA molecules. Suitable samples further comprise clinical samples (which are samples provided by a patient), biological swabs and biological washes. Alternatively, RNA provided in the sample may be recombinant, such that it is obtained from a cell-free system or reaction mixture or from a recombinant host cell, which may or may not have endogenous small RNA. RNA molecules may further be derived from conditioned medium resulting from the growth of one or more cells in cell culture medium.

The methods of the invention are not limited to any particular method of sample preparation. In certain instances, total RNA is first isolated from the sample and then the small RNA is separated from the other RNA, thereby enriching for small RNA. In some embodiments, the small RNA has been isolated away from other RNA to enrich for the small RNA, such that the small RNA is substantially pure, meaning it is at least about 80%, 85%, 90%, 95% pure or more, but less than 100% pure, with respect to other RNA molecules. Methods for isolating RNA molecules are well known in the art and include, but are not limited to, isolation of RNA molecules by acrylamide, agarose or other suitable gels and isolation by PAGE fractionation. Various kits for the extraction of RNA from biological samples are available commercially.

IV. Applications of the Invention

In one aspect, the present invention provides methods for obtaining information about the relative abundance information of a particular RNA sequence in a given sample. Relative abundance can be determined by counting the frequency of observance for a specific RNA sequence. This allows the sRNAs to be ranked by their relative abundance within the tissue, for example, to discover high or low abundance molecules. This discloses sequences that have a particular association with a characteristic of the source of the RNA. For example, sequences that have a high relative abundance in a disease-state sample compared with a non-diseased-state sample are associated with the disease response. An absolute measure of abundance may be preferred over a relative quantitation of RNA expression (e.g. by providing an expression ratio for a given RNA compared to a housekeeping or normalizing RNA/gene). Absolute abundance measurements may facilitate comparison of small RNA abundances between samples and between experiments, and may allow "banking" of data from different runs in a database and direct comparison of the banked data.

In another aspect, the present invention provides methods for determining the relative expression of small RNA molecules in different samples. This can, for example, be achieved by sequencing small RNA molecules from a first sample and a second sample, and then comparing the sequencing data of the small RNA molecules isolated from the first and the second samples. This will identify molecules with differential frequencies in the two samples. In some embodiments of the invention, the differentially expressed RNA molecules will be biomarkers, that is, biochemical features or facets that pertain to a subject and can be used to measure the presence, progression and/or regression of a disease and/or the effect of a treatment. When compared to a reference level, the expression level of biomarkers described herein can be correlative to a subject's disease state. Accordingly, biomarkers can be indicative of a diseased or healthy state of a subject. Thus, in one embodiment, similar expression of small RNA in a sample from a subject relative to the reference level indicates the absence of a disease or medical condition in the subject. In another embodiment, a difference in the expression of small RNA in a sample from a subject relative to the reference level indicates the presence or severity of the disease or medical condition in the subject. In yet another embodiment of the invention small RNA expression can be compared to a reference level at different times to monitor disease progression or regression. As such, methods contemplated by the invention may be used to evaluate differences between hyperplasia, neoplasia, pre-cancer, and cancer, or between a primary tumor and a metastasized tumor. Further, methods of this invention can be used to identify cells and subjects at risk of developing a disease.

In some embodiments, methods of the invention are used to detect RNA associated with infectious disease, including RNA viruses such as human immunodeficiency virus, hepatitis C virus, and other microbes.

In some embodiments, the invention can be used to characterize sRNAs from various cell types. Embodiments of the invention further allow the differentiation of individual cell types on the single cell level. This paves the way for using small RNA-sequencing to decode cell heterogeneity in complex samples such as complex tissues and organs like the brain or the blood system. The invention can further aid in the discovery of cell sub-populations based on small RNA profiles.

In another embodiment, the invention can be used for the study of cellular heterogeneity in pathological conditions such as tumors and can aid in decoding the heterogeneity of tumor tissues. A previous microarray-based study found that global miRNAs profiling was more effective in classifying poorly differentiated tumors than mRNA profiling did, however, the experiment was done on bulk RNA extracted from whole cancerous tissue (Lu et al. *Nature* 435, 834-838 (2005)).

In another embodiment, the invention may serve the discovery of rare cells based on small RNA profiles or may be used to study the dynamics of small RNA expression and expression noise or post-transcriptional regulations by silencing sRNAs in single cells.

IV. Kits

Reagents employed in the disclosed methods can be packaged into diagnostic or prognostic kits.

In some embodiments, the kit comprises one or more oligonucleotide(s) for masking ribosomal RNA molecules. In a preferred embodiment, the RNA masking oligonucleotides provided in the kit have sequences selected from the list of sequences provided in Table 1. In the most preferred embodiment, the RNA mask provided by the kit has the sequence set forth in SEQ ID NO: 1.

In some embodiments, the kit comprises one or more 3' oligonucleotide adaptors for the ligation to the 3' end of small RNA molecules. In a preferred embodiment, the sequence of the 3' oligonucleotide adaptor provided in the kit is (SEQ ID NO: 82)
rAppTGGAATTCTCGGGTGCCAAGG-ddC.

In some embodiments, the kit comprises one or more reverse transcription (RT) primer oligonucleotide(s). In a preferred embodiment, the RT primer oligonucleotides provided in the kit have sequences selected from the list of sequences provided in Table 2. In the most preferred embodiment, the RT primer has the sequence set forth in SEQ ID NO: 12.

In some embodiments, the kit comprises one or more 5' oligonucleotide adaptor(s). In a preferred embodiment, the 5' oligonucleotide adaptors provided by the kit have sequences selected from the list of sequences provided in Table 4. In the most preferred embodiment, the 5' oligonucleotide adaptor has the sequence set forth in SEQ ID NO: 17. In some embodiments, the 5' oligonucleotide adaptors provided by the kit contain UMIs.

In some embodiments, the kit comprises primers for the first PCR after the reverse transcription, wherein one primer is primer RP1, which has the sequence (SEQ ID NO: 83)
AATGATACGGCGACCACCGAGATCTACACGTTCAGAGTTCTACAGTCCGA.

In some embodiments, the kit comprises one or more indexed primer(s) for the second PCR after the reverse transcription, wherein said primers have sequences selected from the list of sequences provided in Table 5.

The kits contemplated by the invention can also contain other suitably packaged reagents and materials needed for performing the methods contemplated by the invention. Non-limiting examples for such reagents and materials are (1) one or more enzyme(s) for the digestion of 3' oligonucleotide adaptor/RT primer-dimer(s) (including the enzymes provided in Table 3), (2) reagent(s) for reverse transcription (including reverse transcriptase(s) and reverse transcriptase buffer(s)), (3) reagent(s) for amplification of RNA and/or DNA (including polymerase(s) and polymerase buffer(s)), (4) nuclease-free water, (5) buffer(s), (6) dNTPs and/or NTPs, (7) control RNA template(s), (8) RNase-free containers, such as tubes or plates, (9) nuclease inhibitor(s), and/or other reagents. In some embodiments, kits include one or more of the following (consistent with methods, reagents, and compositions discussed above): components for sample purification, including a lysis buffer with a chaotropic agent, a glass-fiber filter or column, an elution buffer, a wash buffer, an alcohol solution, and a nuclease inhibitor.

The components of the kits may be packaged either in aqueous media or in lyophilized form, for example, and will be provided in a suitable container. The components of the kit may be provided as dried powder(s). When reagents and/or components are provided as a dry powder, the powder can be reconstituted by the addition of a suitable solvent. It is envisioned that the solvent may also be provided in another container. The container will generally include at least one vial, test tube, flask, bottle, syringe, and/or other container means, into which the solvent is placed, optionally aliquoted. The kits may also comprise a second container means for containing a sterile, pharmaceutically acceptable buffer and/or other solvent.

In other aspects, the present invention also encompasses any and all reasonable workable combinations of any two or more embodiments disclosed herein. Such combinations may comprise those of all or selected elements of one embodiment with all or selected elements of any other one or more embodiment(s).

EXAMPLES

The following examples are given for the purpose of illustrating various embodiments of the invention and are not meant to limit the present invention in any fashion. Changes therein and other uses which are encompassed within the spirit of the invention as defined by the scope of the claims will occur to those skilled in the art.

Example 1: sRNA Library Preparation and Sequencing

Cells

HEK293T and glioblastoma cells (U87, KS4, JM3, JM4) were mycoplasma tested.

Naïve Stem Cell Culture

Human ESC line WA09 (female) (WiCell, Madison, Wis.) was transitioned from conventional primed conditions to 5iAF naïve state by closely following the conversion protocol described in Theunissen et al., Cell Stem Cell 15, 471-487 (2014). Naïve hESCs were maintained and expanded in a medium containing 50:50 N2B27/Neurobasal (GIBCO) with 1 mM glutamine (Invitrogen), 1% NEAA (Invitrogen), 0.1 mM β-mercaptoethanol (Sigma), and freshly supplemented with 10 μM Y-27632 ROCKi (Stemgent), 1 μM PD0325901 MEKi (Sigma), 1 μM IM-12 GSK3i (Sigma), SB590885 BRAFi (Sigma), 1 μM WH-4-023 SRCi (Sigma), 20 ng/ml Activin A (R&D), 0.5% KOSR (Invitrogen), 8 ng/ml bFGF (R&D), 50 ug/ml BSA (Sigma), and 20 ng/ml hLIF (Millipore) (Theunissen et al., Cell Stem Cell 15, 471-487 (2014)). Cells were propagated on irradiated E12.5 MEFs (GIBCO) seeded at 250 k cells/well of a 6 well (9.5 cm2), and once colonies reached confluence they were dissociated and expanded by single cell using Accutase (GIBCO). WA09 (H9) has been mycoplasma tested and validated for pluripotency by teratoma assay (in primed state) as well as immunocytochemistry (for both naive and primed). Based on our Smart-seq2 data, our cells exhibited a transcriptional profile that was indicative of the previously reported works that we aimed to reproduce.

Primed Stem Cell Culture

Conventional primed human hESC line WA09 (WiCell, Madison, Wis.) was maintained on a layer of mouse embryonic fibroblasts (MEF), in media consisting of: DMEM: F12 (Invitrogen), 20% KSR (Invitrogen), 4 ng/ml bFGF (R&D), 2 mM glutamine (GIBCO), 0.1 mM non-essential amino acids (Invitrogen), 0.1 mM β-Mercaptoethanol (Sigma). Once colonies reached confluence they were mechanically passaged through dissociation using a 26-gauge needle (VWR).

Small RNA Library Preparation and Sequencing (FIG. 1)

Plates were pre-deposited with 3 μl of lysis buffer (0.13% Triton-X-100, 4 u recombinant RNase Inhibitor, Takara). After single cell sorting, the plates were transferred to −80° C. for long storage. After thawing the plate, 1 μl of 5.8 S rRNA masking oligo (5 pmol) was added and the whole plate was incubated at 72° C. for 20 minutes. Then, 2 μl of 3' adaptor ligation reaction was added (20 pmol 3' adaptor oligo, 8.33% PEG 8000, 50 u T4 RNA Ligase 2, truncated KQ, NEB, 0.83×T4 RNA ligase buffer, NEB, 4 u recombinant RNase Inhibitor, Takara) and reaction was incubated at 30° C. for 6 h followed by 4° C. for 10 hours. Next, 3 μl of RT primer and free adaptor removal enzymes were added (200 pmol RT primer, 2.5 u Lambda exonuclease, NEB, 10 u 5' deadenylase, NEB) and the reaction was incubated at 30° C. for 15 minutes followed by 37° C. for 15 minutes.

Next, 2 μl of 5' adaptor ligation reaction was added (45 pmol 5' adaptor oligo, 0.68 mM Tris-buffered ATP, Thermo Fisher, 4 u T4 RNA ligase, Thermo Fisher, 0.23×T4 RNA ligase buffer, NEB) and the mix was incubated at 37° C. for 1 hour. Reverse transcription reaction was performed by adding 7 μl of RT reaction (1.28×Taq DNA Polymerase PCR Buffer, Thermo Fisher, 8.33 mM DTT, 0.42 mM/each dNTP, 4 u recombinant RNase Inhibitor, 150 u Superscript II reverse transcriptase, Thermo Fisher). The PCR amplification was carried out by adding 35 μl of the reagents (0.94× Phusion HF buffer, 1 u Phusion Hot Start II DNA Polymerase, Thermo Fisher, 0.12 mM/each dNTP, 1.89 μM RP1 primer) and incubating at 98° C. for 30 seconds followed by 13 cycles of 98° C. for 10 seconds, 60° C. for 30 seconds and 72° C. for 30 seconds and a final incubation at 72° C. for 5 minutes. At last, 1 μl of the amplified product was transferred to a fresh tube and the second PCR reaction was added (2 μM indexed primers, 0.2 μM RP1 primer, 1× Phusion HF buffer, 0.5 u Phusion Hot Start II DNA Polymerase, Thermo Fisher, 0.2 mM/each dNTP) and incubating at 98° C. for 30 seconds followed by 13 cycles of 98° C. for 10 seconds, 67° C. for 30 seconds and 72° C. for 30 seconds and a final incubation at 72° C. for 5 minutes. The amplified libraries of single cells were then pooled and purified with DNA Clean & Concentrator™-5, Zymo research. All samples were sequenced 1×43 bp or 1×51 bp using Illumina®HiSeq 2500 instrument.

Example 2: Read Alignments and Gene-Expression Estimation

First, the sequence in FastQ file corresponding to UMIs were removed from sequence reads and appended to the read name (for later analyses). Adapter and polyA sequences were removed from reads using cutadapt v1.8.1, with minimum overlap between adapter and the 3' of the read set to 1 nt. Reads shorter than 18 nt after adaptor trimming were discarded. Trimmed reads were aligned to the human genome (hg38) using STAR v2.4.0 with parameters—outSAMstrandField intronMotif—outFilterMismatchNoverLmax 0.04—outFilterMatchNmin 18—outFilterScoreMinOverLread 0—outFilterMatchNminOverLread 0—alignIntronMax 1 (Dobin et al. Bioinformatics 29, 15-21 (2013)). Mismatches were not allowed within the first 25 nucleotides and allowed only 1 mismatch in the remaining part of the sequence reads (25-41 nts). Spliced alignments were disabled and hard/soft-clipping was disabled for the 5' of the read. Soft-clipping of up to 3 nts were allowed at the 3' end of the read in order to account for RNA editing and 3' tRNA modifications such as addition of CCA. Reads mapping with insertions or deletions were removed. PCR amplicons were collapsed and RNA molecules were counted using the adjacency network approach (dedup_umi.py at github.com/CGATOxford/UMI-tools), where reads with UMIs having a single Hamming distance from another UMI were collapsed. RNA molecule counts were separated into two categories based on the extent of the alignment of our sequenced read with the human genome. Reads aligning over the full sequence (41 nts) were assigned as precursor molecules, whereas reads aligning with 40 or less nts were assigned as a potential small RNA. Potential sRNAs were further scrutinized to find instances were trimmed 3' ends matched the genomic sequence after the alignment (cases where actual RNA sequence matched adapter sequence, false positive adapter trimming). Consequently, these molecules were instead assigned to the precursor RNA.

Expression was estimated for annotation transcripts in the following databases (Gencode V22, Mirbase V21 and GtR-NAdb). During the quantification procedure, molecules were hierarchical assigned to annotated biotypes in the following order: Mirbase miRNAs, tRNAs from GtRNAdb, small RNA biotypes from Gencode (such as snoRNAs, snRNAs, rRNAs etc.), and lastly the remaining of Gencode transcripts such as protein coding and lincRNAs. Molecules were counted from both intronic and exonic regions of the protein coding and lincRNAs in an attempt to capture sRNAs transcribed from these regions. A weighing approach was used to assign molecules of sequences mapping to multiple genomic location, by divided by number of annotated location the sequence aligned to. Finally, for miRNAs, molecules supporting the same miRNA that were expressed from different genomic loci (i.e. where the microRNAs gene was present in multiple genomic locations) were collapsed. Finally, libraries with fewer than one million reads (before alignment) were excluded and if the number of expressed transcripts were more than two standard deviations of the median number of expressed transcripts obtained within the cell population (to filter out potential doublets and low-quality libraries). All analyses were carried out on small RNA molecule counts (i.e. amplicon corrected values), except otherwise noted.

Example 3: Dimensionality Reduction Analysis and Sample Distance Correlation Molecule count tables were separated according to RNA biotypes. Transcripts detected in two or more cells and cells that had a Spearman correlation above 0.2 to at least one other cell were used. Principal component analysis (PCA) was used to assess the separating ability of each small RNA class. The t-distributed stochastic neighbor embedding (t-SNE; Van der Maaten and Hinton, Journal of Machine Learning. 9, 2579-2605 (2008)) was performed using the parameters perplexity=50, epoch=50, initial dimensions of 100 and maximum iteration of 1000. Hierarchical clustering was performed using log 10 transformed miRNA expression values and using complete linkage as distance measure between clusters. A pseudocount of 1 was added before log 10 conversion. Spearman correlations were calculated pairwise using the miRNAs log 10 abundance profiles from the individual cells.

Example 4: Sequencing of sRNA from Different Cell Types

First, the characteristics of the method were determined by sequencing sRNAs from individual naïve and primed hESCs. In addition, individual HEK293T cells were also sequenced to compare with bulk small-RNA sequencing. A computational pipeline was developed to assign sequenced reads to the different small RNA classes (using Gencode, mirBase and GtRNAdb), to convert reads to molecules using the adjacency method and to separate sRNAs from their precursor RNA species (FIGS. 2, 3).

Figure 2:
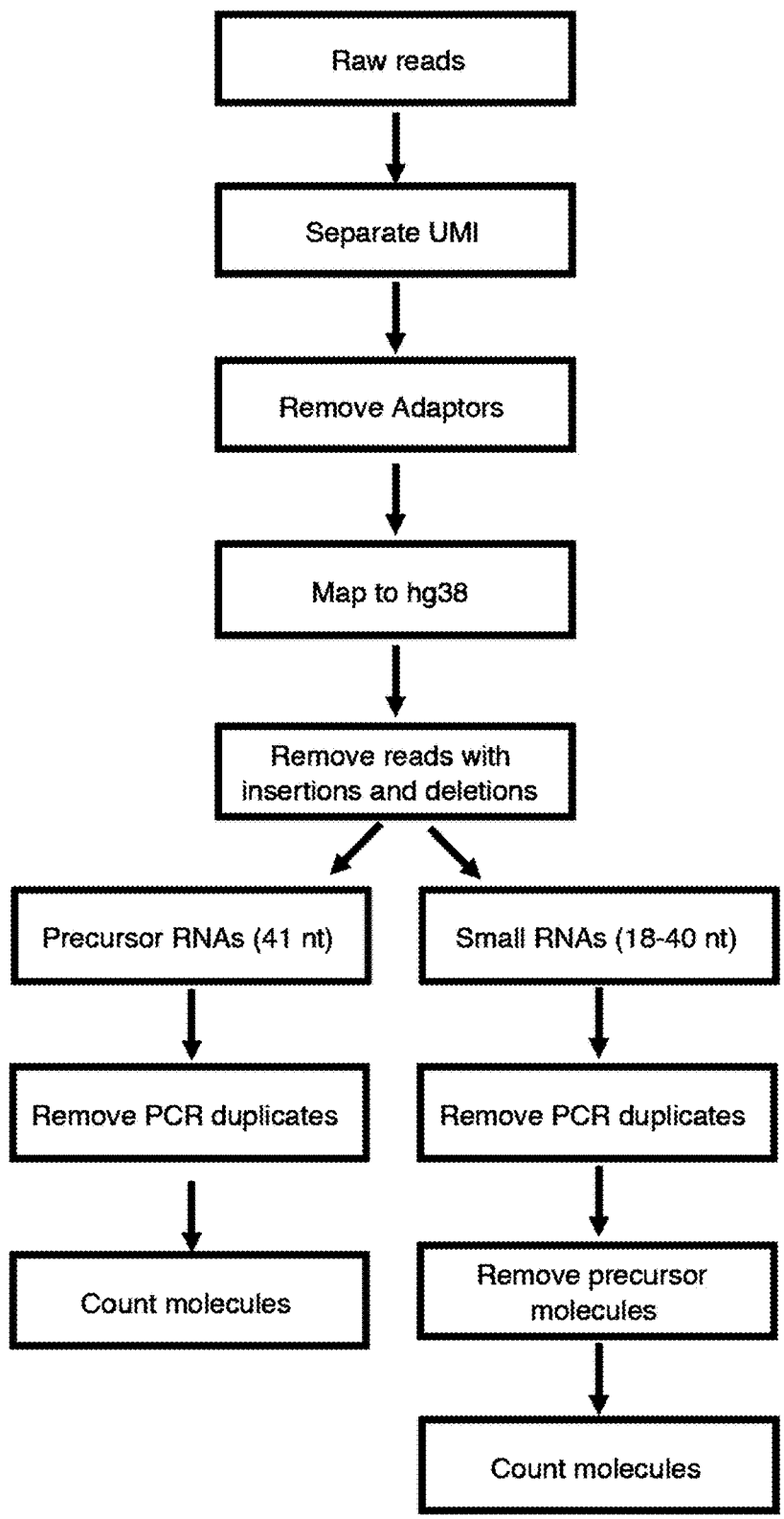
FIG. 2 illustrates a schematic diagram of the analysis pipeline for sRNA libraries.

Specifically, as illustrated in FIG. 2, Fastq files (raw reads) were obtained from Illumina sequencer, and 8 nt UMI sequence (HHHHHHHH) was removed from the beginning of the reads and added to the sequence read id. Two nt spacer sequence (CA) after UMI was also removed from 5' of the reads (Separate UMI). Adapter sequences were removed from the 3' of sequenced reads (Remove Adaptors). Minimum 1 nt overlap was required between 3' of the read and adapter sequence. End-to-end alignment was performed using STAR (allowing only soft-clipping of 3 nts at the 3' end), requiring minimum 18 nt alignment and allowing mismatch for reads 18-25 nt and 1 mismatch for 25-41 nt (Map to hg38). Then, alignments with insertions and deletions in the middle were removed (very few such reads) (Remove reads with insertions and deletions). The sequencing length was 41 nts and alignments that spanned all 41 nts (likely derived from precursor RNAs or longer RNAs) were separated from those with 18 to 40 nts alignments (small RNAs). UMIs were used to transform sequence counts into molecules, and a graph was constructed with UMIs (as nodes) and hamming distances (edges). Then, reads with 1 hamming distance were removed between two UMIs (Remove PCR duplicates), amongst the reads mapping to the same position (adjacency network method). Molecules that were 41 nt were removed but became shorter due to random match with adapter on their 3' end (i.e, fetch the genomic sequences on read 3' and match with adapter). Finally, molecules were hierarchically assigned to genes: miRNA, tRNA, snoRNA, and the rest of Gencode from the smaller transcript towards the larger. Multi mapped molecules were counted as 1/# annotated molecules for each annotated gene they match (weighed approach). The weight of molecule was not diluted due to random genomic matches without any annotation. Finally, miRNA molecule counts were collapsed when the same miRNA was expressed from different loci (i.e., having multiple copies in the genome).

Figure 3:
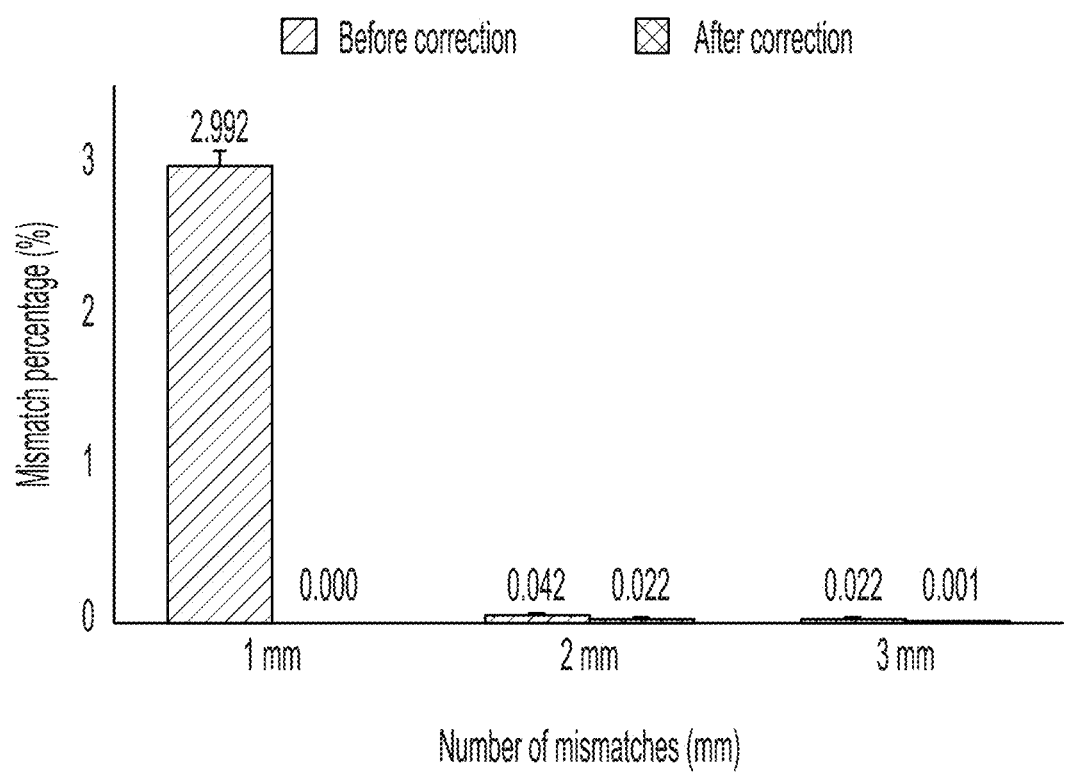
FIG. 3 illustrates estimation of sequencing errors and evaluation of the UMI correction method.

The estimation of the sequence errors and evaluation of the UMI correction method are illustrated in FIG. 3. Seven predefined UMIs with eight nucleotides length were designed. The library was prepared according to the methods of the invention and sequenced. Next, the UMIs were assigned to a single read that mapped uniquely to a coordinate. The percentage of various mismatches that occurred during PCR amplifications and sequencing reaction was calculated. Finally, the adjacency method was used to correct for the mismatched UMIs, leading to a removal of most mismatched UMI sequences. The majority of erroneous UMIs had only one mismatch and was fully removed with this procedure. Only very few UMIs had two or three mismatches and their number was also significantly reduced. The error bars denote standard deviation. The adjacency procedure is available at github.com/CGATOxford/UMI-tools.

Figure 4:
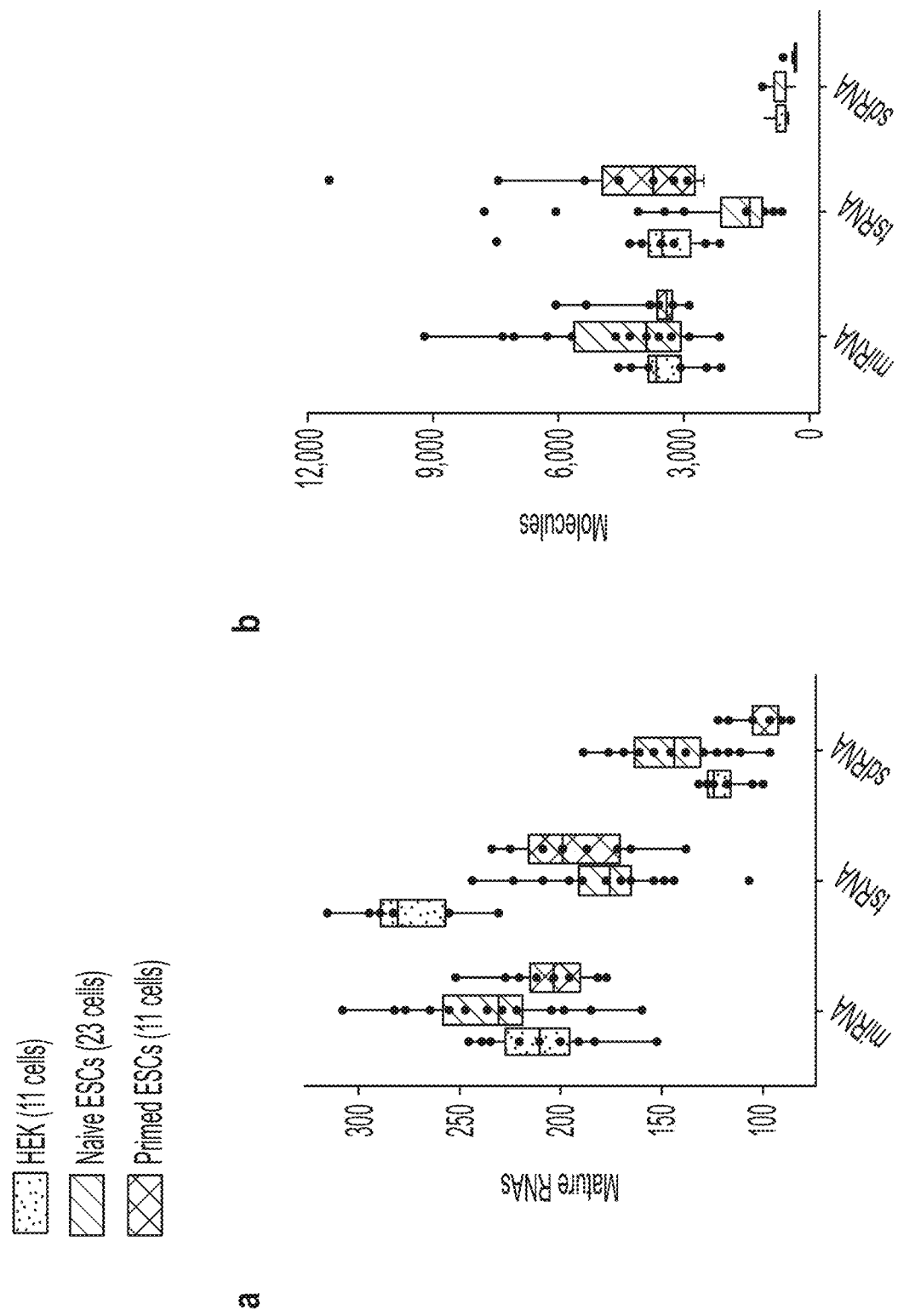
FIG. 4 illustrates small RNA diversity and characteristics in human embryonic kidney cells 293T (HEK293T) and naïve and primed human embryonic stem cells (hESCs). (a) Number of miRNAs, tsRNAs and sdRNAs detected per individual cell and cell type. (b) Absolute number of miRNAs, tsRNAs and sdRNAs molecules detected per individual cell and cell type. (c) Size distributions of sRNAs profiled in single cells and per cell type. Error bars denote standard deviations. (d) Coverage of detected small RNA across the length of the precursor RNA, shown for miRNA, tsRNA and sdRNA molecules across pre-miRNA, tRNA precursor and snoRNA, respectively. Precursor transcript length was divided into 40 bins. Data shown were from naïve hESCs. (e) Number pre-miRNAs, tRNA precursors and snoRNAs detected per individual cell and cell type. (f) Absolute number of pre-miRNAs, tRNA precursors and snoRNAs molecules per individual cell and cell type. (g) Correlation (Spearman) between the number of sRNAs and precursor expression, within individual cells and between cell types. (h) Scatter plot of miRNA molecules detected in naïve and primed hESCs (97 and 90 cells, respectively). Statistically significant genes (assessed using single cell differential expression analysis, SCDE)) with more than a 2-fold difference in molecule counts between cell types were colored red. (i) miRNA expression variation (noise) within primed and naïve hESCs (97 and 90 cells, respectively). (j) Hierarchical clustering of miRNA abundance profiles per cell, using pairwise Spearman correlations. (k) Principle component analyses of cells based on abundance profiles of sRNAs, precursor RNAs or mRNAs. Only genes expressed (1 molecule, or 1 reads per kilobase per million mapped reads (RPKM) in case of mRNA) in at least 2 samples were included.
Figure 4:
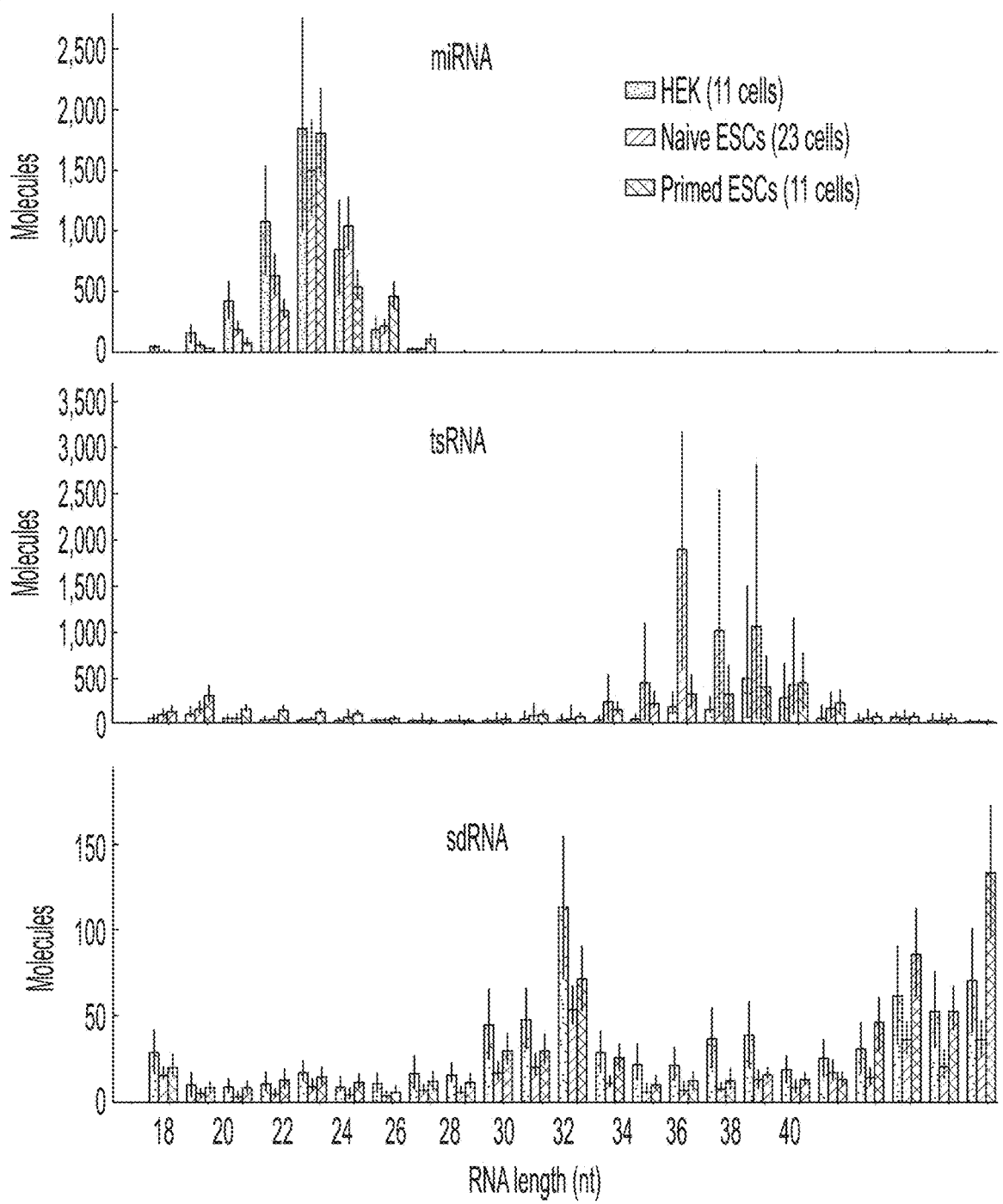
Figure 4:
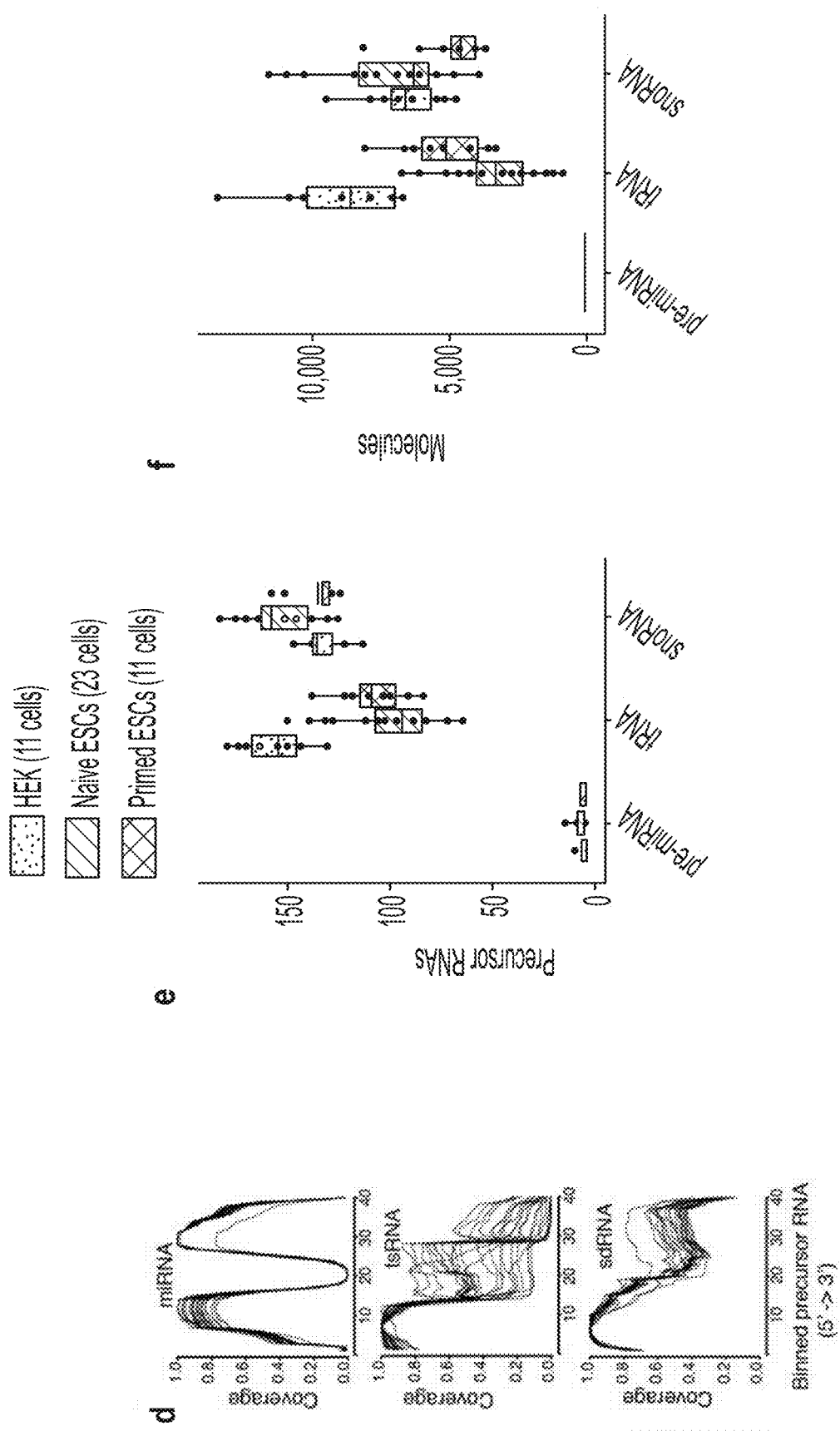
Figure 4:
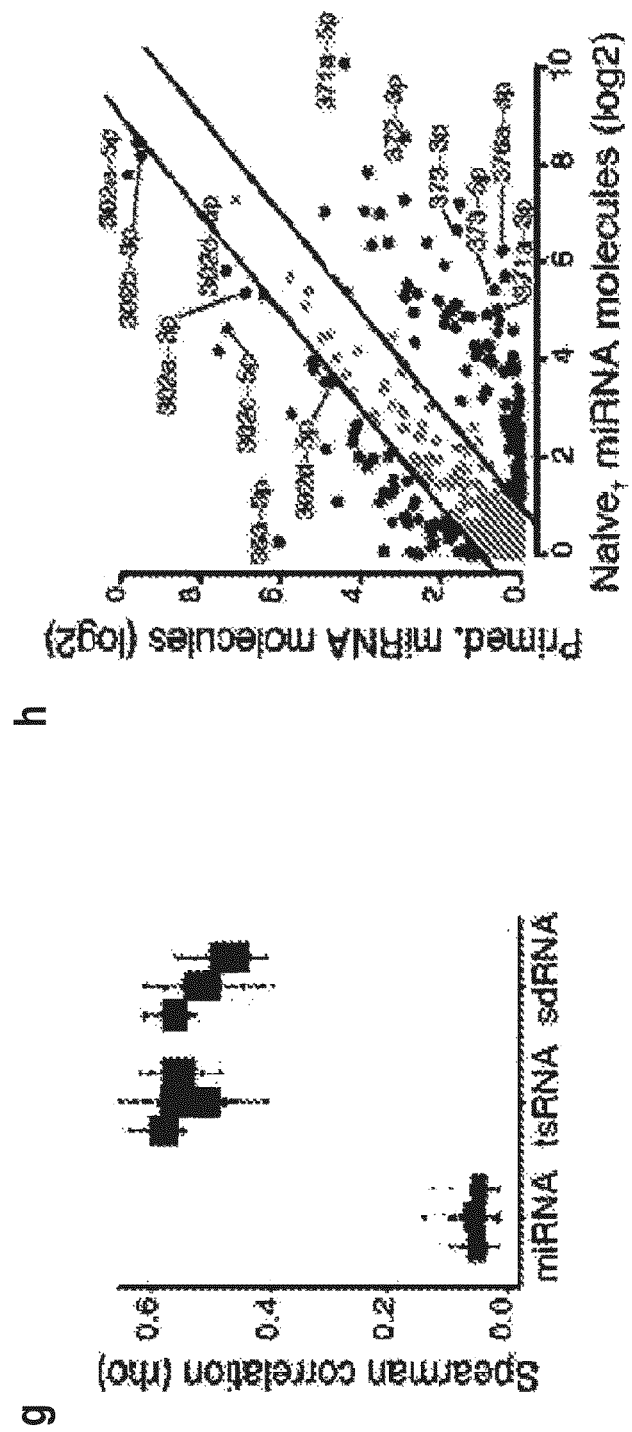
Figure 4:
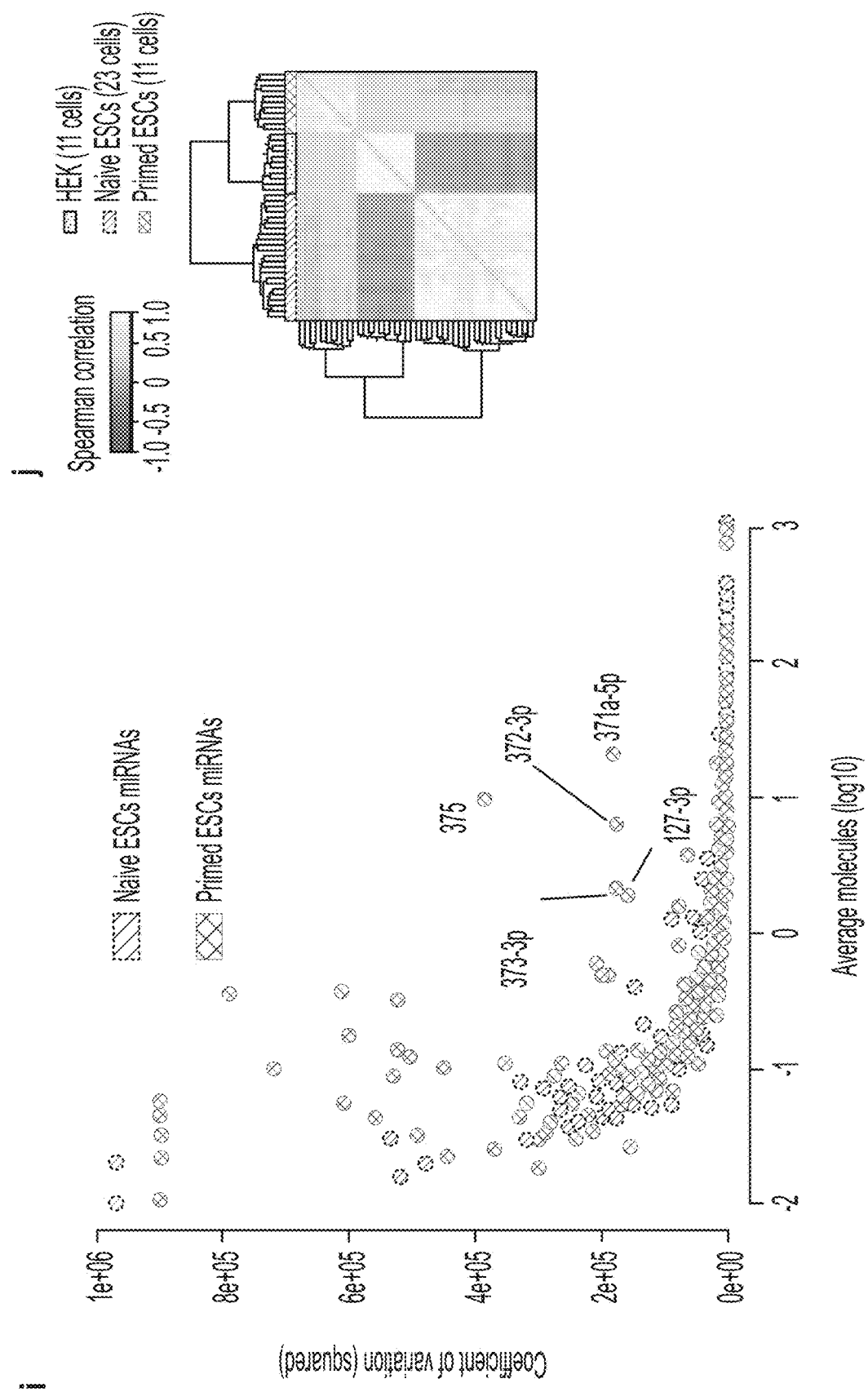
Figure 4:
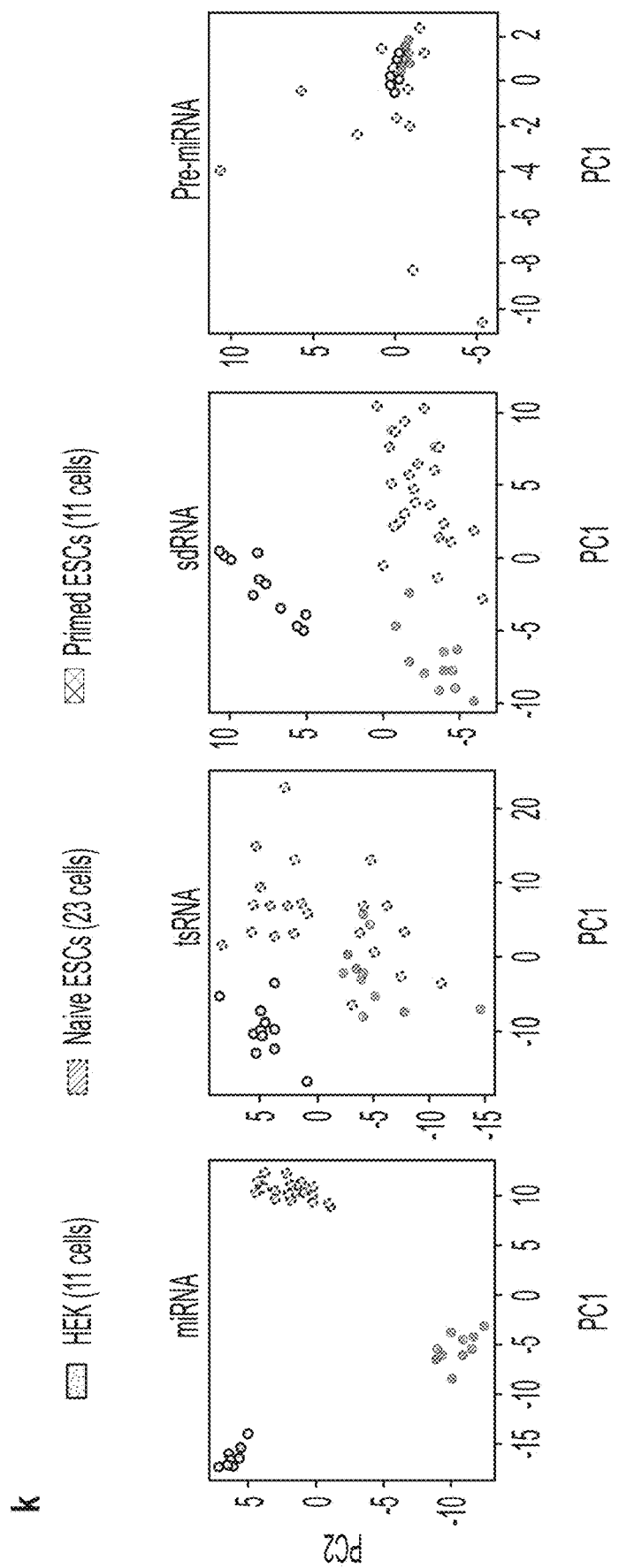

Focusing on small regulatory RNAs (18 to 40 nucleotides long), the libraries mainly contained miRNAs, sdRNAs and tsRNAs (FIG. 4a). In the average cell, 3800, 3500 and 600 molecules were captured for miRNA, tsRNA and sdRNA, respectively (FIG. 4b).

Example 5: Determination of sRNA Length Distribution

Next, the length distributions of the sRNAs were investigated and it was observed that miRNAs, as expected, were approximately 22 nts long. Specific length distributions were observed for tsRNAs (around 19 and 33 nts) and sdRNAs (around 29 nts) (FIG. 4c), suggesting the capture of processed sRNAs and not intermediate degradation products. Aligning the sRNAs to their respective precursors demonstrated, as expected, that mature miRNAs covered pre-miRNAs length in the positions corresponding to the two arms of the hairpins. Also, the other sRNAs covered distinct regions of their precursors, tsRNA molecules covered three distinct parts over the tRNA precursor body, two regions from mature tRNA, the signature of 5' and 3' tRNA halves (Fu et al. FEBS Lett. 583, 437-442 (2009)) and one region that positioned after 3' end of the mature tRNA corresponding to the tRNA-derived RNA fragment-1 (tRF-1) (FIG. 4d) (Lee et al. Genes Dev. 23, 2639-2649 (2009)). Molecules of sdRNA were biased to the 5' ends of snoRNAs. This further supported that the single-cell libraries had captured sRNAs and not random degradation products. In addition to small regulatory RNAs, the single-cell libraries contained sequence reads likely coming from longer transcripts including snoRNAs, tRNAs and to a lesser extent pre-miRNAs (FIG. 4e, f). These RNAs served as precursors for sdRNA, tsRNA and miRNA, respectively. Expression of sdRNA and tsRNA correlated moderately with the expression of their corresponding precursor transcripts (FIG. 4g), however, miRNA and pre-miRNA correlated poorly, which could be due to low number of detected pre-miRNAs, possibly a result of their secondary structures. Comparison of miRNAs in naïve and primed hESCs showed that a few miRNAs were enriched in each cell stages, notably, the mir-302 family was higher expressed in primed hESCs whereas the mir-371-3 cluster was higher expressed in naïve hESCs (FIG. 4h, Table 6). The mir-302 family was reported to regulate cell cycle and apoptosis in hESCs (Zhang et al. Stem Cell Reports 4, 645-657 (2015)) whereas, the mir-371-3 cluster was suggested to be crucial for the maintenance of hESC pluripotency (Rosa et al., Dev. Biol. 391, 81-88 (2014)) and negatively correlated with neural differentiation in human pluripotent stem cells (Kim et al. Cell Stem Cell 8, 695-706 (2011)).

TABLE 6

Significantly (adjusted p-value < 0.05 and abs(mle) > 1) differentially expressed genes from SCDE. Maximum likelihood estimate (mle) represents the log(fold change). Table is sorted by p-values.

| miRNA name | lb | mle | ub | ce | Z | cZ | p-value | adjusted p-value |
|---|---|---|---|---|---|---|---|---|
| 101-3p | −1.8753 | −1.5551 | −1.2807 | −1.2807 | −7.1608 | −7.0061 | 8.02E−13 | 2.45E−12 |
| 124-3p | −3.6134 | −2.9273 | −2.3327 | −2.3327 | −7.1608 | −7.0061 | 8.02E−13 | 2.45E−12 |
| 128-3p | −3.2932 | −2.8359 | −2.4699 | −2.4699 | −7.1608 | −7.0061 | 8.02E−13 | 2.45E−12 |
| 130a-3p | −2.4699 | −2.1955 | −2.0125 | −2.0125 | −7.1608 | −7.0061 | 8.02E−13 | 2.45E−12 |
| 130b-3p | −3.4305 | −3.0646 | −2.7444 | −2.7444 | −7.1608 | −7.0061 | 8.02E−13 | 2.45E−12 |
| 130b-5p | −3.7964 | −3.1560 | −2.6986 | −2.6986 | −7.1608 | −7.0061 | 8.02E−13 | 2.45E−12 |
| 135a-5p | −10.0170 | −8.4161 | −5.9461 | −5.9461 | −7.1608 | −7.0061 | 8.02E−13 | 2.45E−12 |
| 142-5p | −8.3246 | −6.6322 | −4.1166 | −4.1166 | −7.1608 | −7.0061 | 8.02E−13 | 2.45E−12 |
| 148b-3p | −2.2870 | −1.9211 | −1.6009 | −1.6009 | −7.1608 | −7.0061 | 8.02E−13 | 2.45E−12 |
| 151a-5p | −1.5094 | −1.2807 | −1.0520 | −1.0520 | −7.1608 | −7.0061 | 8.02E−13 | 2.45E−12 |
| 17-3p | −2.1040 | −1.6924 | −1.2807 | −1.2807 | −7.1608 | −7.0061 | 8.02E−13 | 2.45E−12 |
| 17-5p | −3.1560 | −2.6986 | −2.3327 | −2.3327 | −7.1608 | −7.0061 | 8.02E−13 | 2.45E−12 |
| 181a-5p | −3.4305 | −2.7444 | −2.1955 | −2.1955 | −7.1608 | −7.0061 | 8.02E−13 | 2.45E−12 |
| 18a-5p | −2.6986 | −2.3785 | −2.1040 | −2.1040 | −7.1608 | −7.0061 | 8.02E−13 | 2.45E−12 |
| 18b-5p | −11.0690 | −9.6053 | −6.6780 | −6.6780 | −7.1608 | −7.0061 | 8.02E−13 | 2.45E−12 |
| 1908-5p | −8.4161 | −3.5219 | −2.8816 | −2.8816 | −7.1608 | −7.0061 | 8.02E−13 | 2.45E−12 |
| 199b-5p | −3.1560 | −2.3785 | −1.7838 | −1.7838 | −7.1608 | −7.0061 | 8.02E−13 | 2.45E−12 |
| 200b-3p | −4.4367 | −3.8879 | −3.3390 | −3.3390 | −7.1608 | −7.0061 | 8.02E−13 | 2.45E−12 |
| 20b-5p | −10.1999 | −8.7363 | −5.0314 | −5.0314 | −7.1608 | −7.0061 | 8.02E−13 | 2.45E−12 |
| 221-3p | −4.5282 | −3.9336 | −3.5219 | −3.5219 | −7.1608 | −7.0061 | 8.02E−13 | 2.45E−12 |
| 224-5p | −3.0646 | −2.3785 | −1.7838 | −1.7838 | −7.1608 | −7.0061 | 8.02E−13 | 2.45E−12 |
| 28-5p | −7.3183 | −2.9273 | −2.1955 | −2.1955 | −7.1608 | −7.0061 | 8.02E−13 | 2.45E−12 |
| 302a-5p | −3.0188 | −2.8359 | −2.6986 | −2.6986 | −7.1608 | −7.0061 | 8.02E−13 | 2.45E−12 |
| 302b-5p | −1.9668 | −1.6466 | −1.3722 | −1.3722 | −7.1608 | −7.0061 | 8.02E−13 | 2.45E−12 |
| 302c-5p | −3.8421 | −3.6134 | −3.4305 | −3.4305 | −7.1608 | −7.0061 | 8.02E−13 | 2.45E−12 |
| 302d-5p | −2.2870 | −1.9211 | −1.6009 | −1.6009 | −7.1608 | −7.0061 | 8.02E−13 | 2.45E−12 |
| 30d-5p | −2.4699 | −2.1498 | −1.9211 | −1.9211 | −7.1608 | −7.0061 | 8.02E−13 | 2.45E−12 |
| 340-5p | −3.1560 | −2.6986 | −2.3327 | −2.3327 | −7.1608 | −7.0061 | 8.02E−13 | 2.45E−12 |
| 361-5p | −2.5614 | −2.1955 | −1.8296 | −1.8296 | −7.1608 | −7.0061 | 8.02E−13 | 2.45E−12 |
| 363-3p | −11.9838 | −8.2331 | −7.7300 | −7.7300 | −7.1608 | −7.0061 | 8.02E−13 | 2.45E−12 |
| 363-5p | −8.0502 | −6.4035 | −3.8879 | −3.8879 | −7.1608 | −7.0061 | 8.02E−13 | 2.45E−12 |
| 421 | −4.0251 | −3.4762 | −3.0188 | −3.0188 | −7.1608 | −7.0061 | 8.02E−13 | 2.45E−12 |
| 504-5p | −2.8816 | −2.2412 | −1.6924 | −1.6924 | −7.1608 | −7.0061 | 8.02E−13 | 2.45E−12 |
| 589-5p | −3.2018 | −2.2412 | −1.7838 | −1.7838 | −7.1608 | −7.0061 | 8.02E−13 | 2.45E−12 |
| 652-3p | −2.0583 | −1.6009 | −1.2350 | −1.2350 | −7.1608 | −7.0061 | 8.02E−13 | 2.45E−12 |
| 653-3p | −8.0502 | −6.3578 | −3.8421 | −3.8421 | −7.1608 | −7.0061 | 8.02E−13 | 2.45E−12 |
| 653-5p | −8.4161 | −6.7237 | −4.2080 | −4.2080 | −7.1608 | −7.0061 | 8.02E−13 | 2.45E−12 |
| 877-5p | −4.2080 | −3.6592 | −3.2018 | −3.2018 | −7.1608 | −7.0061 | 8.02E−13 | 2.45E−12 |
| 9-5p | −2.4242 | −1.9211 | −1.5094 | −1.5094 | −7.1608 | −7.0061 | 8.02E−13 | 2.45E−12 |
| 92a-3p | −1.9668 | −1.7381 | −1.5551 | −1.5551 | −7.1608 | −7.0061 | 8.02E−13 | 2.45E−12 |
| 92b-5p | −3.6592 | −3.1560 | −2.7901 | −2.7901 | −7.1608 | −7.0061 | 8.02E−13 | 2.45E−12 |
| 93-5p | −3.2475 | −2.9273 | −2.6072 | −2.6072 | −7.1608 | −7.0061 | 8.02E−13 | 2.45E−12 |
| 941 | −2.2870 | −1.7381 | −1.2807 | −1.2807 | −7.1608 | −7.0061 | 8.02E−13 | 2.45E−12 |
| 1185-1-3p | 2.9273 | 3.6592 | 8.2789 | 2.9273 | 7.1608 | 7.0061 | 8.02E−13 | 2.45E−12 |
| 1185-2-3p | 3.9793 | 6.4950 | 8.6905 | 3.9793 | 7.1608 | 7.0061 | 8.02E−13 | 2.45E−12 |
| 127-3p | 6.0376 | 6.4950 | 7.0439 | 6.0376 | 7.1608 | 7.0061 | 8.02E−13 | 2.45E−12 |
| 1283 | 2.6529 | 3.1103 | 3.5219 | 2.6529 | 7.1608 | 7.0061 | 8.02E−13 | 2.45E−12 |
| 1323 | 2.5614 | 2.8816 | 3.1560 | 2.5614 | 7.1608 | 7.0061 | 8.02E−13 | 2.45E−12 |
| 136-3p | 4.4825 | 5.1686 | 9.5596 | 4.4825 | 7.1608 | 7.0061 | 8.02E−13 | 2.45E−12 |

TABLE 6-continued

Significantly (adjusted p-value < 0.05 and abs(mle) > 1) differentially expressed
genes from SCDE. Maximum likelihood estimate (mle) represents the log(fold change).
Table is sorted by p-values.

| miRNA name | lb | mle | ub | ce | Z | cZ | p-value | adjusted p-value |
|---|---|---|---|---|---|---|---|---|
| 146b-5p | 4.3453 | 4.9399 | 5.5802 | 4.3453 | 7.1608 | 7.0061 | 8.02E-13 | 2.45E-12 |
| 182-5p | 1.4637 | 1.7381 | 1.9668 | 1.4637 | 7.1608 | 7.0061 | 8.02E-13 | 2.45E-12 |
| 25-5p | 2.0125 | 2.4242 | 2.8359 | 2.0125 | 7.1608 | 7.0061 | 8.02E-13 | 2.45E-12 |
| 299-3p | 4.0251 | 4.8027 | 9.6053 | 4.0251 | 7.1608 | 7.0061 | 8.02E-13 | 2.45E-12 |
| 299-5p | 2.8359 | 3.3847 | 8.8735 | 2.8359 | 7.1608 | 7.0061 | 8.02E-13 | 2.45E-12 |
| 323a-3p | 3.1103 | 3.7964 | 8.4161 | 3.1103 | 7.1608 | 7.0061 | 8.02E-13 | 2.45E-12 |
| 337-3p | 4.0251 | 6.4035 | 8.5990 | 4.0251 | 7.1608 | 7.0061 | 8.02E-13 | 2.45E-12 |
| 369-3p | 4.6197 | 5.2601 | 7.5928 | 4.6197 | 7.1608 | 7.0061 | 8.02E-13 | 2.45E-12 |
| 370-3p | 4.3453 | 5.0314 | 8.0959 | 4.3453 | 7.1608 | 7.0061 | 8.02E-13 | 2.45E-12 |
| 371a-3p | 5.1228 | 5.7174 | 6.6322 | 5.1228 | 7.1608 | 7.0061 | 8.02E-13 | 2.45E-12 |
| 371a-5p | 6.3578 | 7.2269 | 8.6905 | 6.3578 | 7.1608 | 7.0061 | 8.02E-13 | 2.45E-12 |
| 372-3p | 6.1748 | 7.1354 | 8.3246 | 6.1748 | 7.1608 | 7.0061 | 8.02E-13 | 2.45E-12 |
| 372-5p | 4.4825 | 5.1686 | 8.0044 | 4.4825 | 7.1608 | 7.0061 | 8.02E-13 | 2.45E-12 |
| 373-3p | 5.5802 | 6.3121 | 7.2269 | 5.5802 | 7.1608 | 7.0061 | 8.02E-13 | 2.45E-12 |
| 373-5p | 5.4430 | 6.0376 | 6.9524 | 5.4430 | 7.1608 | 7.0061 | 8.02E-13 | 2.45E-12 |
| 376a-3p | 6.6322 | 7.3641 | 8.5076 | 6.6322 | 7.1608 | 7.0061 | 8.02E-13 | 2.45E-12 |
| 376b-3p | 3.4762 | 4.2538 | 8.2789 | 3.4762 | 7.1608 | 7.0061 | 8.02E-13 | 2.45E-12 |
| 376c-3p | 6.1748 | 6.9067 | 7.9587 | 6.1748 | 7.1608 | 7.0061 | 8.02E-13 | 2.45E-12 |
| 378a-3p | 1.9211 | 2.2412 | 2.5157 | 1.9211 | 7.1608 | 7.0061 | 8.02E-13 | 2.45E-12 |
| 379-5p | 3.0188 | 3.6592 | 8.9192 | 3.0188 | 7.1608 | 7.0061 | 8.02E-13 | 2.45E-12 |
| 380-3p | 3.7506 | 6.4035 | 8.6448 | 3.7506 | 7.1608 | 7.0061 | 8.02E-13 | 2.45E-12 |
| 381-3p | 6.9067 | 7.5013 | 10.2914 | 6.9067 | 7.1608 | 7.0061 | 8.02E-13 | 2.45E-12 |
| 382-5p | 3.8421 | 6.3578 | 8.5533 | 3.8421 | 7.1608 | 7.0061 | 8.02E-13 | 2.45E-12 |
| 409-3p | 5.2143 | 5.8547 | 9.7425 | 5.2143 | 7.1608 | 7.0061 | 8.02E-13 | 2.45E-12 |
| 411-5p | 5.2143 | 7.7757 | 9.9712 | 5.2143 | 7.1608 | 7.0061 | 8.02E-13 | 2.45E-12 |
| 432-5p | 2.4699 | 3.2018 | 7.9587 | 2.4699 | 7.1608 | 7.0061 | 8.02E-13 | 2.45E-12 |
| 485-3p | 3.8879 | 6.4035 | 8.5990 | 3.8879 | 7.1608 | 7.0061 | 8.02E-13 | 2.45E-12 |
| 487a-3p | 2.6986 | 3.3390 | 8.6448 | 2.6986 | 7.1608 | 7.0061 | 8.02E-13 | 2.45E-12 |
| 487b-3p | 4.5282 | 7.8215 | 9.7883 | 4.5282 | 7.1608 | 7.0061 | 8.02E-13 | 2.45E-12 |
| 493-3p | 3.9793 | 4.5740 | 9.9255 | 3.9793 | 7.1608 | 7.0061 | 8.02E-13 | 2.45E-12 |
| 493-5p | 3.0188 | 3.7964 | 8.6448 | 3.0188 | 7.1608 | 7.0061 | 8.02E-13 | 2.45E-12 |
| 494-3p | 3.2018 | 3.8421 | 8.4161 | 3.2018 | 7.1608 | 7.0061 | 8.02E-13 | 2.45E-12 |
| 498 | 2.2870 | 2.9731 | 3.8421 | 2.2870 | 7.1608 | 7.0061 | 8.02E-13 | 2.45E-12 |
| 512-3p | 4.1623 | 4.4825 | 4.8027 | 4.1623 | 7.1608 | 7.0061 | 8.02E-13 | 2.45E-12 |
| 512-5p | 2.7901 | 3.3847 | 3.9793 | 2.7901 | 7.1608 | 7.0061 | 8.02E-13 | 2.45E-12 |
| 515-5p | 2.2412 | 2.8816 | 3.6592 | 2.2412 | 7.1608 | 7.0061 | 8.02E-13 | 2.45E-12 |
| 516a-5p | 2.6986 | 2.9731 | 3.2018 | 2.6986 | 7.1608 | 7.0061 | 8.02E-13 | 2.45E-12 |
| 516b-5p | 3.1560 | 3.4305 | 3.6592 | 3.1560 | 7.1608 | 7.0061 | 8.02E-13 | 2.45E-12 |
| 517-5p | 3.3390 | 3.7964 | 4.2995 | 3.3390 | 7.1608 | 7.0061 | 8.02E-13 | 2.45E-12 |
| 517a-3p | 2.7901 | 3.1103 | 3.4762 | 2.7901 | 7.1608 | 7.0061 | 8.02E-13 | 2.45E-12 |
| 517b-3p | 2.7901 | 3.1103 | 3.4762 | 2.7901 | 7.1608 | 7.0061 | 8.02E-13 | 2.45E-12 |
| 517c-3p | 2.7901 | 3.4305 | 4.2538 | 2.7901 | 7.1608 | 7.0061 | 8.02E-13 | 2.45E-12 |
| 518a-5p | 3.0188 | 3.6134 | 9.1022 | 3.0188 | 7.1608 | 7.0061 | 8.02E-13 | 2.45E-12 |
| 518b | 2.1955 | 2.6986 | 3.2475 | 2.1955 | 7.1608 | 7.0061 | 8.02E-13 | 2.45E-12 |
| 518c-5p | 2.5614 | 3.1560 | 4.0251 | 2.5614 | 7.1608 | 7.0061 | 8.02E-13 | 2.45E-12 |
| 518d-5p | 2.8816 | 3.2932 | 3.7964 | 2.8816 | 7.1608 | 7.0061 | 8.02E-13 | 2.45E-12 |
| 518e-5p | 3.5677 | 3.9793 | 4.4367 | 3.5677 | 7.1608 | 7.0061 | 8.02E-13 | 2.45E-12 |
| 518f-5p | 3.0188 | 3.4305 | 3.9336 | 3.0188 | 7.1608 | 7.0061 | 8.02E-13 | 2.45E-12 |
| 519a-3p | 3.4762 | 4.1166 | 4.8484 | 3.4762 | 7.1608 | 7.0061 | 8.02E-13 | 2.45E-12 |
| 519a-5p | 3.8421 | 4.2080 | 4.5740 | 3.8421 | 7.1608 | 7.0061 | 8.02E-13 | 2.45E-12 |
| 519b-3p | 3.4762 | 3.9793 | 4.5282 | 3.4762 | 7.1608 | 7.0061 | 8.02E-13 | 2.45E-12 |
| 519b-5p | 3.5219 | 3.9336 | 4.3453 | 3.5219 | 7.1608 | 7.0061 | 8.02E-13 | 2.45E-12 |
| 519c-3p | 2.1498 | 2.4699 | 2.7901 | 2.1498 | 7.1608 | 7.0061 | 8.02E-13 | 2.45E-12 |
| 519c-5p | 3.4762 | 3.9336 | 4.3453 | 3.4762 | 7.1608 | 7.0061 | 8.02E-13 | 2.45E-12 |
| 519d-5p | 3.3390 | 3.8421 | 4.4367 | 3.3390 | 7.1608 | 7.0061 | 8.02E-13 | 2.45E-12 |
| 520a-3p | 4.8027 | 5.3515 | 6.1291 | 4.8027 | 7.1608 | 7.0061 | 8.02E-13 | 2.45E-12 |
| 520a-5p | 3.8421 | 4.1623 | 4.3910 | 3.8421 | 7.1608 | 7.0061 | 8.02E-13 | 2.45E-12 |
| 520b | 3.4762 | 4.0251 | 4.6197 | 3.4762 | 7.1608 | 7.0061 | 8.02E-13 | 2.45E-12 |
| 520c-3p | 3.5677 | 4.0708 | 4.6654 | 3.5677 | 7.1608 | 7.0061 | 8.02E-13 | 2.45E-12 |
| 520c-5p | 2.7901 | 3.2475 | 3.7049 | 2.7901 | 7.1608 | 7.0061 | 8.02E-13 | 2.45E-12 |
| 520d-3p | 3.2475 | 3.7049 | 4.1166 | 3.2475 | 7.1608 | 7.0061 | 8.02E-13 | 2.45E-12 |
| 520d-5p | 2.4242 | 2.7901 | 3.1103 | 2.4242 | 7.1608 | 7.0061 | 8.02E-13 | 2.45E-12 |
| 520e | 1.8753 | 2.3785 | 2.9273 | 1.8753 | 7.1608 | 7.0061 | 8.02E-13 | 2.45E-12 |
| 520f-3p | 3.8421 | 4.2080 | 4.4825 | 3.8421 | 7.1608 | 7.0061 | 8.02E-13 | 2.45E-12 |
| 520f-5p | 2.8816 | 3.6134 | 8.2331 | 2.8816 | 7.1608 | 7.0061 | 8.02E-13 | 2.45E-12 |
| 520g-3p | 3.2018 | 3.7049 | 4.2080 | 3.2018 | 7.1608 | 7.0061 | 8.02E-13 | 2.45E-12 |
| 520g-5p | 2.6986 | 3.2932 | 8.9650 | 2.6986 | 7.1608 | 7.0061 | 8.02E-13 | 2.45E-12 |
| 520h | 2.6529 | 3.3847 | 8.4161 | 2.6529 | 7.1608 | 7.0061 | 8.02E-13 | 2.45E-12 |
| 522-3p | 2.8359 | 3.2018 | 3.5219 | 2.8359 | 7.1608 | 7.0061 | 8.02E-13 | 2.45E-12 |
| 522-5p | 3.4762 | 3.9336 | 4.3453 | 3.4762 | 7.1608 | 7.0061 | 8.02E-13 | 2.45E-12 |
| 523-5p | 3.4762 | 3.8879 | 4.2995 | 3.4762 | 7.1608 | 7.0061 | 8.02E-13 | 2.45E-12 |
| 524-5p | 2.3327 | 2.6529 | 2.9731 | 2.3327 | 7.1608 | 7.0061 | 8.02E-13 | 2.45E-12 |
| 525-5p | 2.0583 | 2.3327 | 2.5614 | 2.0583 | 7.1608 | 7.0061 | 8.02E-13 | 2.45E-12 |

TABLE 6-continued

Significantly (adjusted p-value < 0.05 and abs(mle) > 1) differentially expressed
genes from SCDE. Maximum likelihood estimate (mle) represents the log(fold change).
Table is sorted by p-values.

| miRNA name | lb | mle | ub | ce | Z | cZ | p-value | adjusted p-value |
|---|---|---|---|---|---|---|---|---|
| 526a | 3.0188 | 3.4305 | 3.7964 | 3.0188 | 7.1608 | 7.0061 | 8.02E−13 | 2.45E−12 |
| 526b-5p | 1.7381 | 2.1040 | 2.3785 | 1.7381 | 7.1608 | 7.0061 | 8.02E−13 | 2.45E−12 |
| 654-3p | 2.7444 | 3.7049 | 8.2331 | 2.7444 | 7.1608 | 7.0061 | 8.02E−13 | 2.45E−12 |
| 654-5p | 4.7112 | 7.1354 | 9.3309 | 4.7112 | 7.1608 | 7.0061 | 8.02E−13 | 2.45E−12 |
| 758-3p | 3.7049 | 6.4493 | 8.6448 | 3.7049 | 7.1608 | 7.0061 | 8.02E−13 | 2.45E−12 |
| 889-3p | 3.6134 | 4.2538 | 9.6968 | 3.6134 | 7.1608 | 7.0061 | 8.02E−13 | 2.45E−12 |
| 99a-5p | 4.5740 | 5.2601 | 6.0834 | 4.5740 | 7.1608 | 7.0061 | 8.02E−13 | 2.45E−12 |
| 136-5p | 3.5677 | 6.2663 | 8.4161 | 3.5677 | 7.1608 | 7.0061 | 8.02E−13 | 2.45E−12 |
| 92a-1-5p | 1.1892 | 1.6009 | 1.9668 | 1.1892 | 7.1608 | 7.0061 | 8.02E−13 | 2.45E−12 |
| 495-3p | 3.4762 | 6.4035 | 8.5990 | 3.4762 | 7.1608 | 7.0061 | 8.02E−13 | 2.45E−12 |
| 665 | 3.6592 | 5.9919 | 8.1874 | 3.6592 | 7.1608 | 7.0061 | 8.02E−13 | 2.45E−12 |
| 3180-3p | 2.1040 | 2.9273 | 4.0708 | 2.1040 | 7.1608 | 7.0061 | 8.02E−13 | 2.45E−12 |
| 411-3p | 3.3847 | 6.0376 | 8.2331 | 3.3847 | 7.1608 | 7.0061 | 8.02E−13 | 2.45E−12 |
| 527 | 3.3847 | 5.8547 | 8.0959 | 3.3847 | 7.1608 | 7.0061 | 8.02E−13 | 2.45E−12 |
| 519e-5p | 1.9668 | 2.6529 | 3.7049 | 1.9668 | 7.1608 | 7.0061 | 8.02E−13 | 2.45E−12 |
| 134-5p | 3.4305 | 5.8547 | 8.0502 | 3.4305 | 7.1608 | 7.0061 | 8.02E−13 | 2.45E−12 |
| 409-5p | 3.4762 | 5.9004 | 8.0959 | 3.4762 | 7.1608 | 7.0061 | 8.02E−13 | 2.45E−12 |
| 431-3p | 3.3390 | 5.7174 | 7.9587 | 3.3390 | 7.1608 | 7.0061 | 8.02E−13 | 2.45E−12 |
| 518e-3p | 2.8816 | 6.4493 | 8.2331 | 2.8816 | 7.1608 | 7.0061 | 8.02E−13 | 2.45E−12 |
| 518f-3p | 2.5157 | 7.8672 | 8.3703 | 2.5157 | 7.1608 | 7.0061 | 8.02E−13 | 2.45E−12 |
| 539-3p | 3.2475 | 5.6260 | 7.8215 | 3.2475 | 7.1608 | 7.0061 | 8.02E−13 | 2.45E−12 |
| 329-3p | 3.2475 | 5.6260 | 7.8215 | 3.2475 | 7.1608 | 7.0061 | 8.02E−13 | 2.45E−12 |
| hsa-let-7a-5p | −5.6260 | −5.0771 | −4.5740 | −4.5740 | −7.1608 | −7.0061 | 8.02E−13 | 2.45E−12 |
| 103a-3p | −2.6072 | −2.2870 | −2.0125 | −2.0125 | −7.1608 | −7.0061 | 8.02E−13 | 2.45E−12 |
| 1180-3p | −2.6986 | −2.2412 | −1.8296 | −1.8296 | −7.1608 | −7.0061 | 8.02E−13 | 2.45E−12 |
| 146a-5p | −9.7883 | −4.8941 | −3.8421 | −3.8421 | −7.1608 | −7.0061 | 8.02E−13 | 2.45E−12 |
| 148a-3p | −2.0583 | −1.8296 | −1.6466 | −1.6466 | −7.1608 | −7.0061 | 8.02E−13 | 2.45E−12 |
| 151a-3p | −2.0583 | −1.6924 | −1.4179 | −1.4179 | −7.1608 | −7.0061 | 8.02E−13 | 2.45E−12 |
| 155-5p | −8.4161 | −4.0708 | −3.3847 | −3.3847 | −7.1608 | −7.0061 | 8.02E−13 | 2.45E−12 |
| 181b-5p | −3.8421 | −3.1103 | −2.5614 | −2.5614 | −7.1608 | −7.0061 | 8.02E−13 | 2.45E−12 |
| 186-5p | −3.4762 | −3.1103 | −2.7901 | −2.7901 | −7.1608 | −7.0061 | 8.02E−13 | 2.45E−12 |
| 187-3p | −8.6905 | −7.3641 | −3.8879 | −3.8879 | −7.1608 | −7.0061 | 8.02E−13 | 2.45E−12 |
| 20a-5p | −2.1955 | −1.7838 | −1.4179 | −1.4179 | −7.1608 | −7.0061 | 8.02E−13 | 2.45E−12 |
| 20b-3p | −7.9129 | −6.2663 | −3.7049 | −3.7049 | −7.1608 | −7.0061 | 8.02E−13 | 2.45E−12 |
| 2113 | −8.0044 | −6.6322 | −3.4762 | −3.4762 | −7.1608 | −7.0061 | 8.02E−13 | 2.45E−12 |
| 221-5p | −3.0646 | −2.3785 | −1.8296 | −1.8296 | −7.1608 | −7.0061 | 8.02E−13 | 2.45E−12 |
| 222-3p | −4.3910 | −3.9793 | −3.6134 | −3.6134 | −7.1608 | −7.0061 | 8.02E−13 | 2.45E−12 |
| 28-3p | −3.4305 | −3.0188 | −2.6529 | −2.6529 | −7.1608 | −7.0061 | 8.02E−13 | 2.45E−12 |
| 301a-3p | −4.0251 | −3.1103 | −2.5157 | −2.5157 | −7.1608 | −7.0061 | 8.02E−13 | 2.45E−12 |
| 302a-3p | −2.5614 | −2.3327 | −2.1498 | −2.1498 | −7.1608 | −7.0061 | 8.02E−13 | 2.45E−12 |
| 302b-3p | −2.2870 | −2.1040 | −1.9211 | −1.9211 | −7.1608 | −7.0061 | 8.02E−13 | 2.45E−12 |
| 302c-3p | −4.2995 | −3.9336 | −3.6134 | −3.6134 | −7.1608 | −7.0061 | 8.02E−13 | 2.45E−12 |
| 30a-5p | −3.8421 | −3.2018 | −2.6072 | −2.6072 | −7.1608 | −7.0061 | 8.02E−13 | 2.45E−12 |
| 367-3p | −2.9731 | −2.6072 | −2.2870 | −2.2870 | −7.1608 | −7.0061 | 8.02E−13 | 2.45E−12 |
| 423-3p | −1.4637 | −1.1892 | −1.0063 | −1.0063 | −7.1608 | −7.0061 | 8.02E−13 | 2.45E−12 |
| 423-5p | −1.2350 | −0.9605 | −0.7776 | −0.7776 | −7.1608 | −7.0061 | 8.02E−13 | 2.45E−12 |
| 450a-5p | −4.0251 | −3.2018 | −2.6072 | −2.6072 | −7.1608 | −7.0061 | 8.02E−13 | 2.45E−12 |
| 454-3p | −4.0251 | −3.0646 | −2.4699 | −2.4699 | −7.1608 | −7.0061 | 8.02E−13 | 2.45E−12 |
| 744-5p | −3.3847 | −2.9273 | −2.5614 | −2.5614 | −7.1608 | −7.0061 | 8.02E−13 | 2.45E−12 |
| 769-3p | −7.8215 | −2.9731 | −2.2870 | −2.2870 | −7.1608 | −7.0061 | 8.02E−13 | 2.45E−12 |
| 92b-3p | −4.7569 | −4.4367 | −4.1623 | −4.1623 | −7.1608 | −7.0061 | 8.02E−13 | 2.45E−12 |
| 99b-5p | −1.6009 | −1.2807 | −1.0063 | −1.0063 | −7.1608 | −7.0061 | 8.02E−13 | 2.45E−12 |
| 410-3p | 3.1560 | 5.5802 | 7.7757 | 3.1560 | 7.1608 | 7.0061 | 8.02E−13 | 2.45E−12 |
| 154-3p | 2.8816 | 5.5802 | 7.7300 | 2.8816 | 7.1608 | 7.0061 | 8.02E−13 | 2.45E−12 |
| 302d-3p | −2.5614 | −2.3327 | −2.1498 | −2.1498 | −7.1608 | −7.0061 | 8.02E−13 | 2.45E−12 |
| 769-5p | −3.4762 | −2.9731 | −2.5157 | −2.5157 | −7.1608 | −7.0061 | 8.02E−13 | 2.45E−12 |
| 485-5p | 3.2018 | 5.5802 | 7.7757 | 3.2018 | 7.1608 | 7.0061 | 8.02E−13 | 2.45E−12 |
| 377-5p | 3.0646 | 5.4430 | 7.6385 | 3.0646 | 7.1606 | 7.0061 | 8.03E−13 | 2.45E−12 |
| 590-3p | −1.9211 | −1.4637 | −1.0977 | −1.0977 | −7.1605 | −7.0061 | 8.04E−13 | 2.45E−12 |
| 625-5p | 1.1435 | 1.5551 | 2.0125 | 1.1435 | 7.1604 | 7.0061 | 8.04E−13 | 2.45E−12 |
| 450b-5p | −7.9129 | −6.5408 | −2.6529 | −2.6529 | −7.1601 | −7.0061 | 8.06E−13 | 2.45E−12 |
| 15b-5p | −2.4699 | −1.9211 | −1.4179 | −1.4179 | −7.1600 | −7.0061 | 8.07E−13 | 2.45E−12 |
| 296-3p | −2.0583 | −1.6009 | −1.1892 | −1.1892 | −7.1598 | −7.0061 | 8.08E−13 | 2.45E−12 |
| 200a-3p | −3.6134 | −2.6529 | −1.8753 | −1.8753 | −7.1598 | −7.0061 | 8.08E−13 | 2.45E−12 |
| 323b-3p | 2.9731 | 5.6717 | 7.7757 | 2.9731 | 7.1577 | 7.0052 | 8.20E−13 | 2.47E−12 |
| 330-3p | −2.7444 | −2.1040 | −1.5094 | −1.5094 | −7.1574 | −7.0052 | 8.22E−13 | 2.47E−12 |
| 125b-2-3p | 2.8359 | 5.6260 | 8.0044 | 2.8359 | 7.1559 | 7.0049 | 8.31E−13 | 2.47E−12 |
| 205-5p | −2.6986 | −2.0583 | −1.4637 | −1.4637 | −7.1557 | −7.0049 | 8.33E−13 | 2.47E−12 |
| 127-5p | 2.9273 | 5.3058 | 7.5013 | 2.9273 | 7.1538 | 7.0037 | 8.44E−13 | 2.49E−12 |
| 503-5p | −7.6842 | −6.0376 | −3.3847 | −3.3847 | −7.1512 | −7.0018 | 8.60E−13 | 2.53E−12 |
| 425-3p | −1.7838 | −1.3722 | −1.0063 | −1.0063 | −7.1478 | −6.9991 | 8.82E−13 | 2.58E−12 |
| 539-5p | 2.6072 | 5.7632 | 7.8215 | 2.6072 | 7.1412 | 6.9931 | 9.25E−13 | 2.69E−12 |
| 1301-3p | −3.0646 | −2.1955 | −1.5551 | −1.5551 | −7.1151 | −6.9671 | 1.12E−12 | 3.23E−12 |

TABLE 6-continued

Significantly (adjusted p-value < 0.05 and abs(mle) > 1) differentially expressed
genes from SCDE. Maximum likelihood estimate (mle) represents the log(fold change).
Table is sorted by p-values.

| miRNA name | lb | mle | ub | ce | Z | cZ | p-value | adjusted p-value |
|---|---|---|---|---|---|---|---|---|
| 523-3p | 2.8359 | 5.5802 | 7.7300 | 2.8359 | 7.1123 | 6.9650 | 1.14E−12 | 3.28E−12 |
| 140-3p | −1.6924 | −1.3264 | −0.9148 | −0.9148 | −7.0475 | −6.8996 | 1.82E−12 | 5.22E−12 |
| 515-3p | 1.6009 | 2.3327 | 6.6780 | 1.6009 | 7.0179 | 6.8701 | 2.25E−12 | 6.42E−12 |
| 505-3p | −2.8359 | −2.0583 | −1.4637 | −1.4637 | −6.9855 | −6.8378 | 2.84E−12 | 8.04E−12 |
| 21-5p | −1.0977 | −0.8233 | −0.5489 | −0.5489 | −6.9292 | −6.7810 | 4.23E−12 | 1.19E−11 |
| 1307-3p | −1.8753 | −1.4179 | −1.0063 | −1.0063 | −6.8934 | −6.7451 | 5.45E−12 | 1.53E−11 |
| 3187-3p | −7.5470 | −6.0376 | −3.1103 | −3.1103 | −6.8714 | −6.7235 | 6.36E−12 | 1.77E−11 |
| 518a-3p | 2.5614 | 5.3058 | 7.4555 | 2.5614 | 6.8573 | 6.7098 | 7.02E−12 | 1.95E−11 |
| 543 | 1.6466 | 2.2870 | 7.7757 | 1.6466 | 6.8509 | 6.7039 | 7.34E−12 | 2.03E−11 |
| 27b-3p | −1.4179 | −1.0520 | −0.7318 | −0.7318 | −6.7830 | −6.6360 | 1.18E−11 | 3.22E−11 |
| 526b-3p | 2.4242 | 5.1228 | 7.5013 | 2.4242 | 6.7813 | 6.6350 | 1.19E−11 | 3.24E−11 |
| 382-3p | 2.6529 | 5.0314 | 7.2269 | 2.6529 | 6.6899 | 6.5423 | 2.23E−11 | 6.06E−11 |
| 106a-5p | −7.4098 | −5.7174 | −3.2018 | −3.2018 | −6.5853 | −6.4361 | 4.54E−11 | 1.23E−10 |
| 146b-5p | 2.5157 | 5.3515 | 7.5470 | 2.5157 | 6.4535 | 6.3022 | 1.09E−10 | 2.94E−10 |
| 519d-3p | 2.5157 | 4.9399 | 7.1354 | 2.5157 | 6.3833 | 6.2311 | 1.73E−10 | 4.63E−10 |
| 100-5p | −7.9129 | −2.8359 | −2.0583 | −2.0583 | −6.3469 | −6.1946 | 2.20E−10 | 5.84E−10 |
| 323a-5p | 2.5614 | 5.2601 | 7.4555 | 2.5614 | 6.3370 | 6.1852 | 2.34E−10 | 6.20E−10 |
| 9-3p | −2.5157 | −1.8753 | −1.2807 | −1.2807 | −6.2656 | −6.1136 | 3.71E−10 | 9.74E−10 |
| 656-3p | 2.5157 | 4.8941 | 7.0896 | 2.5157 | 6.2656 | 6.1136 | 3.71E−10 | 9.74E−10 |
| 149-5p | −2.0125 | −1.5094 | −1.0520 | −1.0520 | −6.1493 | −5.9952 | 7.78E−10 | 2.03E−09 |
| 95-3p | −6.3578 | −2.2870 | −1.5094 | −1.5094 | −6.1324 | −5.9787 | 8.66E−10 | 2.25E−09 |
| 3180 | 2.2412 | 4.7112 | 7.6385 | 2.2412 | 6.0799 | 5.9257 | 1.20E−09 | 3.11E−09 |
| 2110 | −2.1955 | −1.6009 | −1.0520 | −1.0520 | −5.7695 | −5.6079 | 7.95E−09 | 2.05E−08 |
| 433-3p | 2.2870 | 4.8941 | 7.0439 | 2.2870 | 5.7285 | 5.5666 | 1.01E−08 | 2.60E−08 |
| 342-3p | −2.7901 | −1.9211 | −1.2807 | −1.2807 | −5.7056 | −5.5438 | 1.16E−08 | 2.96E−08 |
| 874-3p | −2.4699 | −1.7838 | −1.1892 | −1.1892 | −5.6721 | −5.5102 | 1.41E−08 | 3.58E−08 |
| 655-3p | 2.2870 | 4.6654 | 6.8609 | 2.2870 | 5.5591 | 5.3957 | 2.71E−08 | 6.83E−08 |
| 96-5p | 1.0977 | 1.8296 | 4.5740 | 1.0977 | 5.5254 | 5.3618 | 3.29E−08 | 8.24E−08 |
| 379-3p | 2.3327 | 4.7112 | 6.9067 | 2.3327 | 5.5028 | 5.3394 | 3.74E−08 | 9.33E−08 |
| 10b-5p | 1.1892 | 1.9668 | 6.6322 | 1.1892 | 5.4600 | 5.2961 | 4.76E−08 | 1.18E−07 |
| 548f-3p | −7.1811 | −5.1228 | −2.5614 | −2.5614 | −5.3812 | −5.2157 | 7.40E−08 | 1.83E−07 |
| 760 | −7.1811 | −5.5802 | −2.6529 | −2.6529 | −5.3541 | −5.1887 | 8.60E−08 | 2.12E−07 |
| 92a-2-5p | −7.2726 | −5.5345 | −3.0188 | −3.0188 | −5.3224 | −5.1568 | 1.02E−07 | 2.51E−07 |
| 24-3p | −2.3785 | −1.5551 | −0.9605 | −0.9605 | −5.1798 | −5.0115 | 2.22E−07 | 5.40E−07 |
| 185-5p | −1.4179 | −1.0063 | −0.6404 | −0.6404 | −5.1616 | −4.9936 | 2.45E−07 | 5.93E−07 |
| 369-5p | 2.1955 | 4.6197 | 6.8609 | 2.1955 | 5.1534 | 4.9859 | 2.56E−07 | 6.17E−07 |
| 4281 | −2.1498 | −1.4637 | −0.9148 | −0.9148 | −5.0496 | −4.8806 | 4.43E−07 | 1.06E−06 |
| 320c | −1.8296 | −1.2807 | −0.7776 | −0.7776 | −5.0170 | −4.8477 | 5.25E−07 | 1.25E−06 |
| 222-5p | −2.8359 | −1.8296 | −1.1435 | −1.1435 | −4.9719 | −4.8020 | 6.63E−07 | 1.57E−06 |
| 26b-5p | −1.0520 | −0.6861 | −0.4117 | −0.4117 | −4.9647 | −4.7954 | 6.88E−07 | 1.62E−06 |
| 184 | −7.0896 | −5.3973 | −2.7901 | −2.7901 | −4.9447 | −4.7756 | 7.63E−07 | 1.79E−06 |
| 141-5p | 1.3722 | 2.1040 | 7.5013 | 1.3722 | 4.9365 | 4.7680 | 7.95E−07 | 1.86E−06 |
| 107 | −7.1354 | −2.0583 | −1.2350 | −1.2350 | −4.9264 | −4.7583 | 8.38E−07 | 1.95E−06 |
| 340-3p | −6.7237 | −2.1040 | −1.2807 | −1.2807 | −4.9113 | −4.7436 | 9.05E−07 | 2.10E−06 |
| 361-3p | −2.1498 | −1.4179 | −0.8691 | −0.8691 | −4.8287 | −4.6603 | 1.37E−06 | 3.16E−06 |
| 30a-3p | −6.8609 | −5.3058 | −2.2412 | −2.2412 | −4.7725 | −4.6052 | 1.82E−06 | 4.12E−06 |
| 484 | −1.2350 | −0.8233 | −0.5031 | −0.5031 | −4.7691 | −4.6024 | 1.84E−06 | 4.18E−06 |
| 431-5p | 1.8753 | 4.2995 | 6.5408 | 1.8753 | 4.7603 | 4.5942 | 1.93E−06 | 4.34E−06 |
| 320a | −1.9211 | −1.3264 | −0.7318 | −0.7318 | −4.5955 | −4.4263 | 4.32E−06 | 9.59E−06 |
| 598-3p | −6.9524 | −5.3973 | −2.4699 | −2.4699 | −4.5940 | −4.4256 | 4.35E−06 | 9.62E−06 |
| 106b-5p | −2.2412 | −1.5551 | −0.9148 | −0.9148 | −4.5401 | −4.3715 | 5.62E−06 | 1.23E−05 |
| 370-5p | 1.7838 | 4.2080 | 6.4493 | 1.7838 | 4.4445 | 4.2733 | 8.81E−06 | 1.93E−05 |
| 377-3p | 1.8296 | 4.2538 | 6.4950 | 1.8296 | 4.4098 | 4.2382 | 1.03E−05 | 2.25E−05 |
| 181a-2-3p | −5.2143 | −1.8753 | −1.0063 | −1.0063 | −4.3808 | −4.2090 | 1.18E−05 | 2.57E−05 |
| 200b-5p | −7.0896 | −2.1955 | −1.4637 | −1.4637 | −4.3675 | −4.1961 | 1.26E−05 | 2.72E−05 |
| 499a-5p | 1.7381 | 4.2538 | 6.4493 | 1.7381 | 4.3219 | 4.1496 | 1.55E−05 | 3.33E−05 |
| 671-5p | −1.6924 | −1.1435 | −0.6404 | −0.6404 | −4.3140 | −4.1423 | 1.60E−05 | 3.44E−05 |
| 23b-3p | −1.5094 | −1.0063 | −0.5946 | −0.5946 | −4.2501 | −4.0777 | 2.14E−05 | 4.55E−05 |
| 767-5p | −6.7695 | −5.0314 | −2.4699 | −2.4699 | −4.2481 | −4.0765 | 2.16E−05 | 4.57E−05 |
| 135b-5p | −2.0125 | −1.3264 | −0.6861 | −0.6861 | −4.2459 | −4.0751 | 2.16E−05 | 4.60E−05 |
| 301b-3p | −6.9067 | −5.1228 | −2.6072 | −2.6072 | −4.2187 | −4.0478 | 2.46E−05 | 5.17E−05 |
| 424-5p | −6.7237 | −4.1623 | −1.7838 | −1.7838 | −4.1485 | −3.9757 | 3.35E−05 | 7.02E−05 |
| 3679-5p | −6.8609 | −5.1686 | −2.5614 | −2.5614 | −4.1395 | −3.9673 | 3.48E−05 | 7.27E−05 |
| 1307-5p | −2.5157 | −1.5551 | −0.8691 | −0.8691 | −4.1028 | −3.9300 | 4.08E−05 | 8.50E−05 |
| 30c-5p | −1.1892 | −0.7776 | −0.4574 | −0.4574 | −4.0615 | −3.8879 | 4.88E−05 | 0.00010 |
| 182-3p | 1.6009 | 4.3453 | 6.4950 | 1.6009 | 4.0254 | 3.8513 | 5.69E−05 | 0.00012 |
| 521 | 1.5551 | 4.4825 | 6.5865 | 1.5551 | 4.0193 | 3.8459 | 5.84E−05 | 0.00012 |
| 3180-5p | 1.6466 | 4.0708 | 6.2663 | 1.6466 | 4.0070 | 3.8339 | 6.15E−05 | 0.00013 |
| 378a-5p | 1.1892 | 4.3910 | 6.7695 | 1.1892 | 3.9566 | 3.7824 | 7.60E−05 | 0.00016 |
| 331-3p | −6.7237 | −3.8421 | −1.4179 | −1.4179 | −3.9151 | −3.7400 | 9.04E−05 | 0.00018 |
| 542-5p | −6.8152 | −5.0314 | −2.4699 | −2.4699 | −3.8962 | −3.7212 | 9.77E−05 | 0.00020 |
| 424-3p | −2.4699 | −1.6466 | −0.8233 | −0.8233 | −3.8034 | −3.6254 | 0.00014 | 0.00029 |
| 1305 | −6.6322 | −4.8484 | −2.3327 | −2.3327 | −3.7396 | −3.5597 | 0.00018 | 0.00037 |

TABLE 6-continued

Significantly (adjusted p-value < 0.05 and abs(mle) > 1) differentially expressed genes from SCDE. Maximum likelihood estimate (mle) represents the log(fold change). Table is sorted by p-values.

| miRNA name | lb | mle | ub | ce | Z | cZ | p-value | adjusted p-value |
|---|---|---|---|---|---|---|---|---|
| 210-3p | −1.6009 | −1.0063 | −0.5031 | −0.5031 | −3.7149 | −3.5349 | 0.00020 | 0.00041 |
| 126-3p | −1.3722 | −0.8691 | −0.4117 | −0.4117 | −3.6639 | −3.4824 | 0.00025 | 0.00050 |
| 7706 | −6.7237 | −4.9856 | −2.1955 | −2.1955 | −3.6412 | −3.4596 | 0.00027 | 0.00054 |
| 105-5p | −6.7695 | −4.9856 | −2.4242 | −2.4242 | −3.6402 | −3.4596 | 0.00027 | 0.00054 |
| 132-5p | −6.9067 | −2.2412 | −1.2807 | −1.2807 | −3.5932 | −3.4114 | 0.00033 | 0.00065 |
| 491-5p | −6.9067 | −1.8296 | −0.9605 | −0.9605 | −3.5819 | −3.4005 | 0.00034 | 0.00067 |
| 96-3p | 1.3722 | 4.1166 | 6.2663 | 1.3722 | 3.5584 | 3.3777 | 0.00037 | 0.00073 |
| 500a-3p | −1.4637 | −0.9148 | −0.4117 | −0.4117 | −3.4817 | −3.3004 | 0.00050 | 0.00097 |
| 1-3p | −2.2870 | −1.2807 | −0.5489 | −0.5489 | −3.4631 | −3.2819 | 0.00053 | 0.00103 |
| 320d | −6.4035 | −1.8296 | −0.9605 | −0.9605 | −3.3988 | −3.2163 | 0.00068 | 0.00130 |
| 190a-5p | −1.6466 | −1.0063 | −0.4574 | −0.4574 | −3.3489 | −3.1649 | 0.00081 | 0.00155 |
| 758-5p | 1.4637 | 3.9793 | 6.2663 | 1.4637 | 3.3113 | 3.1265 | 0.00093 | 0.00177 |
| 429 | −6.7237 | −3.3847 | −1.5551 | −1.5551 | −3.2719 | −3.0860 | 0.00107 | 0.00203 |
| 516b-3p | 1.0977 | 3.9793 | 6.1748 | 1.0977 | 3.2266 | 3.0393 | 0.00125 | 0.00237 |
| 181d-5p | −6.4493 | −3.3847 | −1.3722 | −1.3722 | −3.1648 | −2.9763 | 0.00155 | 0.00292 |
| 505-5p | −2.0583 | −1.1892 | −0.5031 | −0.5031 | −3.1247 | −2.9350 | 0.00178 | 0.00333 |
| 15a-5p | −2.4699 | −1.3264 | −0.5031 | −0.5031 | −3.1013 | −2.9124 | 0.00193 | 0.00359 |
| 138-5p | −1.0520 | −0.5946 | −0.2287 | −0.2287 | −3.0928 | −2.9045 | 0.00198 | 0.00368 |
| 218-5p | −6.6780 | −1.7381 | −0.7318 | −0.7318 | −3.0899 | −2.9025 | 0.00200 | 0.00370 |
| 186-3p | −6.4493 | −4.7112 | −1.6466 | −1.6466 | −3.0865 | −2.8999 | 0.00202 | 0.00373 |
| 6088 | −1.7838 | −1.0977 | −0.4117 | −0.4117 | −3.0678 | −2.8812 | 0.00216 | 0.00396 |
| 143-3p | −1.7838 | −1.0063 | −0.3659 | −0.3659 | −3.0443 | −2.8585 | 0.00233 | 0.00426 |
| 452-5p | −6.5408 | −4.7112 | −2.0583 | −2.0583 | −3.0017 | −2.8145 | 0.00268 | 0.00488 |
| 448 | −2.1955 | −1.1435 | −0.4117 | −0.4117 | −2.9624 | −2.7751 | 0.00305 | 0.00552 |
| 1343-3p | −6.1748 | −1.4637 | −0.5489 | −0.5489 | −2.9557 | −2.7691 | 0.00312 | 0.00562 |
| 129-5p | −6.6780 | −4.8484 | −2.1498 | −2.1498 | −2.9469 | −2.7608 | 0.00321 | 0.00577 |
| 1263 | −6.4035 | −4.5740 | −1.9668 | −1.9668 | −2.9394 | −2.7539 | 0.00329 | 0.00589 |
| 641 | −6.5865 | −1.4179 | −0.5489 | −0.5489 | −2.9205 | −2.7350 | 0.00349 | 0.00624 |
| 18a-3p | −6.6780 | −1.4637 | −0.5489 | −0.5489 | −2.9110 | −2.7269 | 0.00360 | 0.00639 |
| 3615 | −1.9211 | −1.0520 | −0.3659 | −0.3659 | −2.9034 | −2.7201 | 0.00369 | 0.00653 |
| 873-5p | −6.3578 | −1.6466 | −0.6861 | −0.6861 | −2.8494 | −2.6645 | 0.00438 | 0.00771 |
| 4746-5p | −6.4950 | −4.7112 | −1.9211 | −1.9211 | −2.8488 | −2.6645 | 0.00439 | 0.00771 |
| 329-5p | 1.0977 | 3.6592 | 5.9461 | 1.0977 | 2.8315 | 2.6473 | 0.00463 | 0.00811 |
| 455-3p | −1.3264 | −0.7776 | −0.2287 | −0.2287 | −2.7989 | −2.6139 | 0.00513 | 0.00895 |
| 1912 | −1.8753 | −1.0520 | −0.3202 | −0.3202 | −2.7927 | −2.6087 | 0.00523 | 0.00909 |
| 561-5p | −2.1955 | −1.1892 | −0.4117 | −0.4117 | −2.7921 | −2.6087 | 0.00524 | 0.00909 |
| 29a-3p | −5.4887 | −1.2350 | −0.4117 | −0.4117 | −2.7747 | −2.5925 | 0.00552 | 0.00953 |
| 185-3p | −6.3578 | −4.4825 | −0.7776 | −0.7776 | −2.7565 | −2.5742 | 0.00584 | 0.01005 |
| 106b-3p | −1.1435 | −0.5946 | −0.1830 | −0.1830 | −2.7531 | −2.5717 | 0.00590 | 0.01012 |
| 32-3p | −1.2350 | −0.6861 | −0.2287 | −0.2287 | −2.7492 | −2.5686 | 0.00597 | 0.01021 |
| 3065-3p | −6.2206 | −4.4825 | −1.4179 | −1.4179 | −2.6414 | −2.4566 | 0.00826 | 0.01402 |
| 187-5p | −6.3578 | −4.5740 | −1.8296 | −1.8296 | −2.6393 | −2.4554 | 0.00831 | 0.01407 |
| 375 | −2.8359 | −1.8296 | −0.4574 | −0.4574 | −2.6135 | −2.4310 | 0.00896 | 0.01506 |
| 320b | −1.2350 | −0.7318 | −0.1830 | −0.1830 | −2.6131 | −2.4310 | 0.00897 | 0.01506 |
| 19b-3p | −1.6466 | −0.9605 | −0.2287 | −0.2287 | −2.5249 | −2.3395 | 0.01157 | 0.01931 |
| 548k | −6.1291 | −1.1892 | −0.2744 | −0.2744 | −2.4714 | −2.2848 | 0.01346 | 0.02232 |
| 331-5p | −1.0977 | −0.5946 | −0.1372 | −0.1372 | −2.4182 | −2.2304 | 0.01560 | 0.02572 |
| 766-5p | −6.3578 | −1.3722 | −0.3659 | −0.3659 | −2.3735 | −2.1861 | 0.01762 | 0.02881 |
| 324-5p | −6.1748 | −4.3453 | −0.6404 | −0.6404 | −2.3637 | −2.1768 | 0.01810 | 0.02950 |
| 122-5p | −1.5551 | −0.8233 | −0.1830 | −0.1830 | −2.3504 | −2.1637 | 0.01876 | 0.03048 |
| 212-5p | −6.0834 | −1.0977 | −0.1830 | −0.1830 | −2.2842 | −2.0966 | 0.02236 | 0.03603 |
| 501-5p | −1.4637 | −0.7776 | −0.1372 | −0.1372 | −2.2464 | −2.0574 | 0.02468 | 0.03965 |
| 708-3p | −2.2870 | −1.0977 | −0.1830 | −0.1830 | −2.2357 | −2.0471 | 0.02537 | 0.04065 |
| 124-5p | −3.0646 | −1.1892 | −0.1830 | −0.1830 | −2.2044 | −2.0148 | 0.02749 | 0.04393 |
| 342-5p | −6.0834 | −1.3264 | −0.2287 | −0.2287 | −2.2011 | −2.0124 | 0.02773 | 0.04418 |
| 1303 | −6.2663 | −1.4637 | −0.2744 | −0.2744 | −2.1739 | −1.9844 | 0.02971 | 0.04721 |

Example 6: Heterogeneity of miRNA Expression in Primed and Naïve hESCs

Next, the heterogeneity of miRNA expression was assessed in primed and naïve hESCs (FIG. 4i). Differential expression of miRNAs in naïve (n=97 cells) and primed hESCs (n=90) was determined using SCDE with default parameters except requiring a minimum of 100 genes to consider for the test (parameter min·size·entries=100 to call scde.error.models function). miRNAs with no expression in naïve or primed hESCs were excluded before analysis. The Z scores and corrected Z scores (cZ) to adjust for the multiple testing were converted into two sided p-values using pnorm function in R. The average miRNA abundance in naïve and primed hESCs was plotted in a scatterplot, were significantly differentially expressed miRNAs (SCDE adjusted p-value <0.05 and fold change >2) were colored red. See FIG. 5. (a) Spearman coefficients for correlation of miRNA expression among compared pairs of single cells within each cell type. Naive cells were subsampled according to the molecule distribution of primed cells in order to normalize the differences in cell sizes. Welch Two Sample t-test was applied to compare two distributions. Line in the middle of boxes represents median. Next to median are notches, which represent confidence interval around the median. Primed ESCs showed less correlation that was statistically significant among single cells compared to naive hESCs. (b) Distribution of cells according to the miRNA molecular contents. The miRNAs 127-3p, 371-5p, 372-3p, 373-3p, and 375 showed higher levels of noise in primed hESCs (FIG. 4i). Therefore, the molecular levels of the same miRNAs were examined in primed and naive hESCs (90 and 97 cells respectively). A few single primed cells appeared to express more miRNAs compared to the rest of the population. (c) Other miRNAs that varied less in single cells were expressed rather similarly in the cells of the same type. Only one primed stem cell showed higher expression of some miRNAs.

Figures 4, 5:
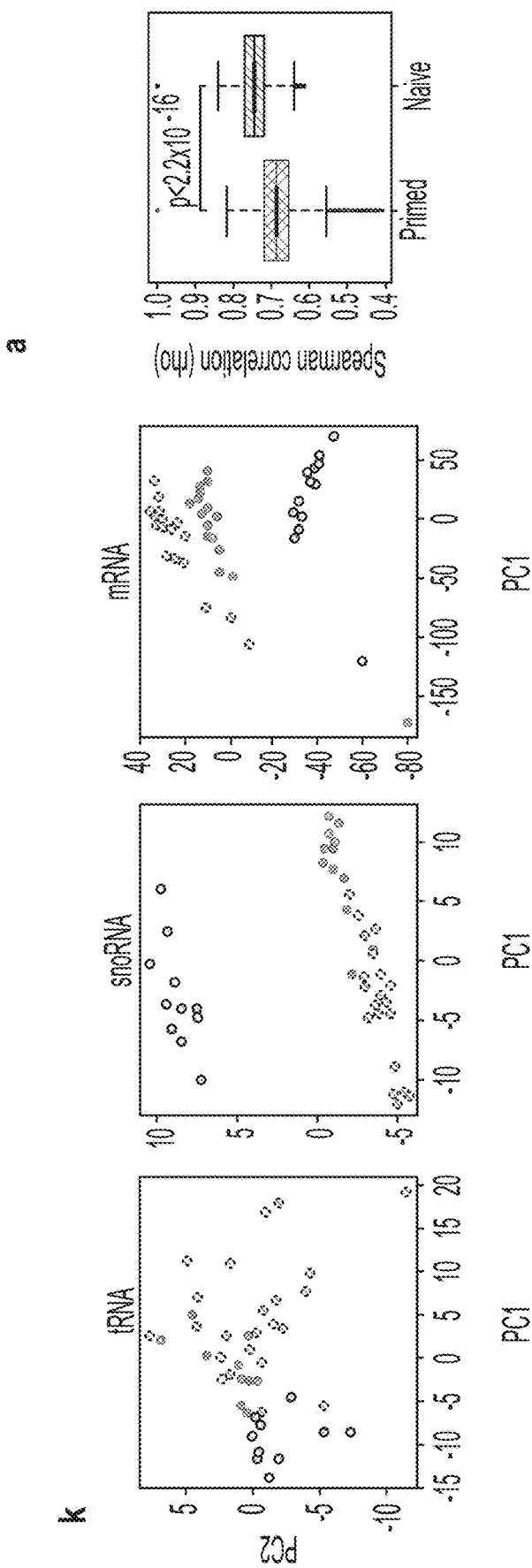
FIG. 5 illustrates heterogeneity in primed and naïve hESCs. (a) Spearman coefficients for correlation of miRNA expression among compared pairs of single cells within each cell type. (b) Distribution of cells according to the miRNA molecular contents. (c) Other miRNAs that varied less in single cells were expressed rather similarly in the cells of the same type.
Figure 5:
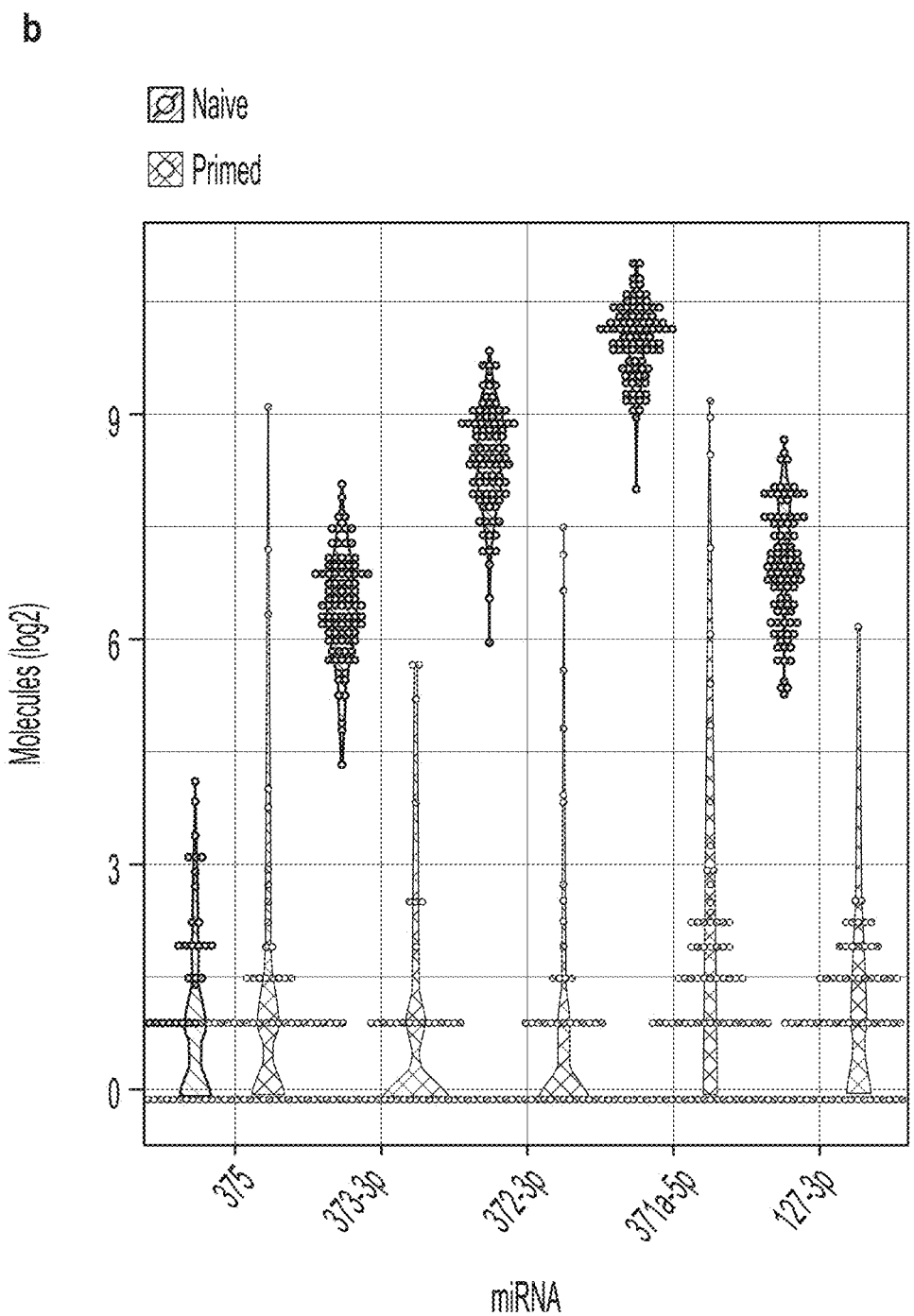
Figure 5:
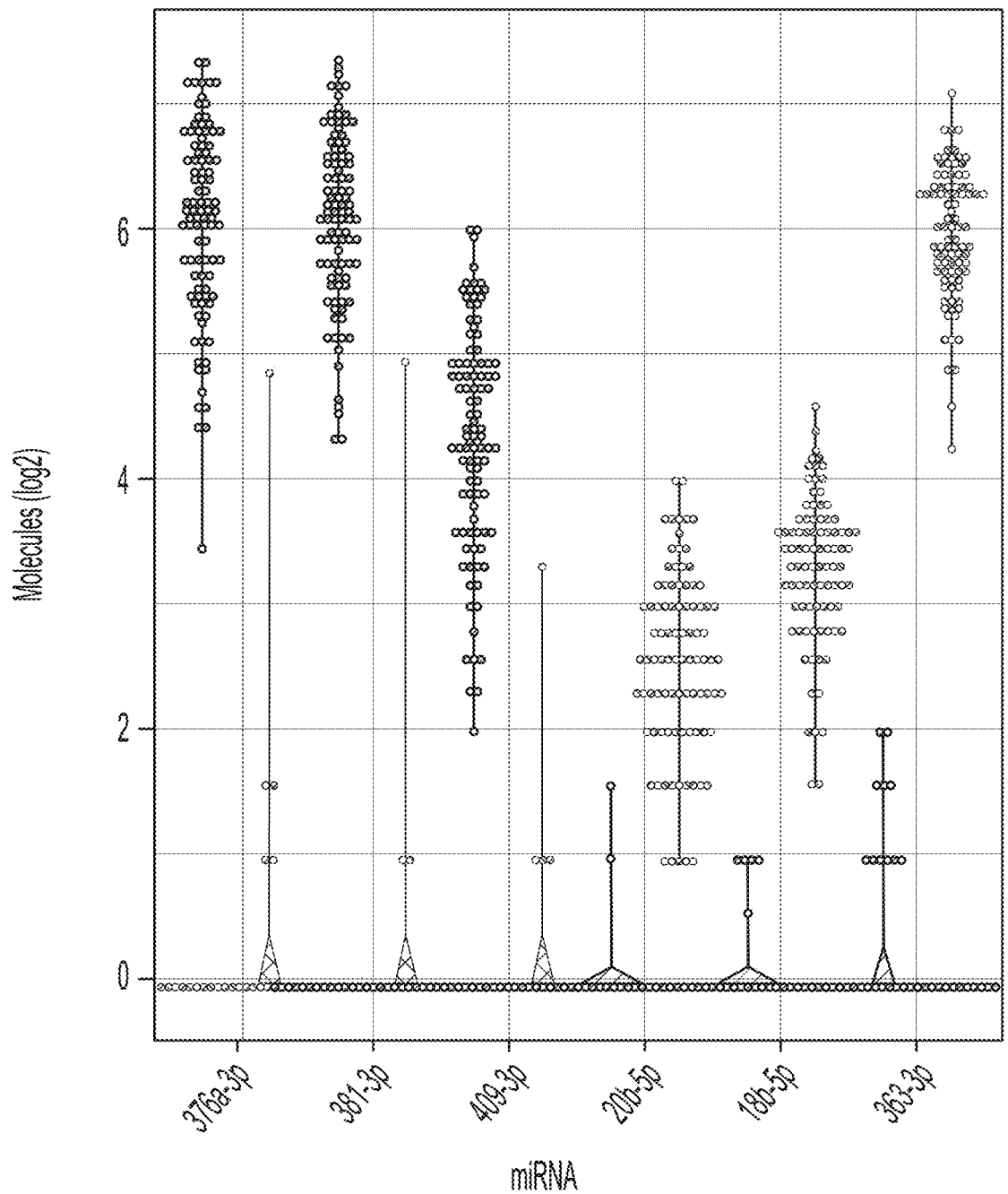

The experiments revealed that the mir-375 and the cluster of mir-371-3 were expressed more variably in individual primed hESCs. The variable miRNA expression makes primed hESCs more heterogeneous compared to naïve ones. In fact, a few individual primed hESCs had very high expression of these miRNAs compared to the rest of the population (FIG. 5). A variability in mir-371-3 cluster expression has been noted in comparisons across human pluripotent stem cell lines (Kim et al. Cell Stem Cell 8, 695-706 (2011)) but not within cells of hESC population.

Example 7: Distinguishing Between Different Cell Types

Figure 6:
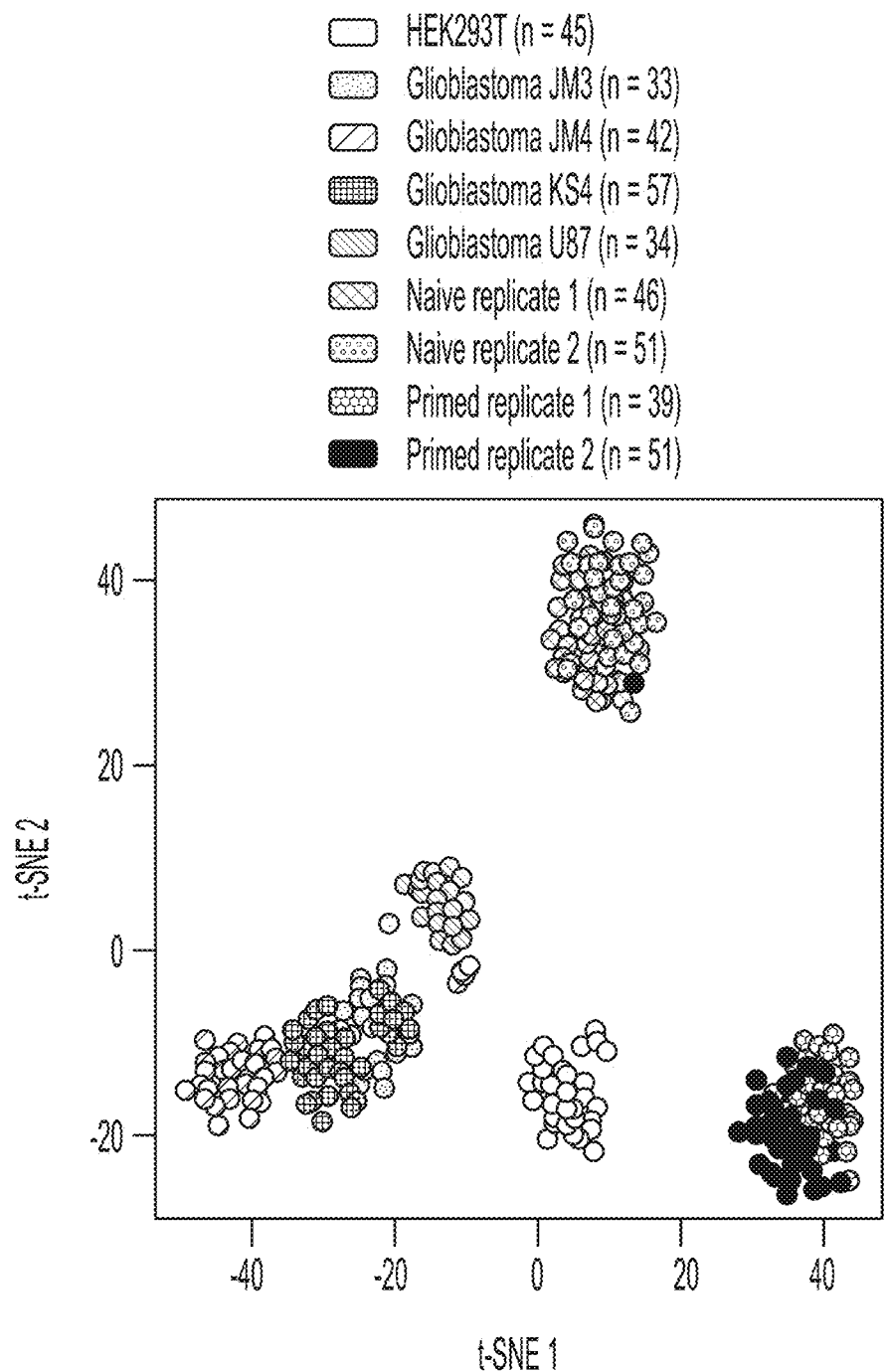
FIG. 6 illustrates clustering of an extended number of cell types. Clustering of primed and naïve hESCs, HEK293T cells and glioblastoma cells using miRNA expression with t-distributed stochastic neighbor embedding (t-SNE). Analysis included total 398 cells and 585 miRNAs expressed (>=1 molecule) in at least 2 cells. The number of cells used for each cell type is indicated inside parenthesis in the legend. Independent experimental replicates were performed for primed and naïve hESCs in order to evaluate the batch effect.

Next, it was explored whether the single-cell small-RNA expression profiled could robustly distinguish cell types. Hierarchical clustering of single-cell miRNA profiles revealed high concordance within cells of the same type and less so between cell types (FIG. 4j). Using principal component analyses (PCA) the single-cell miRNA profiles robustly grouped HEK293T cells apart from the hESCs and even separated the naïve from the primed hESCs (FIG. 4k), whereas the sparser profiles of pre-miRNAs did not. Moreover, these separations were not driven by number of miRNAs expressed (data not shown). Interestingly, the abundance profiles of sdRNAs and snoRNAs also contained cell-type specificity but not as strongly as that of the miRNAs. This is in line with data on cell-type specific expression of snoRNAs (Cavaillé et al. Proc. Natl. Acad. Sci. U.S.A. 97, 14311-14316 (2000)). Profiles of tsRNAs and tRNAs on the other hand could not cluster individual cells of the various types. To demonstrate the cell type clustering of mRNAs, single-cell mRNA-seq libraries were generated from the same cells using Smart-seq2 (Picelli et al. Nat. Methods 10, 1096-1098 (2013)). PCA could separate cell types based on mRNA expression but not to the extent of the miRNAs. To further examine the clustering capability of single-cell miRNA profiling, small-RNA libraries were generated and sequenced from more glioblastoma cells as well as more naïve and primed hESCs and HEK293T cells, which again could be robustly separated (FIG. 6). Significant differences were not detected between the naïve and primed hESCs prepared and analyzed in different batches (FIG. 6). Together, miRNA abundance profiles possess considerable potential to assign cell types and single-cell miRNA profiling might therefore have unrecognized potential to decode cellular heterogeneity within complex tissues.

Figure 7:
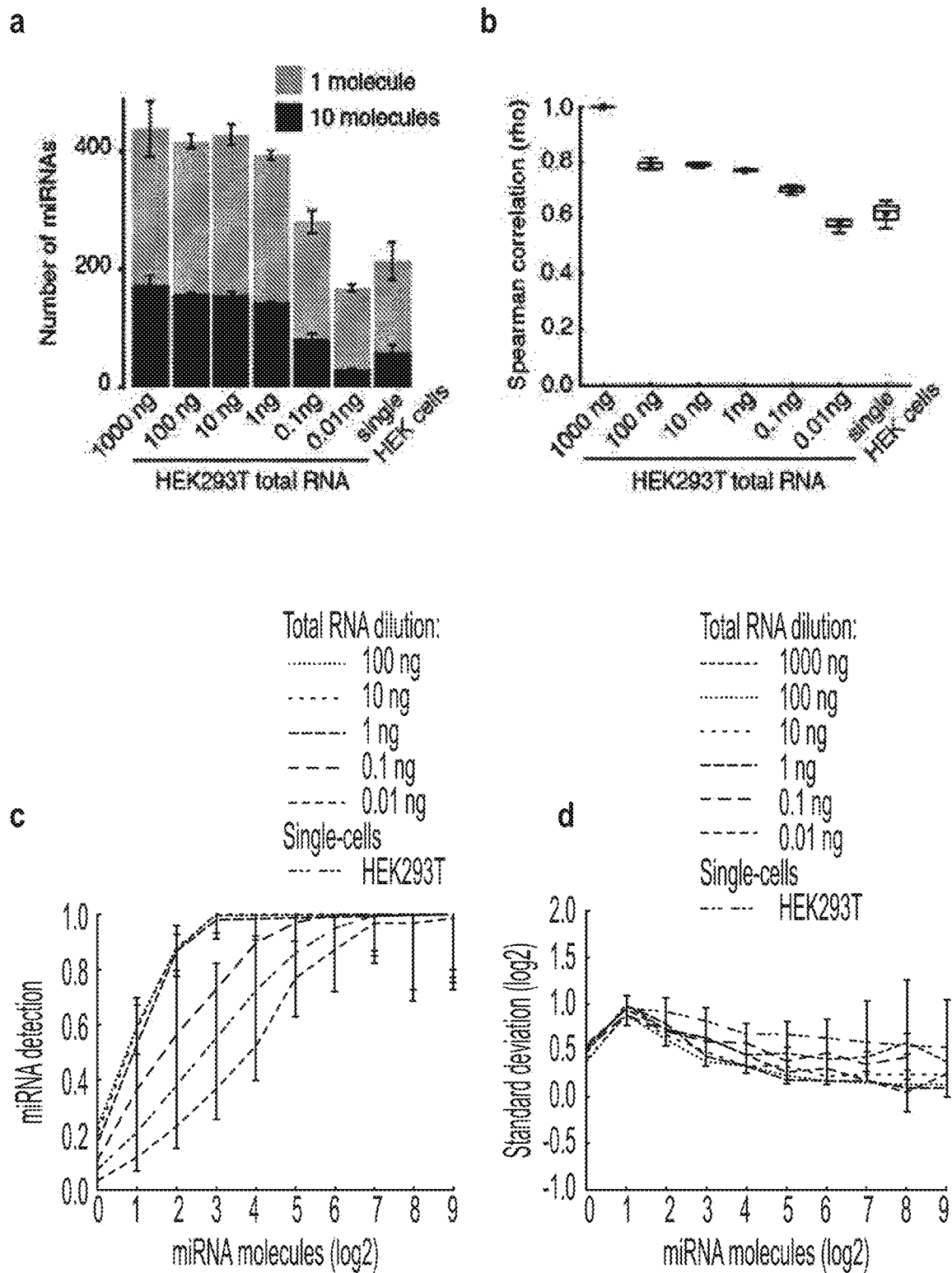
FIG. 7 illustrates comparison of miRNA profiling in diluted RNA and single cells. (a) Mean number of mature miRNAs detected in serial dilution of HEK293T RNA and in single HEK293T cells. Mature miRNAs detected by more than 10 molecules or 1 molecule were colored dark blue and light blue, respectively. Mean and standard deviation presented are derived from three replicates (for RNA dilution) and 20 individual HEK293T cells. (b) Spearman correlations of the miRNA abundance profiles within dilutions and single cells. Median and mean denoted by red line and square, respectively. (c) Fraction of mature miRNAs reproducibly detected in replicate dilutions or singe cells, binned according to molecular counts, observed in 1000 ng HEK293T RNA. Mean and 90% confidence intervals were reported. (d) Standard deviation in miRNA expression estimated within HEK293T RNA dilutions and single cells, binned according to molecular counts.
Figure 8:
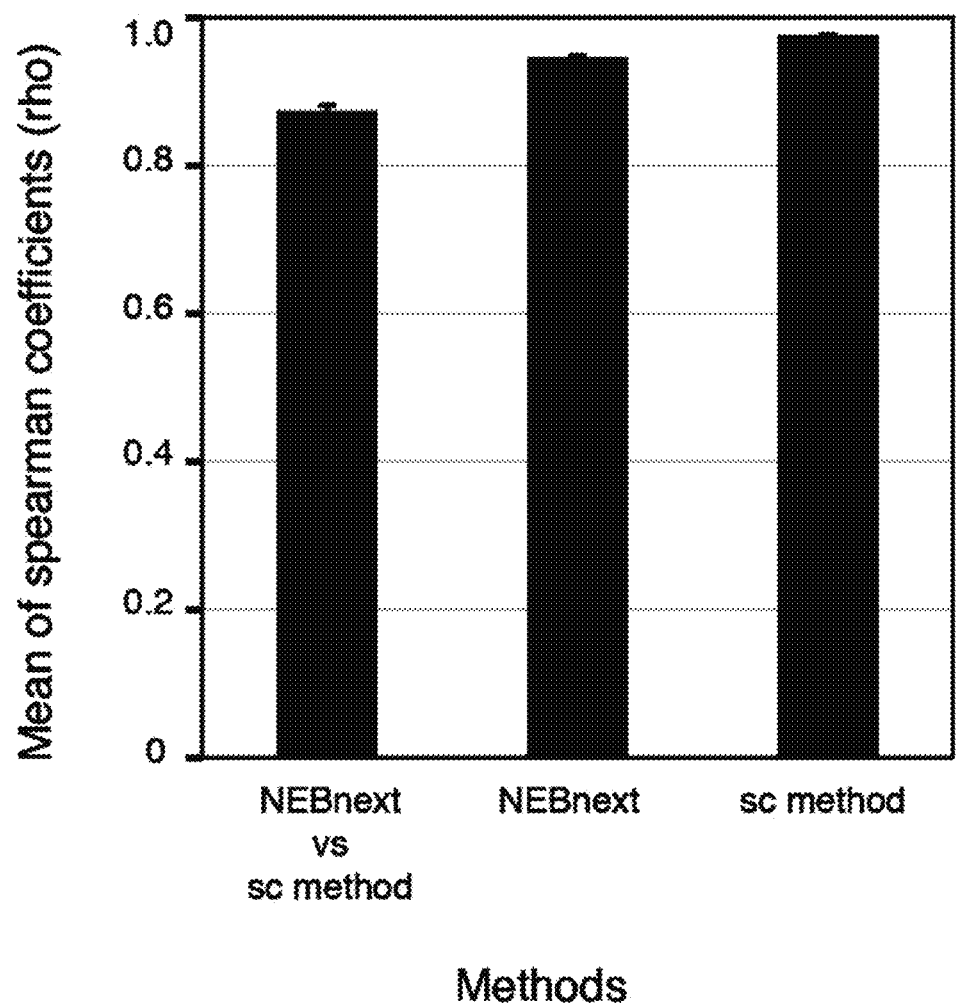
FIG. 8 illustrates correlation of miRNA expression profiles between and among preparation methods. 1000 ng of HEK293T total RNA were prepared with the single cell (sc) method and NEBNext kit according to manufacturer's protocol (but without size selection).

Example 8: Analysis of Sensitivity and Technical Variation Between HEK293T Cells and Total RNA Serial Dilutions To determine the sensitivity and quantitative accuracy of miRNA sequencing from single cells, microgram amounts of HEK293T total RNA were diluted down to nano- and picogram levels and performed the small-RNA sequencing. The number of detected mature miRNAs was fairly constant (450 detected miRNAs >=1 molecules and 170 miRNAs >=10 molecules) down to 1 ng total RNA after which technical losses were observed. At dilutions to 10 pg, close to single-cell levels, 40% of the mature miRNAs were detected, similar levels as those found in the libraries generated from individual HEK293T cells (FIG. 7a). At the molecule level, miRNA gene expression in 1000 ng HEK293T RNA was compared with dilutions and single cells. The Spearman correlations stayed relatively high down to 1 ng RNA and declined moderately with lower dilutions and confirmed the robustness in our single-cell method (FIG. 7b). The data were compared with result of a commercial kit using RNA from HEK293T cells. Analysis showed the correlation between two methods and indicated that the present single-cell small RNA protocol is reliably comparable with accepted procedures (FIG. 8). Finally, the reproducibility of the method was evaluated in miRNA expression in HEK293T RNA serial dilutions and HEK293T single cells with calculating the percentage of co-expressed genes in paired samples in expression bins (FIG. 7c). Reproducibility in gene detection decreased in 0.1 ng HEK293T RNA and lower concentrations. Variation in miRNA levels was shown for genes grouped in expression bins (FIG. 7d). Technical variation in HEK293T serial dilutions decreased slightly with increasing expression of genes. In HEK293T single cells, the biological variation of miRNA expressions is well above technical variation even in lowly expressed genes.

MicroRNA gene detection analysis (FIG. 7c) was performed over pairs of HEK293T total RNA technical replicates or single cells. MicroRNA genes were binned by abundances detected in the 1000 ng RNA sample. The mean across all possible pairs of samples within a dilution or single cells was reported together with the standard deviation calculated using the adjusted Wald method. Variation analysis (FIG. 7d) was similarly calculated on pairs of samples, binning miRNAs by the mean of log 2 molecule counts. In both figures, miRNAs were considered detected if they had a minimum molecular count of 0.2 in both samples.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention.

Although the present invention has been described in considerable detail with reference to certain preferred version thereof, other versions are possible. Therefore, the spirit and scope of the appended claims should not be limited to the description of the preferred versions contained herein.

The invention claimed is:

1. A method of treating, detecting, or preparing an RNA sample comprising the steps of:
   (a) providing a sample containing one or more ribosomal RNA molecules and one or more small RNA molecules;
   (b) masking said ribosomal RNA molecules by providing one or more oligonucleotide(s) complementary to said ribosomal RNA molecules;
   (c) contacting two or more 3' oligonucleotide adaptors with a 3' end of said small RNA molecules, wherein the 5' end of the two or more 3' oligonucleotide adaptors is adenylated and wherein the 3' end of the two or more 3' oligonucleotide adaptors is blocked by a first chemical group, to obtain a corresponding ligated 3' oligonucleotide adaptor linked to said small RNA molecules and a corresponding unreacted free form 3' oligonucleotide adaptor;
   (d) hybridizing two or more RT primer oligonucleotides to said 3' ligated oligonucleotide adaptor and said free form 3' oligonucleotide adaptor, wherein the 5' end of the RT primer is blocked by a second chemical group, and wherein said free form 3' oligonucleotide adaptor is converted to a dimer of said free form 3' oligonucleotide and said RT primer oligonucleotide;
   (e) deadenylating the 5' end of the two or more 3' oligonucleotide adaptors;
   (f) removing said dimer by digest with lambda exonuclease;
   (g) ligating a 5' oligonucleotide adaptor to a 5' end of said small RNA molecules;
   (h) performing reverse transcription of said small RNA molecules; and
   (i) performing a first PCR reaction with a RT primer and a RP1 primer and a second PCR with RP1 and indexed primers.

2. The method of claim 1, wherein said one or more oligonucleotides complementary to said small RNA molecules comprise a sequence selected from the group consisting of SEQ ID NOs: 1-11.

3. The method of claim 1, wherein the one or more oligonucleotides complementary to said small RNA molecules comprise SEQ ID NO: 1.

4. The method of claim 1, wherein one or both ends of said one or more oligonucleotides complementary to said small RNA molecules are blocked by a third chemical group.

5. The method of claim 4, wherein the third chemical group is selected from the group consisting of a biotin moiety, an amino group, an inverted nucleotide, a dideoxy nucleotide, a spacer, a dye molecule moiety, a digoxigenin moiety, a cholesterol moiety, and a phosphate.

6. The method of claim 1, wherein the 3' oligonucleotide adaptor comprises SEQ ID NO: 82.

7. The method of claim 1, wherein the RT primer oligonucleotide comprises a sequence selected from the group consisting of SEQ ID NOs: 12-16.

8. The method of claim 1, wherein the RT primer oligonucleotide comprises SEQ ID NO: 12.

9. The method of claim 1, wherein the second chemical group is selected from the group consisting of a biotin moiety, an amino group, an inverted nucleotide, a dideoxy nucleotide, a spacer, a dye molecule moiety, a digoxigenin moiety, a cholesterol moiety, and a phosphate.

10. The method of claim 1, wherein the 5' adaptor comprises a unique molecular identifier.

11. The method of claim 1, wherein the 5' oligonucleotide adaptor comprises SEQ ID NOs: 17-33.

12. The method of claim 1, wherein the 5' oligonucleotide adaptor comprises SEQ ID NO: 17.

13. The method of claim 1, wherein said RP1 primer comprises SEQ ID NO: 83.

14. The method of claim 1, wherein said indexed primers comprise a sequence selected from the group consisting of SEQ ID NOs: 34-81.

15. The method of claim 1, wherein the first chemical group is dideoxycytidine (ddC).

16. The method of claim 9, wherein the second chemical group is biotin.

* * * * *